US 010912646B2

(12) United States Patent
    Spence

(10) Patent No.: US 10,912,646 B2
(45) Date of Patent: Feb. 9, 2021

(54) METHODS, APPARATUS AND DEVICES TO TREAT HEART VALVES

(71) Applicant: Invalve Therapeutics, Inc., Louisville, KY (US)

(72) Inventor: Paul A Spence, Aventura, FL (US)

(73) Assignee: InValve Therapeutics, Inc., Louisville, KY (US)

( * ) Notice: Subject to any disclaimer, the term of this patent is extended or adjusted under 35 U.S.C. 154(b) by 0 days.

(21) Appl. No.: 16/987,927

(22) Filed: Aug. 7, 2020

(65) Prior Publication Data

US 2020/0360132 A1    Nov. 19, 2020

Related U.S. Application Data

(63) Continuation of application No. PCT/US2019/017283, filed on Feb. 8, 2019.

(60) Provisional application No. 62/627,894, filed on Feb. 8, 2018, provisional application No. 62/671,077, filed on May 14, 2018.

(51) Int. Cl.
    *A61F 2/24*    (2006.01)

(52) U.S. Cl.
    CPC ............ *A61F 2/246* (2013.01); *A61F 2/2412* (2013.01); *A61F 2/2418* (2013.01); *A61F 2/2463* (2013.01); *A61F 2/2466* (2013.01); *A61F 2220/0016* (2013.01)

(58) Field of Classification Search
    CPC .................................. A61F 2/24; A61F 2/2445
    USPC ................................ 623/2.1–2.19, 2.36–2.37
    See application file for complete search history.

(56) References Cited

U.S. PATENT DOCUMENTS

| 2011/0066233 | A1  | 3/2011  | Thornton et al. |
| 2011/0137397 | A1  | 6/2011  | Chau et al. |
| 2014/0012372 | A1  | 1/2014  | Chau et al. |
| 2014/0067048 | A1  | 3/2014  | Chau et al. |
| 2014/0172070 | A1  | 6/2014  | Seguin |
| 2014/0222136 | A1  | 8/2014  | Geist et al. |
| 2014/0228946 | A1  | 8/2014  | Chau et al. |
| 2014/0379074 | A1  | 12/2014 | Spence et al. |
| 2015/0119981 | A1* | 4/2015  | Khairkhahan ..... A61B 17/0401 623/2.36 |
| 2015/0190229 | A1  | 7/2015  | Seguin |

(Continued)

FOREIGN PATENT DOCUMENTS

WO    20190157331 A1    8/2019

OTHER PUBLICATIONS

PCT Search Report and Written Opinion for PCT/US2019/017283 filed Feb. 8, 2019.

(Continued)

*Primary Examiner* — Suzette J Gherbi

(57) ABSTRACT

Apparatus for treating blood flow regurgitation through a native heart valve (16) includes a selective occlusion device sized and configured to be implanted in the native heart valve (16) and selectively operating with at least one of the first or second native leaflets (16a, 16b) to allow blood flow through the native heart valve (16) when the heart cycle is in diastole and reduce blood flow regurgitation through the native heart valve (16) when the heart cycle is in systole. A clip structure (50) is coupled with the selective occlusion device. The clip structure (50) is configured to be affixed to a margin of at least one of the first or second native leaflets (16a, 16b) to secure the selective occlusion device to the native heart valve (16).

26 Claims, 61 Drawing Sheets

(56) References Cited

U.S. PATENT DOCUMENTS

| | | | |
|---|---|---|---|
| 2016/0302917 A1 | 10/2016 | Schewel | |
| 2016/0302922 A1 | 10/2016 | Keidar | |
| 2016/0317290 A1 | 11/2016 | Chau et al. | |
| 2016/0324639 A1 | 11/2016 | Nguyen et al. | |
| 2016/0338826 A1* | 11/2016 | Chau | A61F 2/2445 |
| 2017/0224477 A1* | 8/2017 | Seguin | A61F 2/246 |
| 2018/0185154 A1* | 7/2018 | Cao | A61F 2/2463 |
| 2018/0296326 A1 | 10/2018 | Dixon et al. | |
| 2019/0060067 A1* | 2/2019 | Keranen | A61F 2/2445 |
| 2019/0076247 A1* | 3/2019 | Zeng | A61F 2/2466 |
| 2019/0167427 A1* | 6/2019 | Gifford, III | A61F 2/246 |
| 2019/0175343 A1* | 6/2019 | Chang | A61F 2/2445 |
| 2019/0183644 A1* | 6/2019 | Hacohen | A61F 2/2439 |
| 2020/0113677 A1* | 4/2020 | McCann | A61F 2/2466 |
| 2020/0113680 A1* | 4/2020 | Chau | A61F 2/2412 |
| 2020/0163763 A1* | 5/2020 | Zipory | A61B 17/072 |

OTHER PUBLICATIONS

The New England Journal of Medicine, "Percutaneous Repair or Medical Treatment for Secondary Mitral Regurgitation", J.F. Obadia, et al., Published Aug. 27, 2018.

* cited by examiner

METHODS, APPARATUS AND DEVICES TO TREAT HEART VALVES

CROSS-REFERENCE TO RELATED APPLICATION

This application is a continuation of PCT Application Serial No. PCT/US2019/017283 filed Feb. 8, 2019 (pending), which claims priority to U.S. Provisional Patent Application Ser. No. 62/627,894, filed on Feb. 8, 2018, and U.S. Provisional Patent Application Ser. No. 62/671,077, filed on May 14, 2018, the disclosures of which are incorporated by reference herein in their entirety.

TECHNICAL FIELD

The present disclosure generally relates to manners of treating heart valves, and more particularly, manners of reducing regurgitation of blood flow through the heart valve and thereby improving efficiency and functionality of the heart valve.

BACKGROUND

Heart valve incompetence, in various forms and affecting various valves of the heart (e.g., the aortic valve, tricuspid valve, pulmonary valve and mitral valve), has led to a growing area of research and development designed to improve heart valve functionality. Although any one or more of these native heart valves may be compromised due, for example, to congenital disorders or, more often, disease conditions, the mitral valve has received particular attention. Regurgitation of blood flow through a heart valve, such as a mitral valve, involves the backward flow of blood through the valve when the valve is supposed to be fully closed (i.e., full coaptation of the native leaflets). A diseased or otherwise compromised mitral valve will often allow regurgitated blood flow from the left ventricle into the left atrium during cardiac systole. This causes the amount of blood ejected from the left ventricle during cardiac systole to be reduced, leading to less than optimal "ejection fraction" for the patient. Thus, the patient may experience a lower quality of life due to this inefficiency of their heart or, worse, a life-threatening condition.

Surgical techniques as well as transvascular or catheter-based techniques for treatment of mitral valve incompetence have been developed and, for example, include mitral annuloplasty, attachment of the native anterior mitral leaflet to the native posterior mitral leaflet, chordal replacement and even complete mitral valve replacement.

In many cases, mitral valve regurgitation is related not to congenital defects in the mitral valve leaflets but to changes in the coaptation of the leaflets over time due to heart disease. In these situations, the native mitral leaflets are often relatively normal, but they nevertheless fail to prevent regurgitation of blood from the left ventricle into the left atrium during cardiac systole. Instead of the native anterior and posterior leaflets properly mating or coapting together completely during cardiac contraction or systole, one or more gaps between the native leaflets cause mitral regurgitation.

A current, commonly used technique for reducing mitral valve regurgitation involves the attachment of the native mitral valve anterior leaflet to the native mitral valve posterior leaflet using a clip structure. The clip structure is used to securely affix centrally located points on the margins of the anterior and posterior leaflets together. This causes the mitral valve to essentially be divided into two flow control portions, with one on each side of the clip structure. The clip structure may take a simple form that directly clips the anterior leaflet and the posterior leaflet into contact with each other at the central locations on each leaflet margin, or it may include a spacer against which each leaflet is clipped, such as by a wider, paddle type structure. In either case, the clip structure keeps the mitral leaflets securely together in a manner that withstands the repetitive forces of the heart cycle.

When the native anterior and posterior mitral leaflets are affixed together at approximately the center of the valve (i.e., A2 and P2 locations of the native leaflets), there can still be a persistent leak on one or both sides of the clip leading to regurgitation.

It would be useful to further address these and other problems or challenges associated with heart valve incompetence.

SUMMARY

In a first illustrative embodiment, apparatus for treating blood flow regurgitation through a native heart valve including first and second native leaflets is provided and generally includes a selective occlusion device and a clip structure. The selective occlusion device is sized and configured to be implanted in the native heart valve and selectively operates with at least one of the first or second native leaflets to allow blood flow through the native heart valve when the heart cycle is in the diastole and reduce blood flow regurgitation through the native heart found when the heart cycle is in systole. The clip structure is coupled with the selective occlusion device. The clip structure is configured to be affixed to a margin of at least one of the first or second native leaflets to secure the selective occlusion device to the native heart valve.

Various other additional and/or optional features are provided with some examples summarized below. The clip structure may include a clip comprised of a pair of clip elements. At least one of the clip elements is movable between open and closed positions. The clip elements capture native leaflet tissue therebetween in the closed position. The clip structure may optionally or additionally comprise first and second clips each including a pair of clip elements. At least one of the clip elements of each pair is movable between open and closed positions relative to the other clip element of each pair. The first clip may be configured to attach the first native leaflet to the selective occlusion device and the second clip may be configured to attach the second native leaflet to the selective occlusion device. As another option, a single clip structure may be used at approximately a central location between opposing native leaflets, such as the anterior and posterior native leaflets of the native mitral valve, and this single clip structure may simultaneously capture leaflet tissue of the anterior and posterior leaflets. It will be appreciated that the aspects and features discussed herein are applicable to any of the native heart valves, including the pulmonary valve, the tricuspid valve, the aortic valve and the mitral valve. For an understanding of general principles, illustrative embodiments are described in connection with treating the native mitral valve.

As further optional and/or additional features, for example, the selective occlusion device may further comprise a prosthetic heart valve including a movable valve element configured to selectively control blood flow through the native heart valve. The movable valve element may further comprise a flexible membrane configured to engage at least one of the first or second native leaflets of the native heart valve when the heart cycle is in systole and disengage the at least one of the first or second native leaflets when the heart cycle is in diastole. The flexible membrane may further include a closed end and an open end. The open end receives blood flow when the heart cycle is in systole to expand the membrane into engagement with the first and second native leaflets in systole, and the open end closes when the heart cycle is in diastole to allow blood flow between the membrane and the first and second native leaflets.

As another optional and/or additional feature, some embodiments may include a frame structure coupled with the clip structure. An annulus connector and, preferably, a non-penetrating annulus connector is coupled with the frame structure. The annulus connector is configured to engage the heart tissue without penetrating through the tissue. The frame structure is configured to extend across the native heart valve generally between the commissures, in some embodiments, and the selective occlusion device is secured in place generally between the clip structure and the annulus connector. The frame structure may extend across the native heart valve at locations in addition to or different from the commissure locations. Also in some embodiments, the annulus connector or connectors provide a first force on heart tissue generally at the annulus and the clip structure provides an opposing, second force (relative to the first force) at a lower margin of at least one of the first or second native leaflets to hold the selective occlusion device generally between the annulus connector(s) and the clip structure.

In some embodiments, the clip structure includes a pair of clip elements movable between open and closed positions, and the clip elements capture native leaflet tissue therebetween in the closed position, and may either allow the leaflet tissue to directly engage in an abutting manner (e.g., anterior leaflet to posterior leaflet) or indirectly against a spacer located between leaflet tissue. Particularly, a spacer may be mounted between the pair of clip elements and the native leaflet tissue is engaged between the respective clip elements and the spacer. Also, in some embodiments, the selective occlusion device may further comprise one or more rigid selective occlusion elements sized and configured to be implanted in the native heart valve such that at least one of the first or second native leaflets engages the rigid element when the heart cycle is in systole to reduce regurgitation of blood flow through the native heart valve, and the at least one of the first or second native leaflets disengages the rigid element when the heart cycle is in diastole to allow blood flow through the native heart valve. In some embodiments the selective occlusion device further comprises first and second selective occlusion element sized and configured to be implanted in the native heart valve such that at least one of the first or second native leaflets engages the first and second selective occlusion elements when the heart cycle is in systole to reduce blood flow through the native heart valve, and the at least one of the first or second native leaflets disengages the first and second selective occlusion elements when the heart cycle is in diastole to allow blood flow through the native heart valve. The selective occlusion element or elements may be rigid. The term "rigid" is not intended to mean that the selective occlusion device has no flexibility, but only that the selective occlusion device in these embodiments need not rely on a flexible membrane actively moving to engage and/or disengage one or more of the native leaflets. In other words, the selective occlusion element or elements may be static in operation.

In some embodiments, the apparatus further comprises at least one catheter carrying the selective occlusion device and/or the clip structure and/or the frame structure. It will be appreciated that a catheter or transvascular delivery system may include the use of multiple catheters. One or more catheters is/are configured to deliver the selective occlusion device and/or the clip structure and/or the frame structure to the site of the native heart valve. The selective occlusion device may have a collapsed condition designed for delivery in a transvascular manner and an expanded condition for implantation in the native heart valve. Likewise, the frame structure may have a collapsed condition for delivery through at least one catheter and an expanded condition for implantation in the native heart valve.

In another illustrative embodiment, apparatus for treating blood flow regurgitation through a native heart valve including first and second native leaflets is provided and generally includes a selective occlusion device coupled with a frame structure. More particularly, the selective occlusion device may be configured in any of the manners contemplated herein, such as any of the manners summarized above. The frame structure is coupled with at least one non-penetrating annulus connector and the annulus connector is configured to engage with heart tissue without penetrating through the tissue. The frame structure is configured to extend across the native heart valve generally supported by the annulus and the selective occlusion device is secured in place generally between the frame structure and the annulus connector. In some embodiments, for example, the annulus connector may be an annular element configured to essentially sit on top of the mitral annulus, in the left atrium of the native heart. In other embodiments, multiple annulus connectors may be utilized. For example, first and second annulus connectors may be used to sit or locate at the annulus level abutting the respective mitral commissures or at other generally opposite locations along the native valve annulus. It will be appreciated that any of the features discussed and/or contemplated hereby may be combined together to achieve advantageous results.

In other illustrative aspects, methods for treating blood flow regurgitation through a native heart valve are provided. In some illustrative methods, the method comprises delivering a selective occlusion device into the native heart valve between the first and second native leaflets. A clip structure is delivered in proximity to a margin of at least one of the first or second native leaflets. The clip structure is affixed to the margin of the at least one of the first or second native leaflets. The selective occlusion device is secured to the clip structure, and the selective occlusion device is then used to operate with at least one of the first or second native leaflets to allow blood flow through the native heart valve when the heart cycle is in diastole and to reduce blood flow regurgitation through the native heart valve when the heart cycle is in systole.

As with other aspects and illustrative embodiments, various additional and/or optional features of the methods may be employed. The clip structure may further include a clip comprised of a pair of clip elements and affixing the clip structure may further include moving at least one of the clip elements between open and closed positions, and capturing native leaflet tissue between the clip elements in the closed position. The clip structure, in some embodiments, may further comprise first and second clips each including a pair of clip elements, with at least one of the clip elements of each pair movable between open and closed positions relative to the other clip element of each pair. Affixing the clip structure may further comprise attaching the first clip to the first native leaflet and to the selective occlusion device, and attaching the second clip to the second native leaflet and to the selective occlusion device. The selective occlusion device may further comprise a prosthetic heart valve including a movable valve element, and using the selective occlusion device may further comprise selectively controlling blood flow through the native heart valve by moving the movable valve element between open and closed positions. In some embodiments, the movable valve element may further comprise a flexible membrane, and using the selective occlusion device may further comprise engaging at least one of the first or second native leaflets of the native heart valve with the flexible membrane when the heart cycle is in systole to reduce regurgitation of blood flow through the native heart valve, and disengaging the at least one of the first or second native leaflets from the flexible membrane when the heart cycle is in diastole to allow blood flow through the native heart valve. In some embodiments the method comprises engaging the first and second native leaflets of the native heart valve with the flexible membrane when the heart is in systole to reduce regurgitation of blood flow through the native heart valve, and disengaging the first and second native leaflets from the flexible membrane when the heart cycle is in diastole to allow blood flow through the native heart valve. The flexible membrane may include a closed end and an open end. Engaging the first and second native leaflets may further include receiving blood flow through the open end when the heart cycle is in systole to expand the membrane into engagement with the first and second native leaflets, and disengaging the first and second native leaflets may include closing the open end when the heart cycle is in diastole to allow blood flow between the membrane and the first and second native leaflets.

The method may further comprise coupling a frame structure with the clip structure. A non-penetrating annulus connector may be engaged with heart tissue proximate the native heart valve annulus, and the frame structure may be secured across the native heart valve and to the non-penetrating annulus connector such that the selective occlusion device is secured in place generally between the clip structure and the non-penetrating annulus connector. In some embodiments, a first force may be provided on heart tissue with the annulus connector or connectors, and a second force opposing the first force may be provided by the clip structure at a lower margin of at least one of the first or second native leaflets to hold the selective occlusion device between the annulus connector or connectors and the clip structure. For example, these forces may be pushing and pulling type forces. Also in some embodiments, the method may utilize a pair of clip elements as the clip structure, with at least one of the clip elements movable between open and closed positions, and affixing the clip structure may further comprise capturing the native leaflet tissue between the clip elements and a spacer when the at least one clip element is moved to the closed position. In other embodiments, the clip structure causes abutting leaflet tissue to directly contact when the clip is closed. Also in some embodiments, the selective occlusion device may further comprise a rigid element, as generally discussed herein, and engaging the rigid element of the selective occlusion device with at least one of the first or second native leaflets when the heart cycle is in systole reduces blood flow regurgitation through the native heart valve, and disengaging the rigid element from the at least one of the first or second native leaflets when the heart cycle is in diastole allows blood flow through the native heart valve between the rigid element and the at least one of the first or second native leaflets.

In various illustrative embodiments of the methods, the selective occlusion device and/or the clip structure and/or the frame structure, as well as other components used in the methods, may be delivered and implanted in a transvascular manner. For example, the selective occlusion device may be directed with or without the clip structure through at least one catheter with the selective occlusion device in a collapsed condition. The selective occlusion device is extruded from the distal end of the at least one catheter, and the device is expanded in the native heart valve. The method may further comprise transvascularly delivering a frame structure to the native heart valve, transvascularly delivering the clip structure to the native heart valve, and engaging a non-penetrating annulus connector with heart tissue proximate the native heart valve annulus. The frame structure may be secured across the native heart valve and to the non-penetrating annulus connector such that the selective occlusion device is secured in place generally between the clip structure and the non-penetrating annulus connector. In another optional and/or additional aspect, the method may further comprise transvascularly delivering a clip structure capturing device, capturing the clip structure with the capturing device, and connecting the clip structure to the frame structure during implantation of the selective occlusion device in the native heart valve.

In another illustrative method for treating blood flow regurgitation through a native heart valve including at least first and second native leaflets, the method comprises delivering a selective occlusion device into the native heart valve between the first and second native leaflets. A frame structure is delivered in proximity to the native heart valve. The frame structure is affixed to the annulus of the native heart valve with a non-penetrating annulus connector. The selective occlusion device is secured to the frame structure. The selective occlusion device is then used to operate with at least one of the first or second native leaflets to allow blood flow through the native heart valve when the heart cycle is in diastole and to reduce blood flow regurgitation through the native heart valve when the heart cycle is in systole. Any of the additional and/or optional features summarized, discussed or otherwise contemplated herein may be used in carrying out this general method.

In another illustrative embodiment, an apparatus for treating blood flow regurgitation through a native heart valve including first and second native leaflets is provided and generally includes a prosthetic heart valve, and a clip structure. More specifically, the prosthetic heart valve includes a peripheral, generally cylindrical frame movable between collapsed and expanded conditions, and a plurality of prosthetic leaflets secured within the peripheral, generally cylindrical frame. The prosthetic leaflets are movable between open and closed conditions to respectively control blood flow through the prosthetic heart valve. The frame is implanted by expansion against the first and second native leaflets of the native heart valve. The clip structure is coupled with the frame of the prosthetic heart valve. The clip structure is configured to be affixed to a margin of at least one of the first or second native leaflets to secure the prosthetic heart valve to the native heart valve. As optional and/or additional aspects, the clip structure may further comprise first and second clips each including a pair of clip elements, with at least one of the clip elements of each pair movable between open and closed positions relative to the other clip element of each pair. The first clip is configured to attach the first native leaflet to the prosthetic heart valve and the second clip is configured to attach the second native leaflet to the prosthetic heart valve. The prosthetic heart valve may take any desired form, with one example being an expandable stent structure comprising the frame.

As another illustrative method, the prosthetic heart valve may be transvascularly delivered in a collapsed condition to a space within the native heart valve. The prosthetic heart valve is clipped to the first and second native leaflets by capturing margins of the first and second native leaflets between respective clip elements. The prosthetic heart valve is expanded against the first and second native leaflets, and the flow of blood is controlled through the native heart valve by movement of the prosthetic leaflets of the prosthetic heart valve. As optional and/or additional features of the method, clipping the prosthetic heart valve may further comprise capturing the anterior leaflet of the native mitral valve with a first clip, and capturing the posterior native leaflet of the native mitral valve with a second clip.

In another illustrative embodiment, apparatus for treating blood flow regurgitation through a native heart valve including first and second native leaflets generally includes a selective occlusion device and a clip structure capturing device. The selective occlusion device is sized and configured to be implanted in the native heart valve and selectively operates with at least one of the first or second native leaflets to allow blood flow through the native heart valve when the heart cycle is in diastole and reduce blood flow regurgitation through the native heart valve when the heart cycle is in systole. The clip structure capturing device is extendable from at least one catheter and configured to capture a clip structure or other anchor securing the first and second native leaflets to each other, to allow the clip structure or other anchor to be coupled with the selective occlusion device. The clip structure capturing device may further comprise a snare or suture loop device. At least one catheter may carry the selective occlusion device and the clip structure capturing device. In this case, the at least one catheter is configured to deliver the selective occlusion device and the clip structure capturing device to the site of the native heart valve, and the selective occlusion device has a collapsed condition for delivery through the at least one catheter and an expanded condition for implantation in the native heart valve. It will be appreciated that the different components may be carried and delivered in different catheters. Any of the other features or aspects of this disclosure may be additionally or optionally used in this embodiment.

In another illustrative method, blood flow regurgitation through a native heart valve including first and second native leaflets may be treated by capturing a clip structure or other anchor secured to a margin of at least one of the first or second native leaflets. A selective occlusion device is delivered into the native heart valve between the first and second native leaflets while the clip structure or other anchor is captured, and the selective occlusion device is secured to the clip structure or other anchor. The selective occlusion device is used to operate with at least one of the first or second native leaflets to allow blood flow through the native heart valve when the heart cycle is in diastole and reduce blood flow regurgitation through the native heart valve when the heart cycle is in systole. Capturing the clip structure may further comprise ensnaring the clip structure with a tensile member. Securing the selective occlusion device may further comprise attaching a tensile member between the clip structure and the selective occlusion device. Securing the selective occlusion device may further comprise attaching the clip structure to a frame member of the selective occlusion device. Again, this method may additionally or optionally include other features or aspects contemplated by the methods disclosed or contemplated herein.

In another illustrative embodiment, a selective occlusion device is provided for assisting with control of blood flow through a native heart valve including first and second native leaflets. The selective occlusion device is sized and configured to be implanted in the native heart valve adjacent a clip structure that separates the native heart valve into at least two internal valve sections between the first and second native leaflets and two external valve sections behind the first and second native leaflets. Generally, the selective occlusion device may be implanted on at least one side of, for example, a clip structure that secures two native leaflets of a heart valve together and thereby essentially bisects the native valve into two internal sections through which blood will flow through the valve, and two exterior sections outside of the leaflets (i.e., behind the leaflets). The selective occlusion device may control blood flow in any desired manner, including as examples, one or more of the manners contemplated herein.

In another illustrative method, a selective occlusion device is delivered into the native heart valve between the first and second native leaflets and on at least one side of a clip structure separating the native heart valve into at least two internal valve sections between the first and second native leaflets and two external valve sections behind the first and second native leaflets. The selective occlusion device is used to assist with controlling blood flow through the native heart valve during the heart cycle. Again, the selective occlusion device may control blood flow in any desired manner, including as examples, one or more of the manners contemplated herein.

Additional features, aspects and/or advantages will be recognized and appreciated upon further review of a detailed description of the illustrative embodiments taken in conjunction with the accompanying drawings.

DESCRIPTION OF ILLUSTRATIVE EMBODIMENTS

The detailed description herein serves to describe non-limiting embodiments or examples involving various inventive concepts and uses reference numbers for ease of understanding these examples. Common reference numbers between the figures refer to common features and structure having the same or similar functions, as will be understood. While various figures will have common reference numbers referring to such common features and structure, for purposes of conciseness, later figure descriptions will not necessarily repeat a discussion of these features and structure.

Figure 1A:
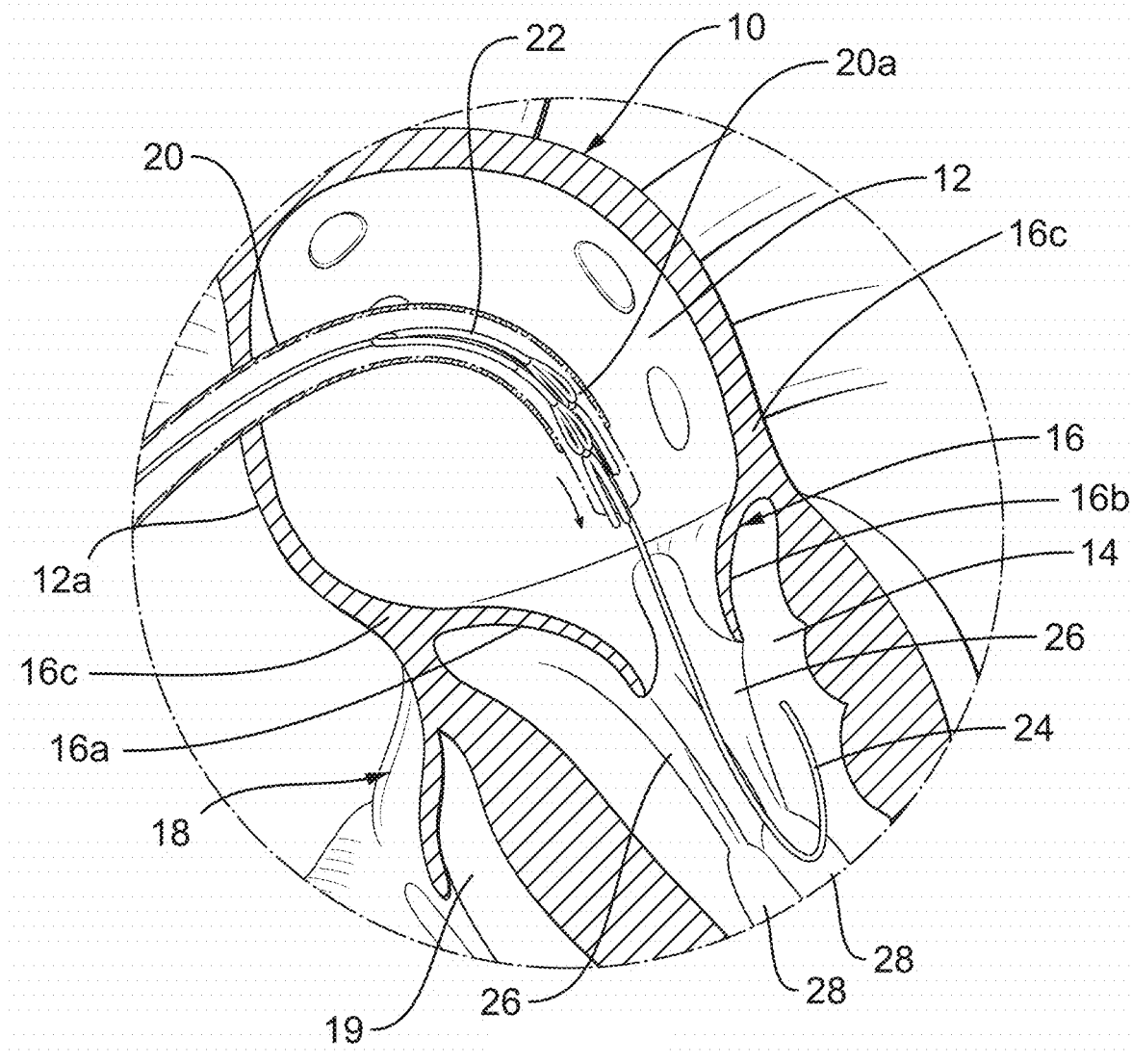
FIG. 1A is a schematic view illustrating a system constructed in accordance with one illustrative embodiment.

Referring first to FIG. 1A, a native heart 10 is shown and includes a left atrium 12, a left ventricle 14, and a native mitral valve 16, which controls blood flow from the left atrium 12 to the left ventricle 14. The tricuspid valve 18 is also shown in communication with the right ventricle 19. The mitral valve 16 includes an anterior leaflet 16a, a posterior leaflet 16b and a native valve annulus 16c. When the mitral valve 16 is functioning properly, it will open to allow blood flow from the left atrium 12 into the left ventricle 14 during the diastole portion of the heart cycle. When the heart 10 contracts during systole, the anterior and posterior native mitral leaflets 16a, 16b will fully coapt or engage with one another to stop any blood flow in the reverse direction into the left atrium 12 and blood in the left ventricle 14 will be ejected efficiently and fully through the aortic valve (not shown). A catheter 20 carries a collapsed selective occlusion device 22 along a guide wire 24. In this illustrative procedure, the catheter 20 is delivered transeptally across the inter-atrial septum 12a. It will be appreciated that any other transcatheter approach, or other surgical approaches of various levels of invasiveness, may be used instead. The patient may or may not be on bypass and the heart may or may not be beating during the procedure. As further shown in FIG. 1A, the native mitral leaflets 16a, 16b are supported by chordae tendineae 26 attached to papillary muscles 28. As schematically illustrated in FIG. 1A, the anterior and posterior native mitral leaflets 16a, 16b may not properly coapt or engage with one another when the heart cycle is in systole. Insufficient coaptation of the leaflets 16a, 16b leads to blood flow out of the left ventricle 14 in a backward direction, or in regurgitation, through the mitral valve 16 into the left atrium 12 instead of fully through the aortic valve (not shown).

Figure 1B:
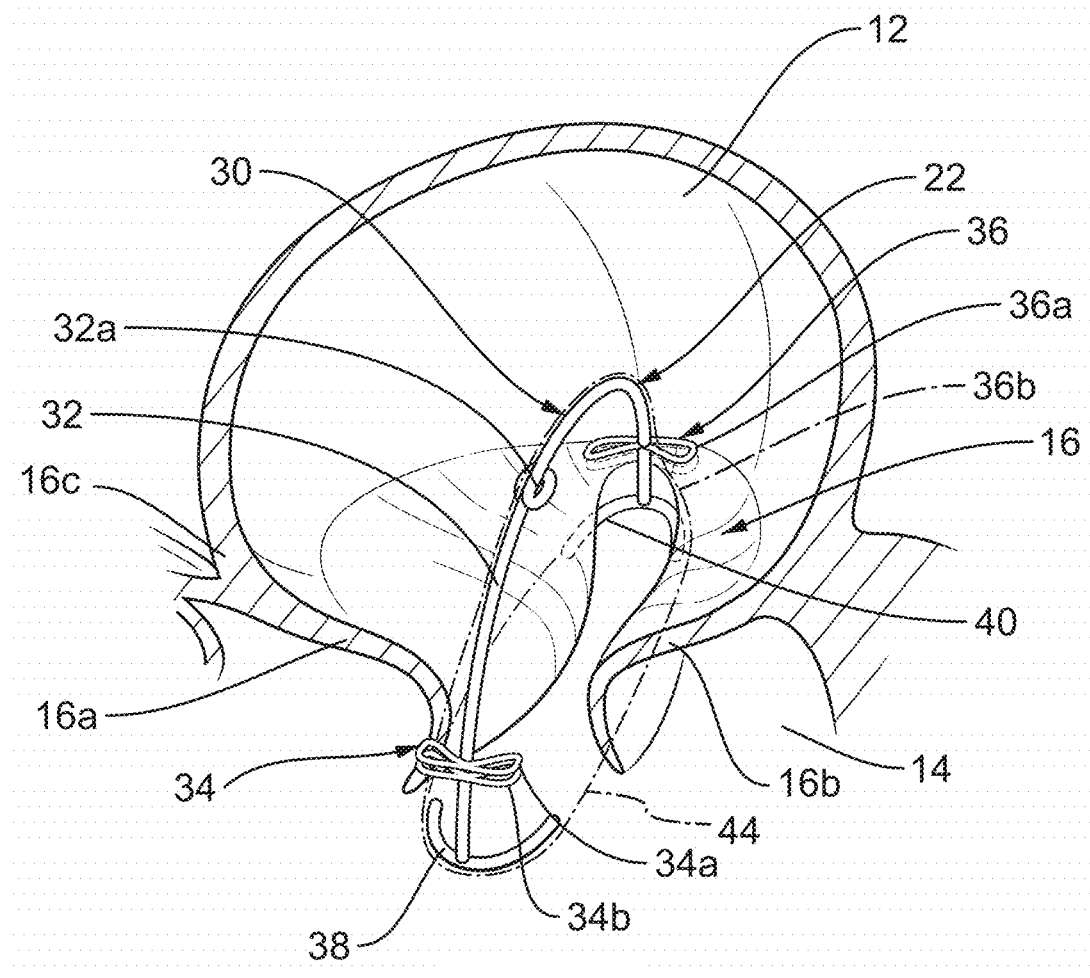
FIG. 1B is a schematic perspective view of a native left atrium and mitral valve, similar to FIG. 1A, but illustrating installation of the catheter delivered selective occlusion device.
Figure 1C:
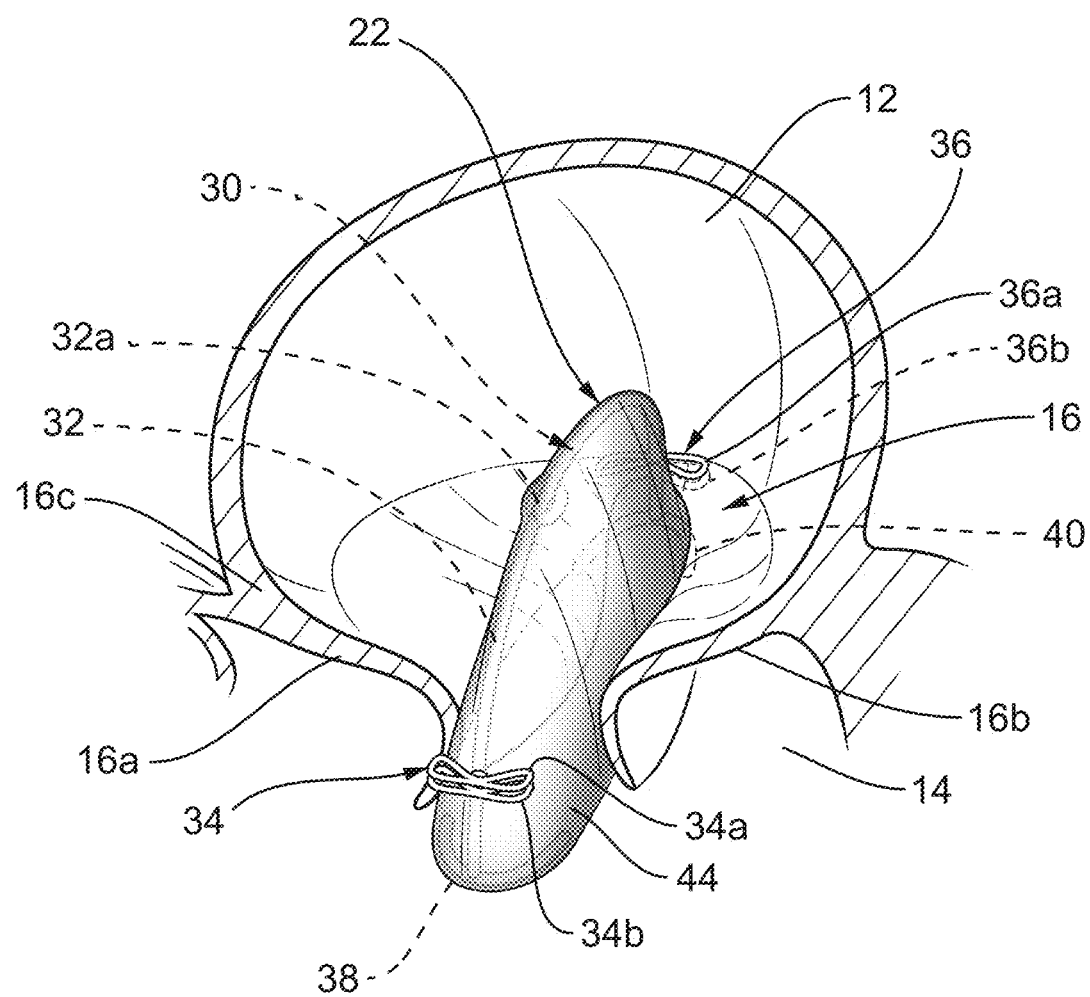
FIG. 1C is a schematic perspective view similar to FIG. 1B, but illustrating the membrane of the selective occlusion device in place over the frame structure.

Now referring to FIG. 1A in conjunction with FIGS. 1B and 1C, the selective occlusion device 22 has been fully extruded or extended from the distal end 20a of the catheter 20, and transformed from the collapsed position or condition shown in FIG. 1A within the catheter 20, to the expanded condition shown in FIGS. 1B and 1C. As further shown in FIGS. 1B and 1C, the selective occlusion device 22 comprises a collapsible and expandable frame structure 30. The frame structure 30 is comprised of a curved frame member 32 generally extending across the native mitral valve 16 while being supported or stabilized at the native annulus 16c. The selective occlusion device 22 is formed in a manner allowing it to be collapsed for delivery as shown in FIG. 1A, but expanded to the exemplary form shown in FIGS. 1B and 1C. This may be accomplished in many ways. For example, the frame structure 30 may be comprised of flexible polymers, metals such as super-elastic or shape memory metals or other materials. The selective occlusion device 22 may, for example, expand into a preformed shape through the use of shape memory materials. The frame structure 30 may be covered partially or completely by fabrics such as the Dacron, Teflon and/or other covering materials such as used in the manufacture of prosthetic cardiac valves or other implants. More specifically, the frame structure 30 includes a curved frame member 32 which, in this embodiment, and/or other embodiments, extends from one commissure to the other. The frame member 32 may instead extend from other portions of the heart tissue generally located at the annulus region. At opposite ends, the frame structure 30 is supported by respective first and second non-penetrating annulus connectors 34, 36. As an example of a non-penetrating annulus connector, these connectors are configured with respective upper and lower connector elements 34a, 34b and 36a, 36b. These connector elements 34a, 34b and 36a, 36b respectively sandwich or capture annulus tissue therebetween at each commissure. The connector elements 34a, 34b and 36a, 36b are each shown as "butterfly-type" connectors that may be slipped or inserted into place with native leaflet tissue sandwiched or secured therebetween. It will be appreciated that other tissue trapping connectors may be used instead, and/or other penetrating or non-penetrating connectors. Non-penetrating connectors are advantageous because they cause no damage that would otherwise occur due to penetrating connectors, and they allow for position adjustment. The frame structure 30 further includes first and second membrane support members 38, 40 at opposite ends configured to be located in the left ventricle 14 to support a flexible membrane 44 in a slightly open condition. Together with the frame structure 30, the flexible membrane 44 forms a selective occlusion device that works in conjunction with the native mitral valve leaflets 16a, 16b to control blood flow through the mitral valve 16. The flexible membrane 44, in this embodiment acts as a prosthetic heart valve by moving in coordination with the leaflets 16a, 16b as will be described below. In other embodiments, the selective occlusion device need not have any moving part that moves in conjunction with the leaflets 16a, 16b. The flexible membrane 44 is secured at opposite portions of the frame structure 30 to the support members 38, 40 in any suitable manner, such as adhesive, mechanical securement, suturing, fasteners, etc. As further shown, a considerable portion at a lower margin of the flexible membrane 44 is not attached to the frame structure 30. The membrane support members 38, 40 are short, curved members and remaining membrane portions at the lower margin of the flexible membrane 44 are not directly attached to any frame portion. This allows the flexible membrane to billow, expand or inflate outward as will be discussed further below during systole to engage with the native leaflets 16a, 16b and prevent regurgitation of blood flow in a reverse direction through the mitral valve 16 when the heart cycle is in systole.

The flexible membrane 44 may be formed of various types of thin, flexible materials. For example, the materials may be natural, synthetic or bioengineered materials. Materials may include valve tissue or pericardial tissue from animals, such as cows and pigs, or other sources. Synthetic materials such as ePTFE, Dacron, Teflon or other materials or combinations of materials may be used to construct the flexible membrane 44. Flexibility of the frame structure 30 together with the flexibility of the flexible membrane 44 provides for operation of the selective occlusion device 22 and the manners contemplated herein, and may also help prevent failure due to fatigue from repeated cycling movement of the selective occlusion device 22 in the heart 10. It will be appreciated that FIG. 1B shows the flexible membrane 44 removed for a clear view of the frame structure 30, and in this figure the flexible membrane 44 is in broken lines, while in FIG. 10 the flexible membrane 44 is shown in solid lines, with the heart cycle in systole and the flexible membrane 44 fully engaging the native leaflets 16a, 16b to reduce regurgitation of blood flow through the mitral valve 16. The flexible membrane 44 may be sutured to the frame structure 30 using techniques employed by the prosthetic heart valve industry for the manufacture of prosthetic aortic and mitral valves. The frame may be made from one or more layers of material, such as super-elastic or shape memory material and the membrane 44 may be suitably secured. One manner may be trapping the flexible membrane 44 between layers of the frame structure 30. To retain the membrane 44 in place, fabric covering(s) (not shown) over a metallic frame may aid in attaching the membrane 44 to the frame structure 30.

Figure 2A:
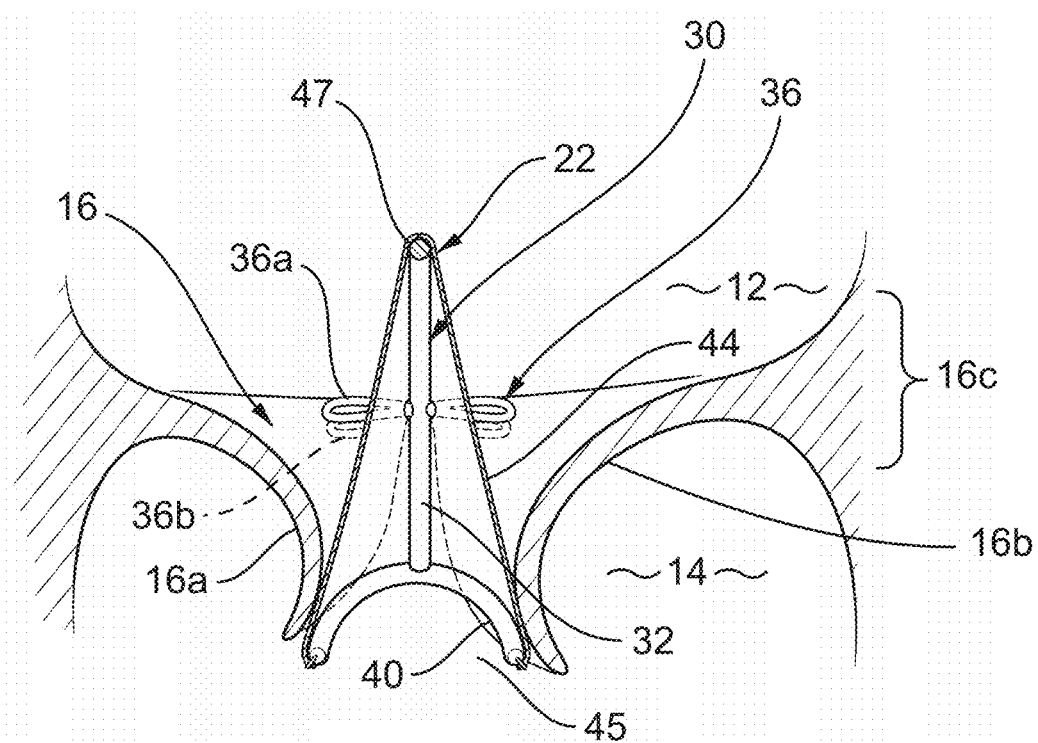
FIG. 2A is a cross-sectional view taken transversely through the selective occlusion device along line 2A-2A of FIG. 3A when the heart cycle is in systole.
Figure 2B:
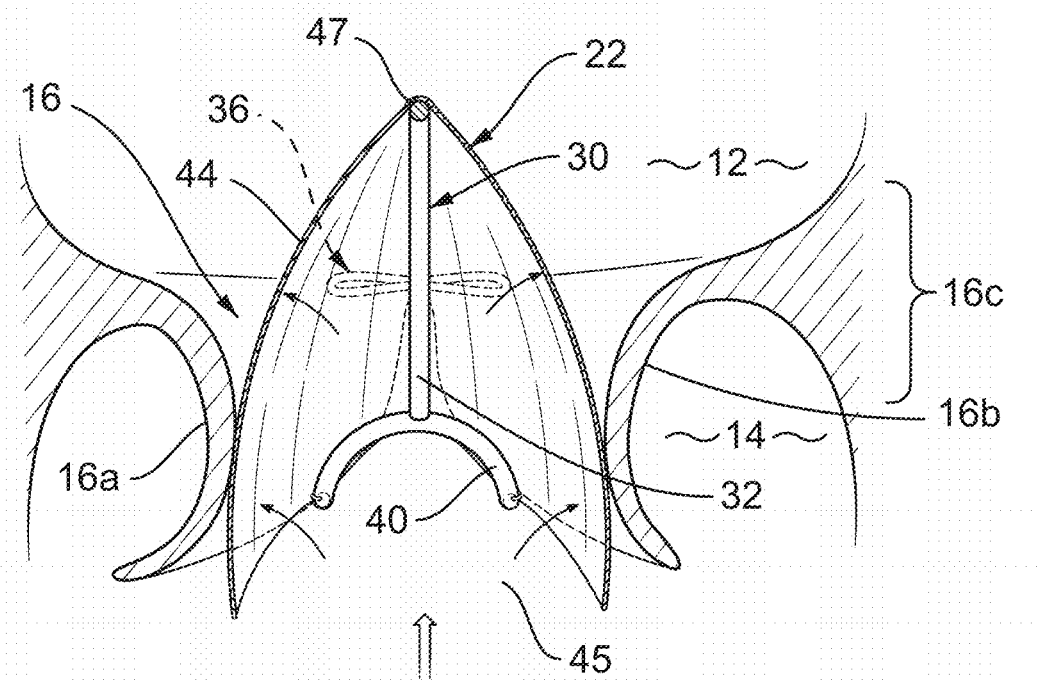
FIG. 2B is a cross-sectional view similar to FIG. 2A, during the systole phase of the heart cycle, but taken along line 2B-2B of FIG. 3A.
Figure 2C:
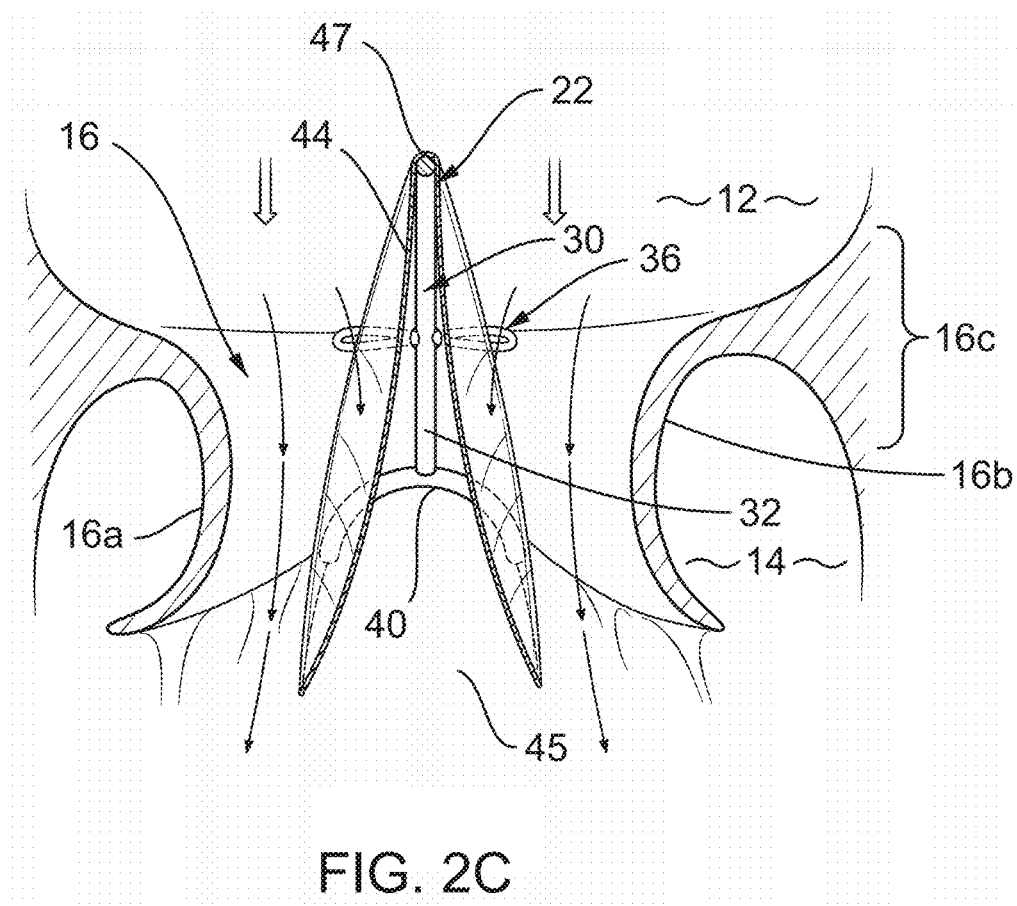
FIG. 2C is a cross-sectional view similar to FIG. 2B, but illustrating the native mitral valve during and the selective occlusion device while in the diastole phase of the heart cycle.
Figure 3A:
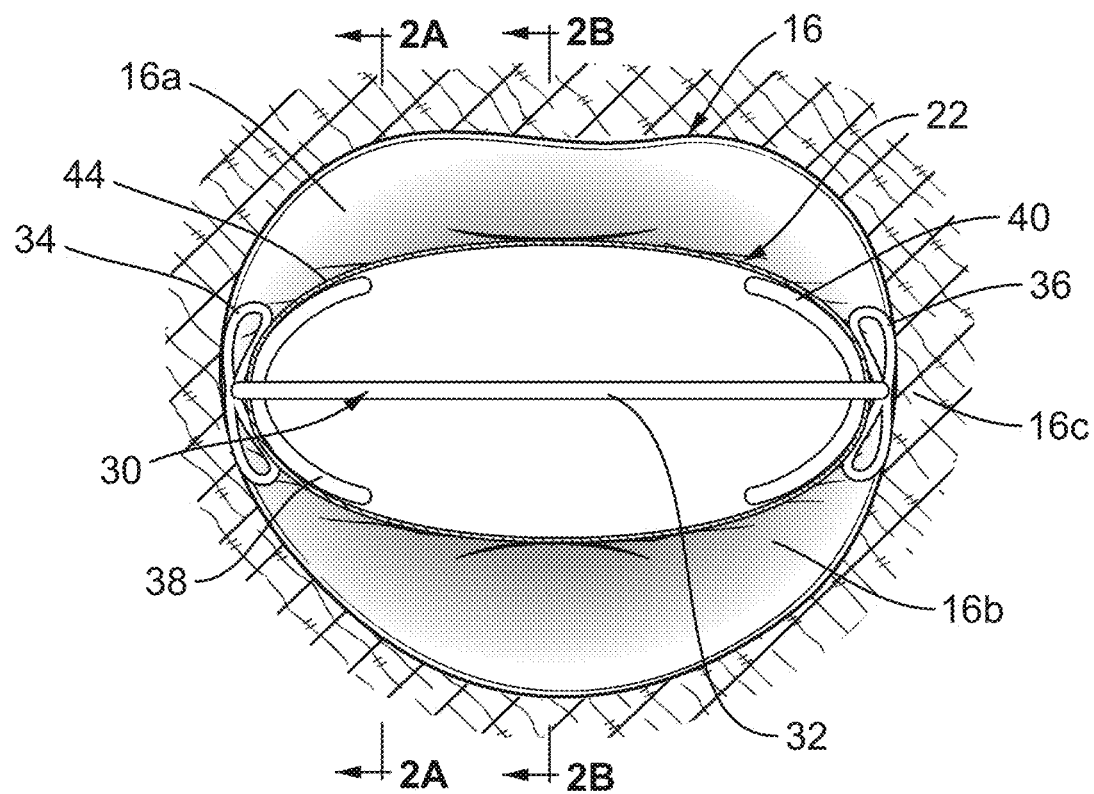
FIG. 3A is a top view of the native mitral valve and the selective occlusion device while the heart is in the systole phase.
Figure 3B:
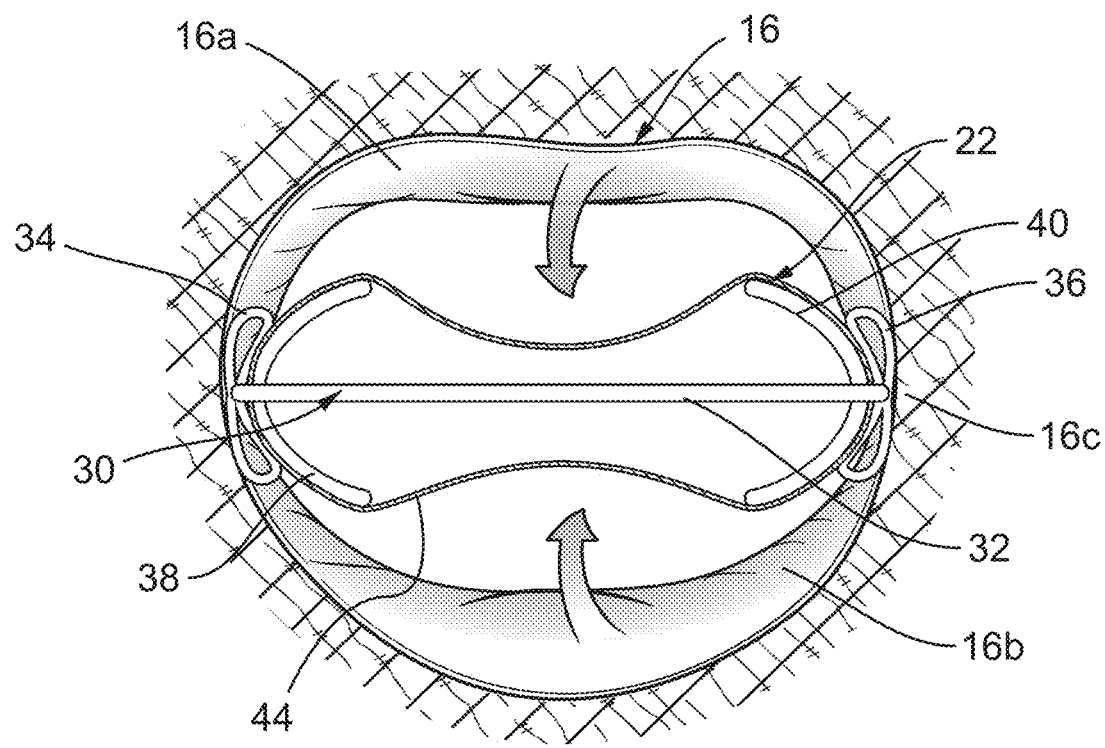
FIG. 3B is a top view similar to FIG. 3A, but illustrating the device and native mitral valve while the heart is in the diastole phase.

FIGS. 2A, 2B and 2C are transverse cross-sections through the selective occlusion device 22 and the mitral valve 16 shown in FIGS. 1A through 10. FIG. 2A illustrates the device 22 in a cross section along line 2A-2A of FIG. 3A, while FIG. 2B shows the selective occlusion device 22 in cross section along line 2B-2B of FIG. 3A, with each of these two figures showing the heart cycle in systole. FIGS. 3A and 3B are top views respectively showing the systole and diastole conditions, but not illustrating the hinge 32a that may be provided to assist with folding during delivery. FIG. 2C is similar to FIG. 2B but showing the selective occlusion device 22 when the heart cycle is in diastole. In systole (FIGS. 2A, 2B and 3A), which is when the native mitral valve 16 is supposed to fully close to prevent blood flow back into the left atrium 12, the pressurized blood will flow through the open end 45 of the flexible membrane and be prevented from flowing through the closed end 47, at least to any substantial degree. As will be appreciated from a review of some embodiments, a small vent may be provided in the flexible membrane. Because the flexible membrane billows or expands outwardly in the direction of the arrows shown in FIG. 2B, the native mitral leaflets 16a, 16b will seal against or coapt with the flexible membrane 44 to prevent blood flow regurgitation. In this manner, native mitral leaflets 16a, 16b that would not otherwise properly seal together or coapt will seal in systole against the flexible membrane 44. To ensure coaptation, one or more portions of the flexible membrane 44 adjacent to frame structure 30 will move away from the adjacent frame structure into contact with the native leaflet(s) 16a, 16b. In other words, only a portion of the lower margin of the flexible membrane 44 is affixed to frame structure 30. As further shown in FIG. 2B, there may be extra membrane material adjacent the membrane support members 38, 40 to allow for the expanded membrane condition. As further shown in FIGS. 2C and 3B, when the heart cycle is in diastole and blood flow needs to occur from the left atrium 12 into the left ventricle 14 (during the filling portion of the heart cycle), the blood will push past the flexible membrane 44 and the flexible membrane 44 will move into a collapsed or contracted condition while the native mitral leaflets 16a, 16b move apart or away from each other in the opposite direction to facilitate blood flow in the direction of the arrows. The arch-shaped membrane support members 38, 40 maintain a separation between lower margins or edges of the flexible membrane 44 to force blood to fill the inside or interior of the membrane 44 during systole through the open end 45, causing the membrane 44 to expand or billow outward so that the membrane 44 fills the gap between the native mitral valve leaflets 16a, 16b. The arch-shaped or curved support members 38, 40, and/or other portions of the frame structure 30, may be formed using a central wire and a fabric cover around the wire. Other constructions are possible as well, such as using soft, sponge-like material, and fabrics in conjunction with more structurally supportive material such as metal and/or plastic. The filling and emptying of the flexible membrane 44 through the open end 45 can ensure that there is washing or rinsing of the underside of the membrane 44 with each heartbeat to prevent clot formation, and any resulting embolization of clot material.

Figure 4A:
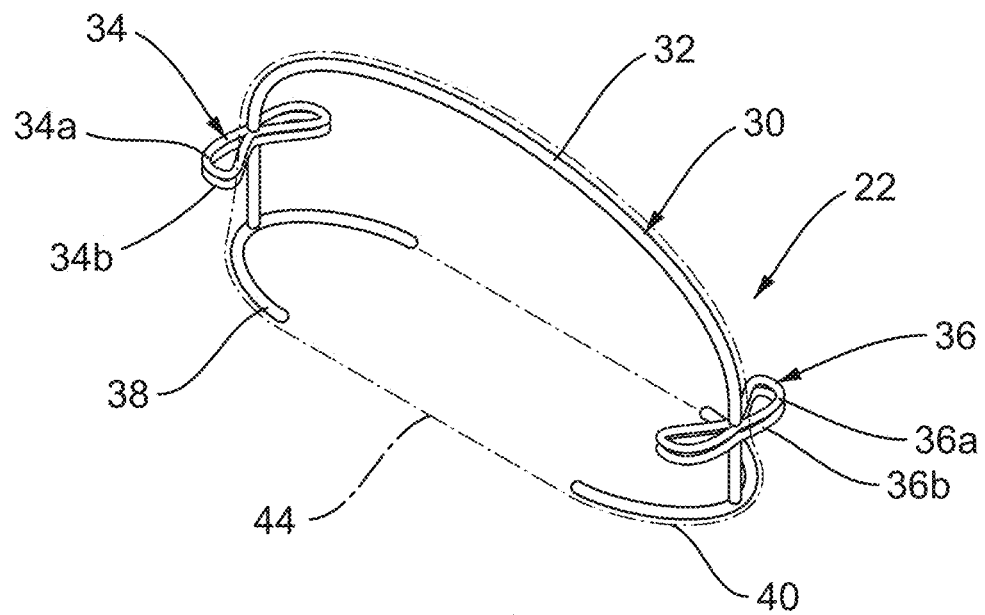
FIG. 4A is a perspective view of the device as shown in the previous figures, with the membrane of the device removed for clarity, and showing only the frame structure in solid lines.
Figure 4B:
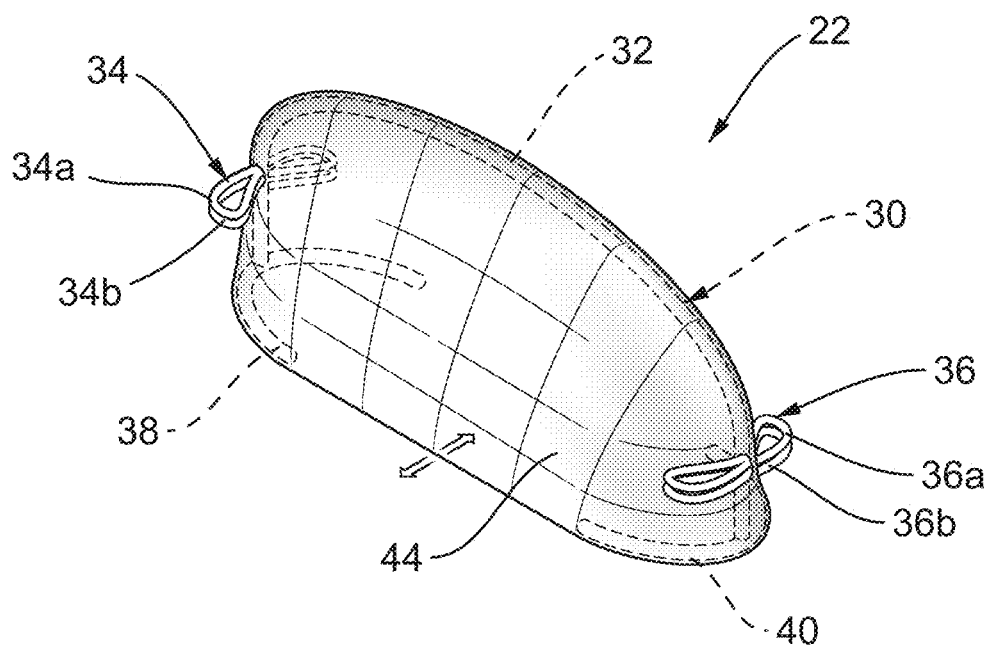
FIG. 4B is a perspective view similar to FIG. 4A, but illustrating the membrane applied to the frame structure of the device.

FIGS. 4A and 4B are respectively similar to FIGS. 1B and 1C, but illustrate the selective occlusion device 22 isolated from the native mitral valve 16 (FIGS. 1B and 1C).

Figure 5A:
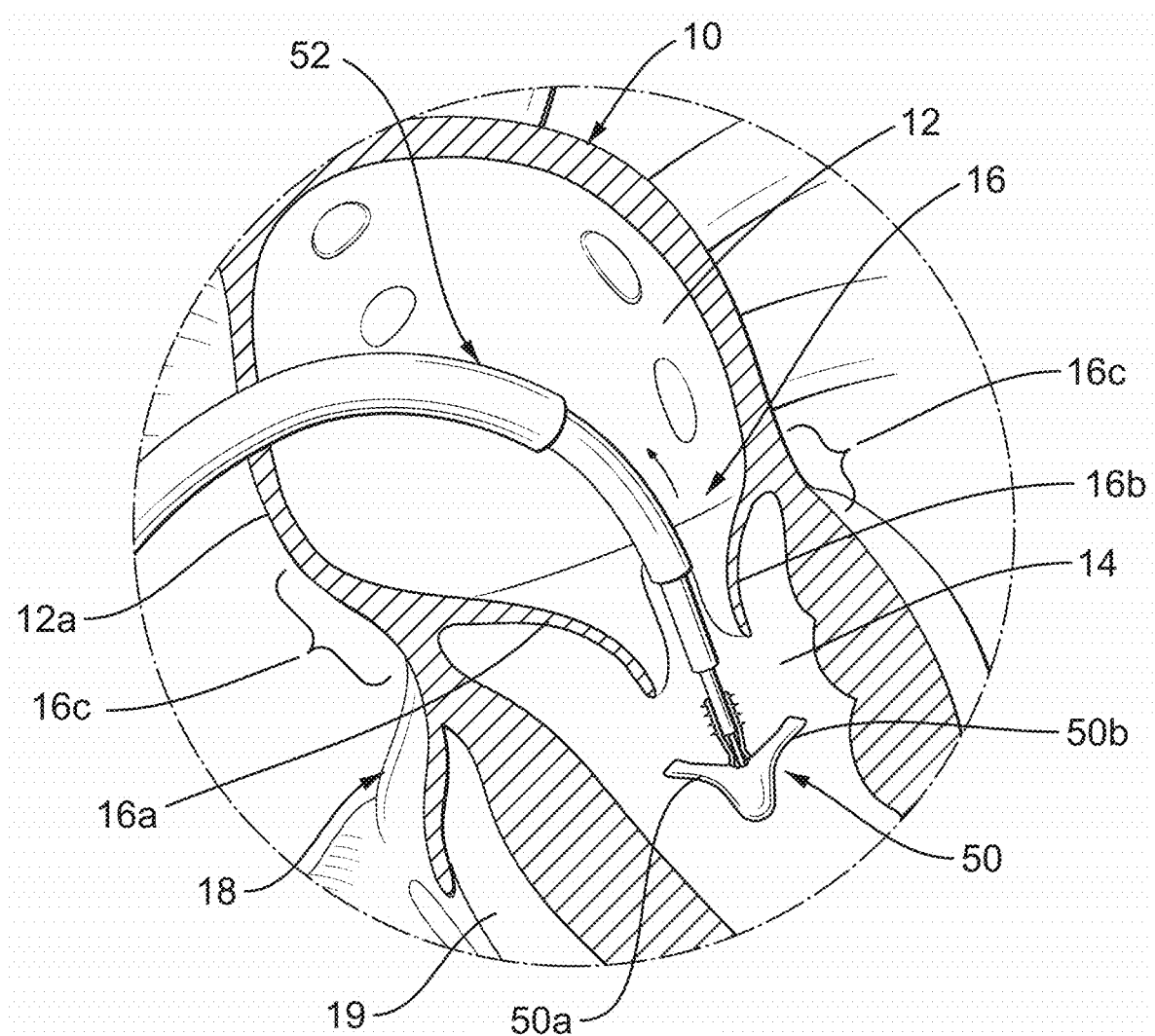
FIG. 5A is a schematic perspective view, partially sectioned similar to FIG. 1A, but illustrating a catheter-based or transcatheter delivery and implantation system constructed in accordance with another embodiment.
Figure 5B:
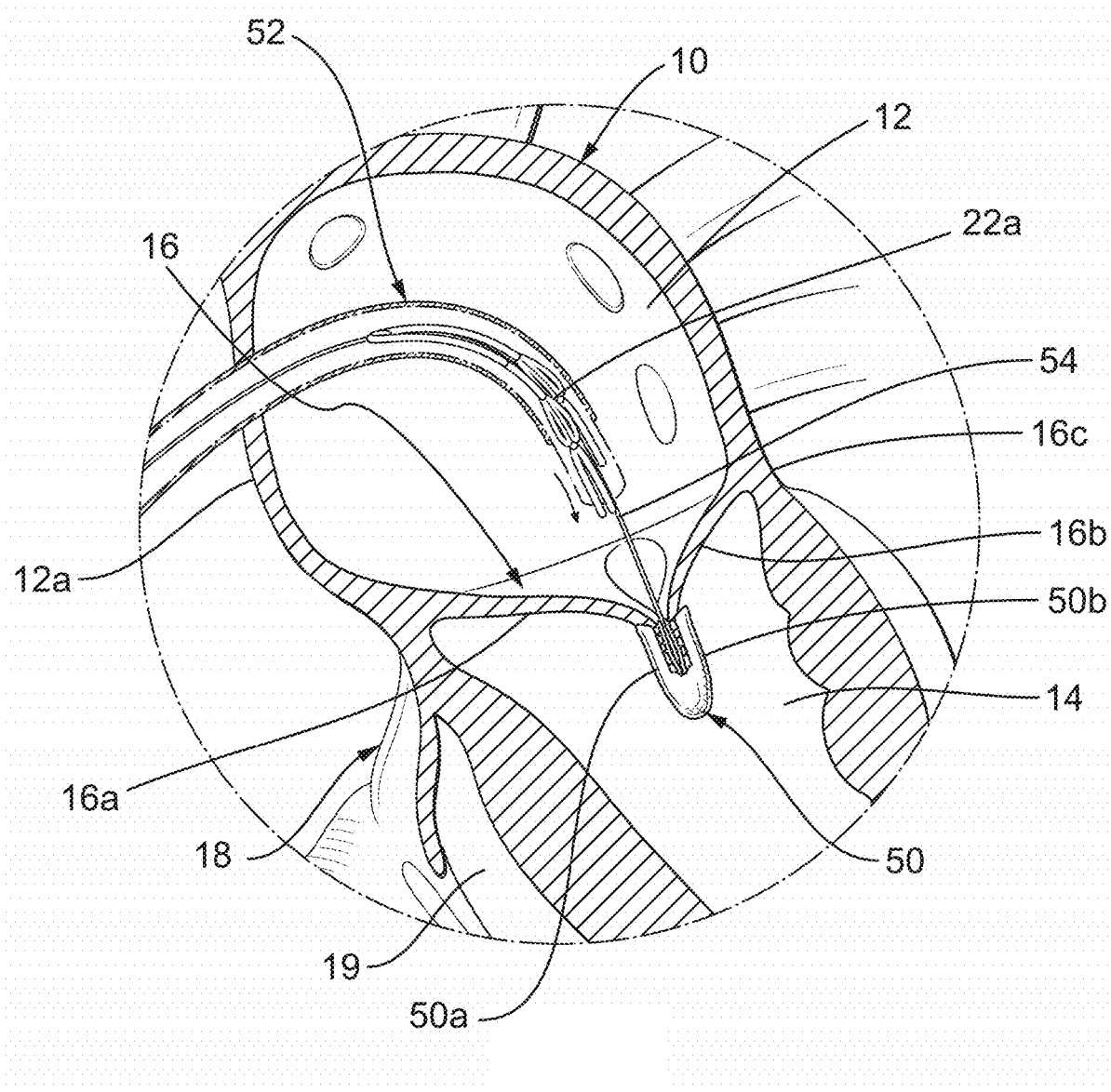
FIG. 5B is a view similar to FIG. 5A, but illustrating a subsequent step in the method, in which the native mitral leaflets have been captured and clipped together.

FIGS. 5A through 5D illustrate another embodiment of a selective occlusion device 22a. As previously stated, all like reference numerals between the various embodiments and figures refer to like structure and function except to the extent described herein. Some reference numerals will have a suffix modification such as a letter (e.g., "22a"), or a prime mark (e.g., 90'), indicating a modification to the like structure which will be discussed and/or apparent from a review of the drawings. To be more concise, redundant descriptions of like structure and function between the various figures will not be made or will be kept to a minimum. This embodiment is particularly suited to achieve beneficial effects for those mitral valve repairs involving clipping or otherwise securing one native leaflet margin to another. It will be appreciated, though, that clips or other anchors (herein generically referred to as clip structures) may be applied to only one leaflet margin, and more than one clip or anchor may be used. Often, mitral valve repair is made with a clip structure 50 having first and second clip elements 50a, 50b movable toward each other from an open condition to a closed position. The clip structure 50 is typically applied in a transcatheter procedure using a suitable catheter assembly 52. A representative and illustrative clip structure 50 is shown in these figures for clipping together margins of the native leaflets 16a, 16b near a central location of each margin. The beginning of the procedure is shown in FIG. 5A with the catheter assembly 52 directed transeptally into the left atrium 12 through the inter-atrial septum 12a and into the mitral valve 16 and to the left ventricle 14. A portion of the margin of each leaflet 16a, 16b is captured by the clip structure 50 and then clipped and firmly secured together as shown in FIG. 5B. At least one of the elements 50a, 50b moves toward the other in a clipping or clamping action to change from an open condition to a closed condition. A wire, suture or other tensile member or connector 54 is coupled to the clip structure 50. At or near the end of the clipping step of the method, a selective occlusion device 22a in the form of a frame structure 30a and flexible membrane 44a (FIG. 5D) is introduced through the catheter or catheters 52 in a manner similar to the method described above with respect to the first embodiment. The selective occlusion device 22a is guided by the suture, wire or other tensile member 54 affixed and extending from the clip structure 50.

Figure 5C:
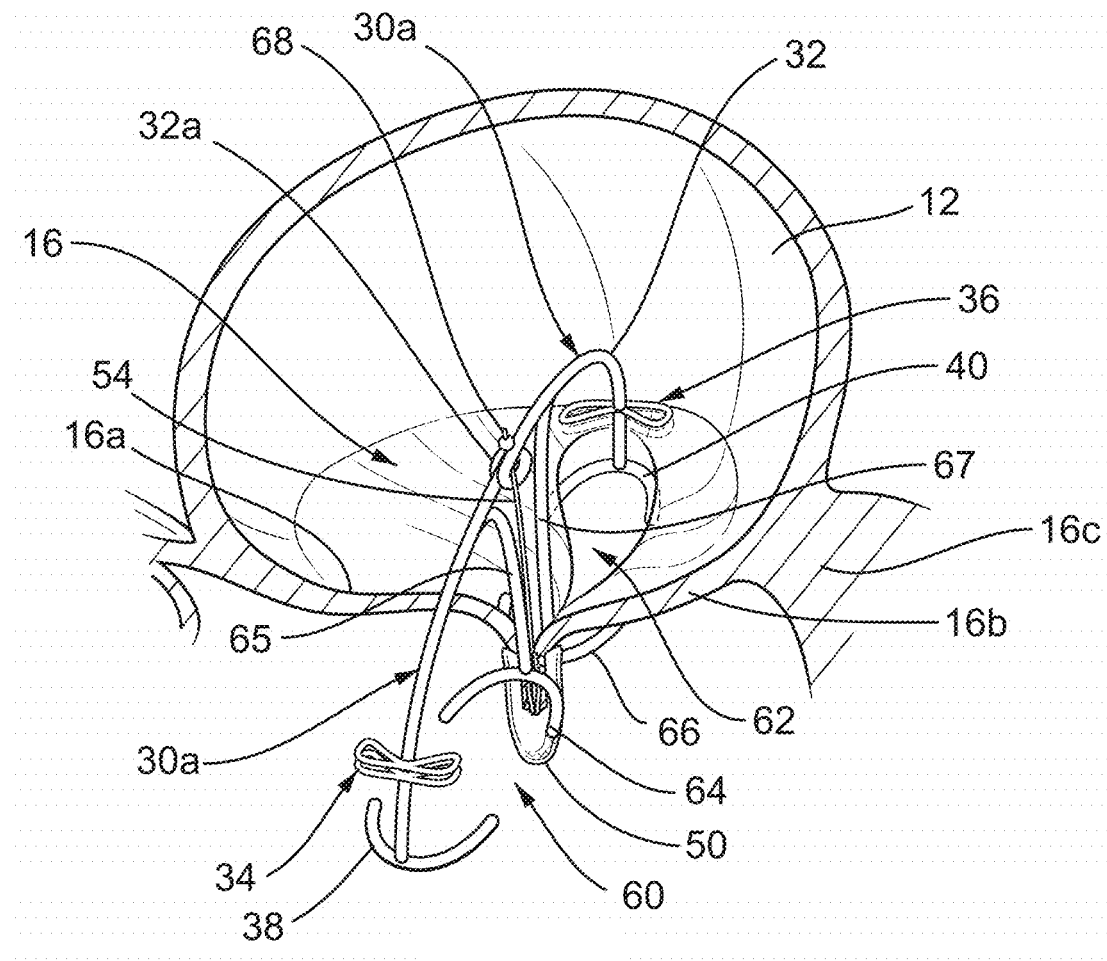
FIG. 5C is a sectional view similar to FIGS. 5A and 5B, but illustrating the frame of the selective occlusion device implanted and attached to the clip structure, with the flexible membrane removed for clarity.
Figure 5D:
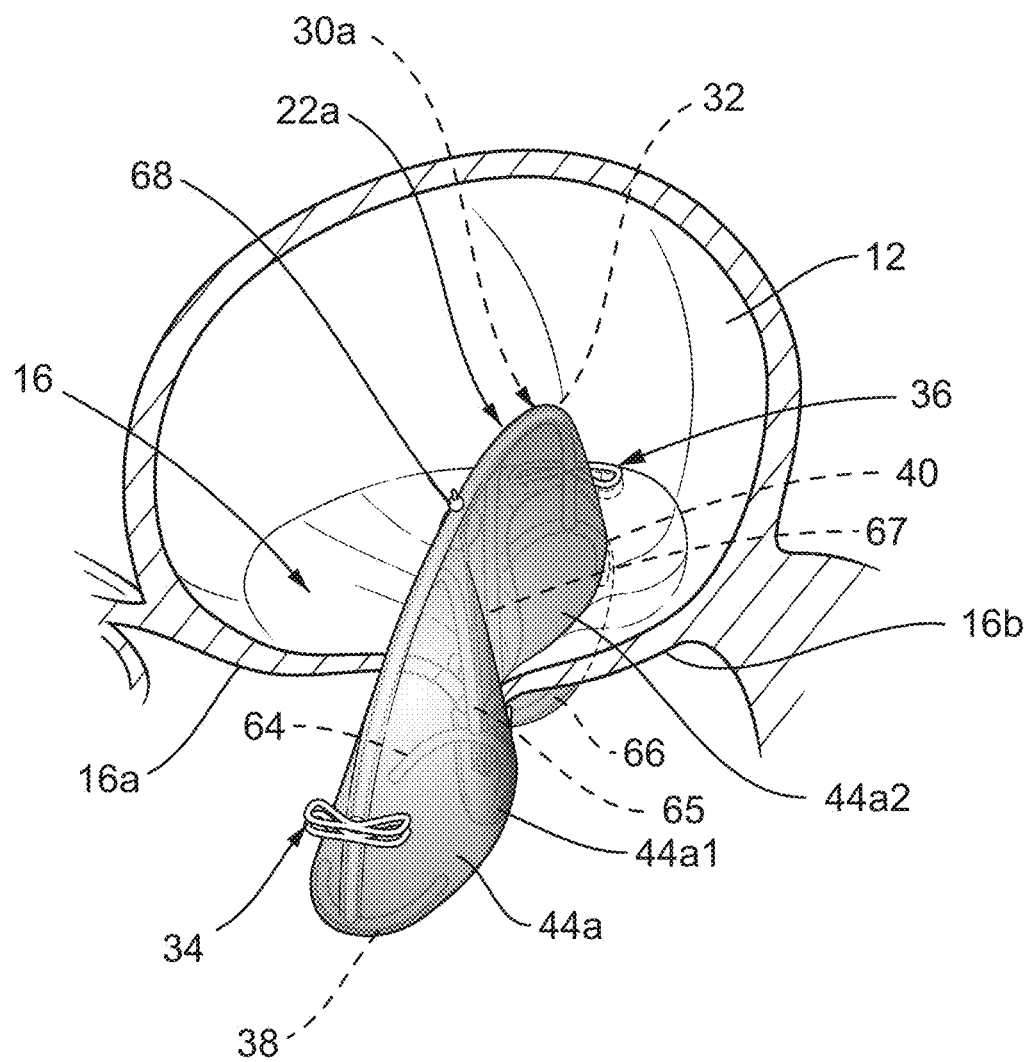
FIG. 5D is a view similar to FIG. 5C, but illustrating the flexible membrane of the device in place on the frame structure.

As further shown in FIG. 5C, this embodiment of the device 30a, 44a includes two sections 60, 62. This embodiment advantageously utilizes the clip structure 50 as an anchoring mechanism for assisting with securing the device 30a, 44a in place and implanted as a selective occlusion device 22a in the native mitral valve 16. The two sections 60, 62 are employed in a manner described above in connection with the single section embodiment of the device 30, 44. As will be appreciated from a review of FIGS. 5C and 5D, a modified frame structure 30a is employed to support a modified flexible membrane 44a. More specifically, the flexible membrane 44a includes corresponding sections 44a1 and 44a2. These may be formed from one or more distinct pieces of membrane material. In addition, third and fourth membrane support members 64, 66 are provided to support the flexible membrane sections 44a1 and 44a2 in manners similar and analogous to the manner that support members 38, 40 support and function in the first illustrative embodiment discussed above. An arc-shaped frame member 32 is shown similar to the first embodiment spanning across the native valve 16. Vertical support members 65, 67 extend from the frame member 32 and couple with the membrane support members 64, 66. As another option, the frame member 32 may be eliminated and the vertical members 65, 67 or other structure could be joined together in the central region of the device 22a.

As further shown best in FIG. 5C, the suture or wire 54 couples the clip structure 50 to the frame structure 30a, such as by using a crimp element or other securement 68 generally at hinge 32a. It will be appreciated that other securement methods and structures may be used instead to secure the clip structure 50 to the frame structure 30*a*. The clip structure 50 and the frame structure 30*a* may take other forms than the illustrative forms shown and described herein. Use of the clip structure 50 securing the frame structure 30*a* in addition to the non-penetrating and/or other connectors such as generally at the native annulus 16*c* provides for an overall secure implant. The clip structure 50 and one or more annulus connectors will provide opposing forces that firmly secure the frame structure 30*a* and flexible membrane 44*a* generally therebetween. The two separate selective occlusion or flow control sections 44*a*1, 44*a*2 are separated from each other by the clip structure 50. The attachment of the selective occlusion device 22*a* to the native mitral valve 16 may be a direct connection between the flexible membrane 44*a* and the native leaflets 16*a*, 16*b* (see below). Another option is that instead of the single arch-type frame member 32, the two side-by-side sections 60, 62 of the frame structure 30*a* may be otherwise coupled together near the center of the selective occlusion device 22*a* to avoid the need for a continuous frame member 32 spanning across the native mitral valve 16. Still further modifications are possible, while retaining advantages of a clip structure used in combination with a selective occlusion device. For example, the selective occlusion device may be configured as a frame structure and flexible membrane affixed around a continuous perimeter portion of the frame structure.

Figure 6A:
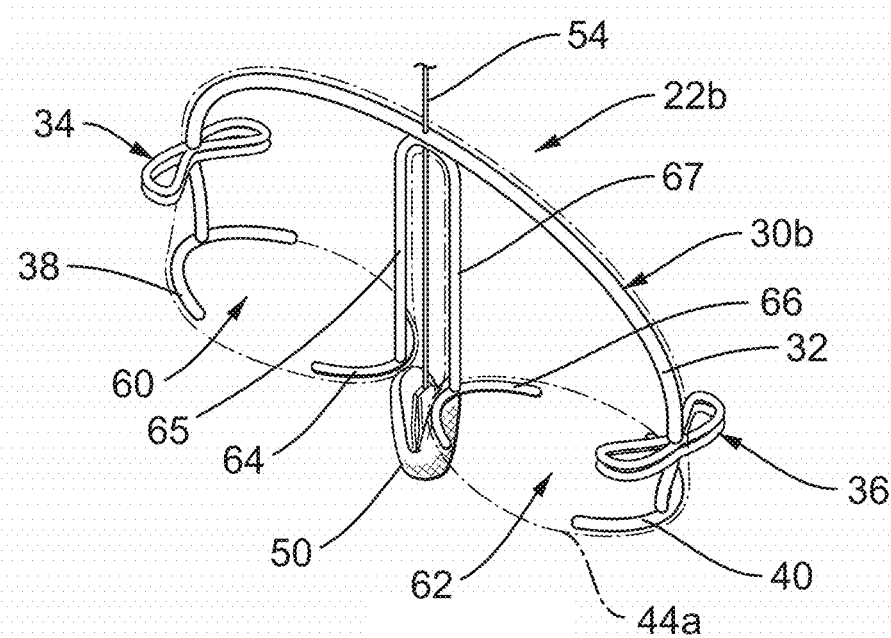
FIG. 6A is a perspective view of the frame structure and attached clip structure shown in FIGS. 5A through 5C.
Figure 6B:
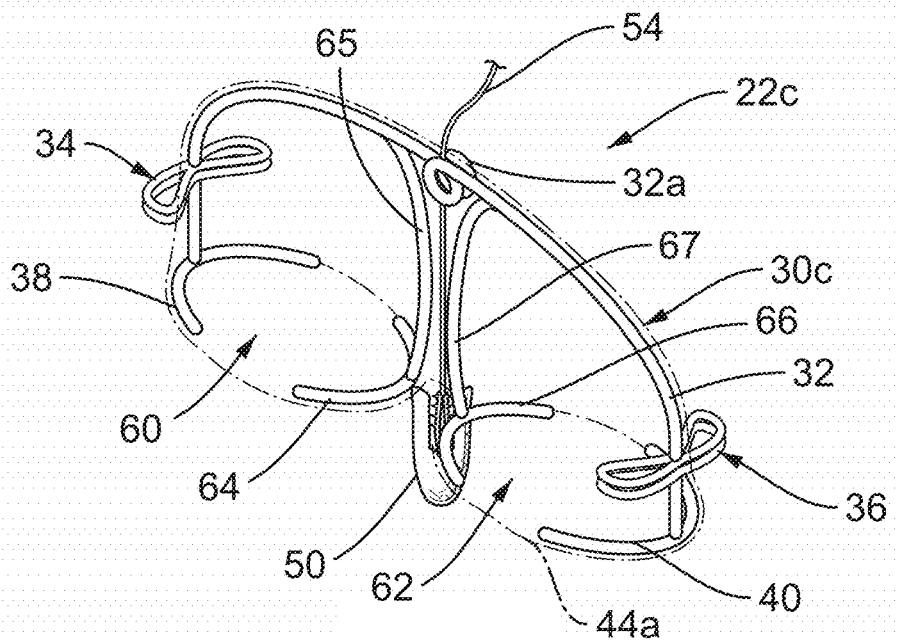
FIG. 6B is a perspective view similar to FIG. 6A, but illustrating another embodiment of a collapsible and expandable frame structure.

FIGS. 6A and 6B illustrate additional embodiments of selective occlusion devices 22*b* and 22*c*. In these figures the flexible membrane 44*a* is shown in broken lines so that the respective frame structures 30*b*, 30*c* are more clearly shown. In the illustrative embodiment of FIG. 6A, the central hinge has been eliminated and the suture or wire 54 extends directly through the frame member 32. As with all embodiments, the devices 22*b*, 22*c* and any associated components, such as the frame structures 30*b*, 30*c*, may be made flexible enough and foldable into a collapsed condition for catheter delivery purposes. Again, a crimp element (not shown) or any other fixation manner may be used to secure the wire or suture 54 in tension against the frame structure 30*b*, 30*c*. FIG. 6B illustrates an embodiment of the selective occlusion device 22*c* slightly different from the embodiment of FIG. 6A in that the flexible membrane 44*a*, shown in broken lines, is folded inwardly at the region of the clip structure 50. As shown in FIG. 6A, and as one additional option, the flexible membrane 44*a* may be more distinctly attached to the frame members as shown by the broken lines extending upwardly against the vertical frame members 65, 67.

Figure 7A:
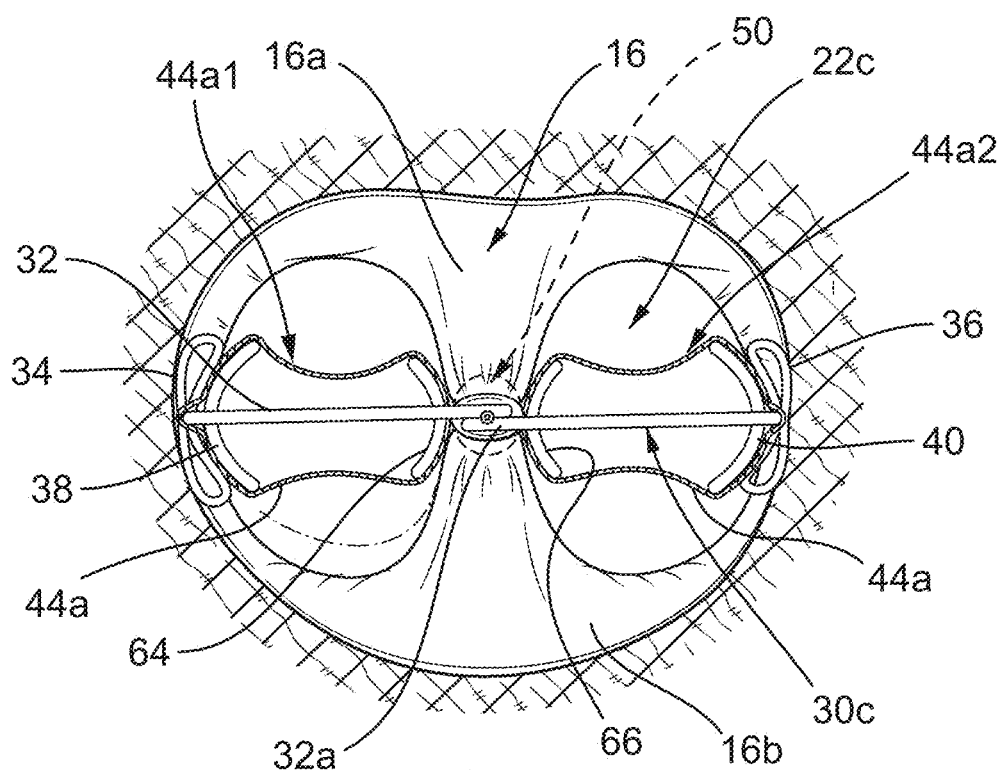
FIG. 7A is a cross sectional view of the native mitral valve and selective occlusion device of FIG. 6B, with the heart in the diastole phase.
Figure 7B:
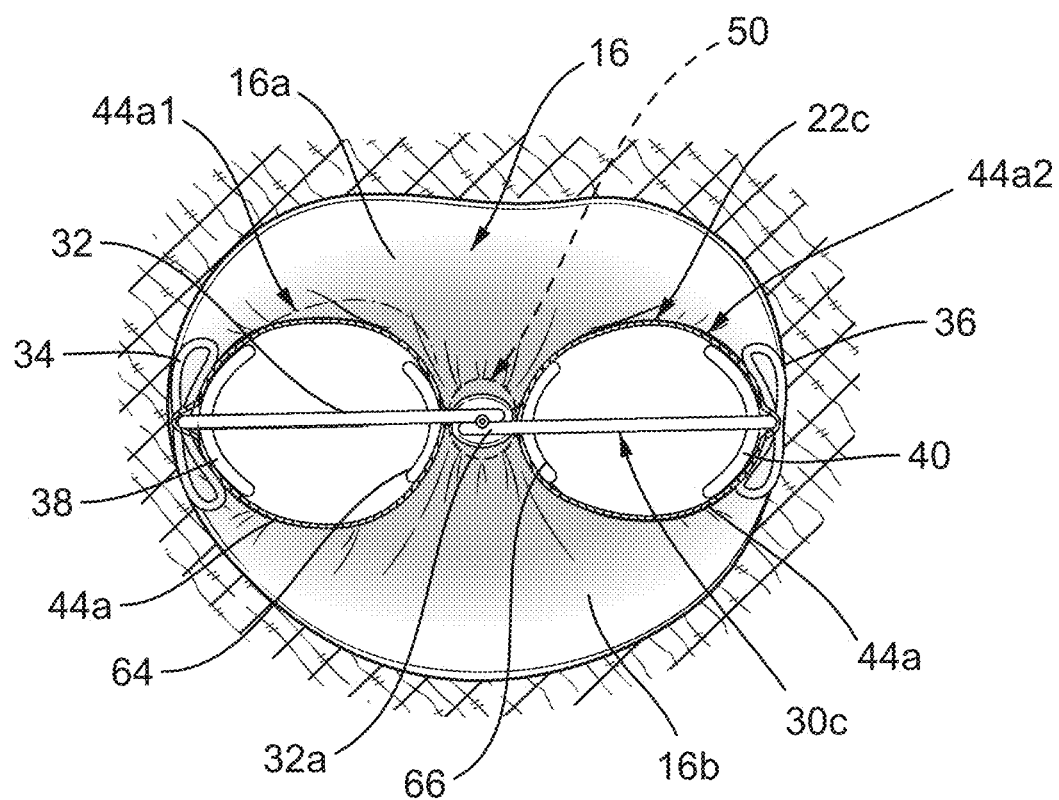
FIG. 7B is a cross sectional view similar to FIG. 7A, but illustrating the selective occlusion device and the mitral valve when the heart is in the systole phase.

FIGS. 7A and 7B are top views illustrating selective occlusion device 22*c*, such as shown in FIG. 6B having separate sections 44*a*1 and 44*a*2 secured in place and implanted within a native mitral valve 16. FIG. 7A shows the selective occlusion device 22*c* when the heart cycle is in diastole, and FIG. 7B shows the selective occlusion device 22*c* when the heart cycle is in systole. The function of a multi-section apparatus, such as with devices 22*a*, 22*b*, 22*c*, is similar to the function of the single section selective occlusion device 22 discussed above in connection with the first illustrative embodiment, except that with the native mitral valve itself separated into two sections by the clip structure 50, the separate flexible membrane sections 44*a*1 and 44*a*2 independently function to contract or collapse in diastole (FIG. 7A) and billow, expand or inflate outwardly in systole (FIG. 7B) due to the forceful introduction of blood flow when the heart cycle is in systole. The effect or result is similar to that described above in connection with, for example, FIGS. 3A and 3B, but with the dual effect of correcting any misalignment or lack of coaptation between the native mitral leaflets 16*a*, 16*b* on each side of the clip structure 50. In this manner, blood flow is allowed in diastole as shown in FIG. 7A past the native mitral leaflets 16*a*, 16*b* which have spread or expanded outwardly and also past the two section flexible membrane 44*a* which has collapsed inwardly or away from the native mitral leaflets 16*a*, 16*b*. Reverse or regurgitated blood flow is at least reduced, if not reduced to essentially zero (prevented), during systole as the flexible membrane 44*a* expands or inflates to contact or engage the native mitral leaflets 16*a*, 16*b* creating a fluid seal.

Figure 8:
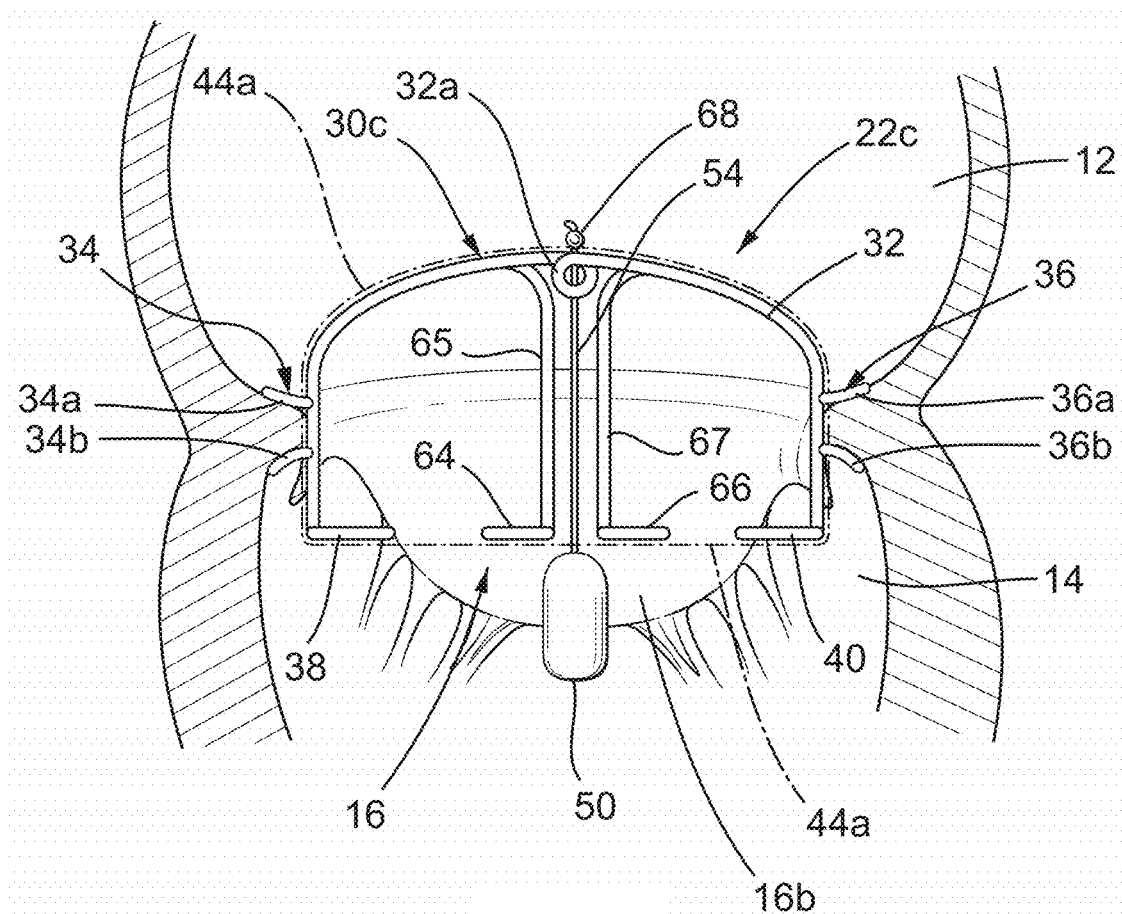
FIG. 8 is a side view with the heart in cross-section at the location of the native mitral valve, illustrating the selective occlusion device, with the membrane in broken lines for clarity, and the device implanted.

FIG. 8 shows a side view of the selective occlusion device 22*c* shown in FIG. 7B, but with the flexible membrane 44*a* shown in broken lines for clarity. The selective occlusion device 22*c* is securely implanted in the mitral valve 16 between annulus connectors 34, 36 generally at an upper location and a clip structure 50 at a lower location. Again, different connector and/or clip configurations may be used than those shown and described, and different numbers of connectors and clip structures may be used. The clip structure or structures may be secured to each leaflet 16*a*, 16*b* simultaneously as shown, or may be secured separately to a single leaflet 16*a* and/or 16*b*. Although the tensile member 54 is shown to have a particular length to connect between the clip structure 50 and the frame member 32, a tensile member or other type of connection of any necessary longer or shorter extent may be used instead. In some cases, the clip structure 50 may be directly affixed to the frame structure 30.

Figure 9:
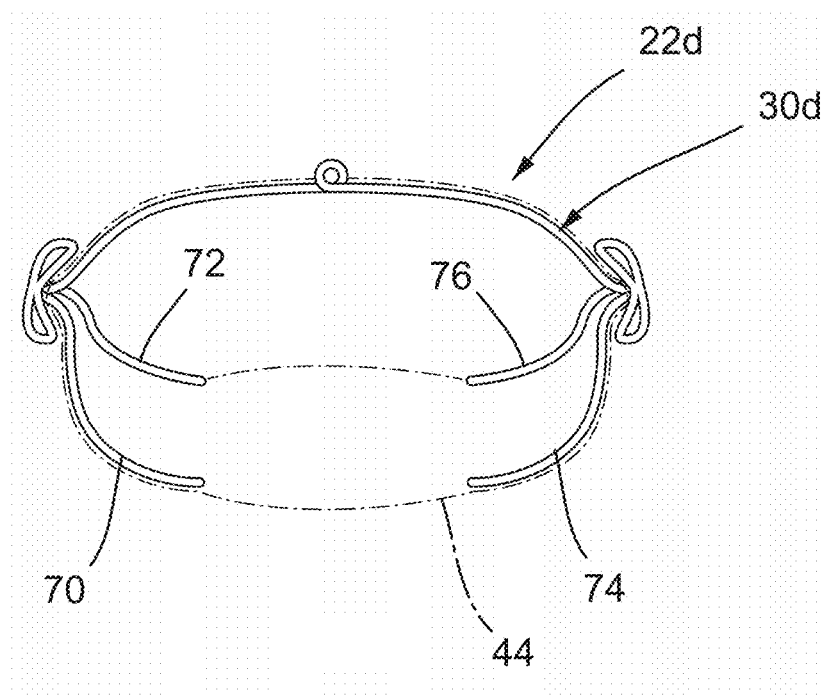
FIG. 9 is a perspective view illustrating another embodiment of a selective occlusion device, showing the frame structure in solid lines and the flexible membrane in broken lines for clarity.

FIG. 9 illustrates a selective occlusion device 22*d* constructed according to an illustrative embodiment, in which an alternatively configured frame structure 30*d* is used and coupled with a flexible membrane 44 (shown in broken lines for clarity. Particularly, lower supporting members 70, 72, 74, 76 have a different configuration for guiding the shape of the flexible membrane 44. The flexible membrane 44 may be securely attached to the lower supporting members 70, 72, 74, 76 along their entire lengths, or along a portion of their lengths, or not at all if they are otherwise held in place during diastole in a suitable manner. The lower margins of the flexible membrane 44 are allowed to billow or expand outwardly and may be detached from the lower supporting members 70, 72, 74, 76 along at least substantial portions to allow this expanding or billowing action to take place. In addition, the entire frame structure 30*d* and/or only the lower supporting members 70, 72, 74, 76 may be highly flexible to allow this expansion or billowing action to take place when the heart cycle is in systole, as previously described.

Figure 10A:
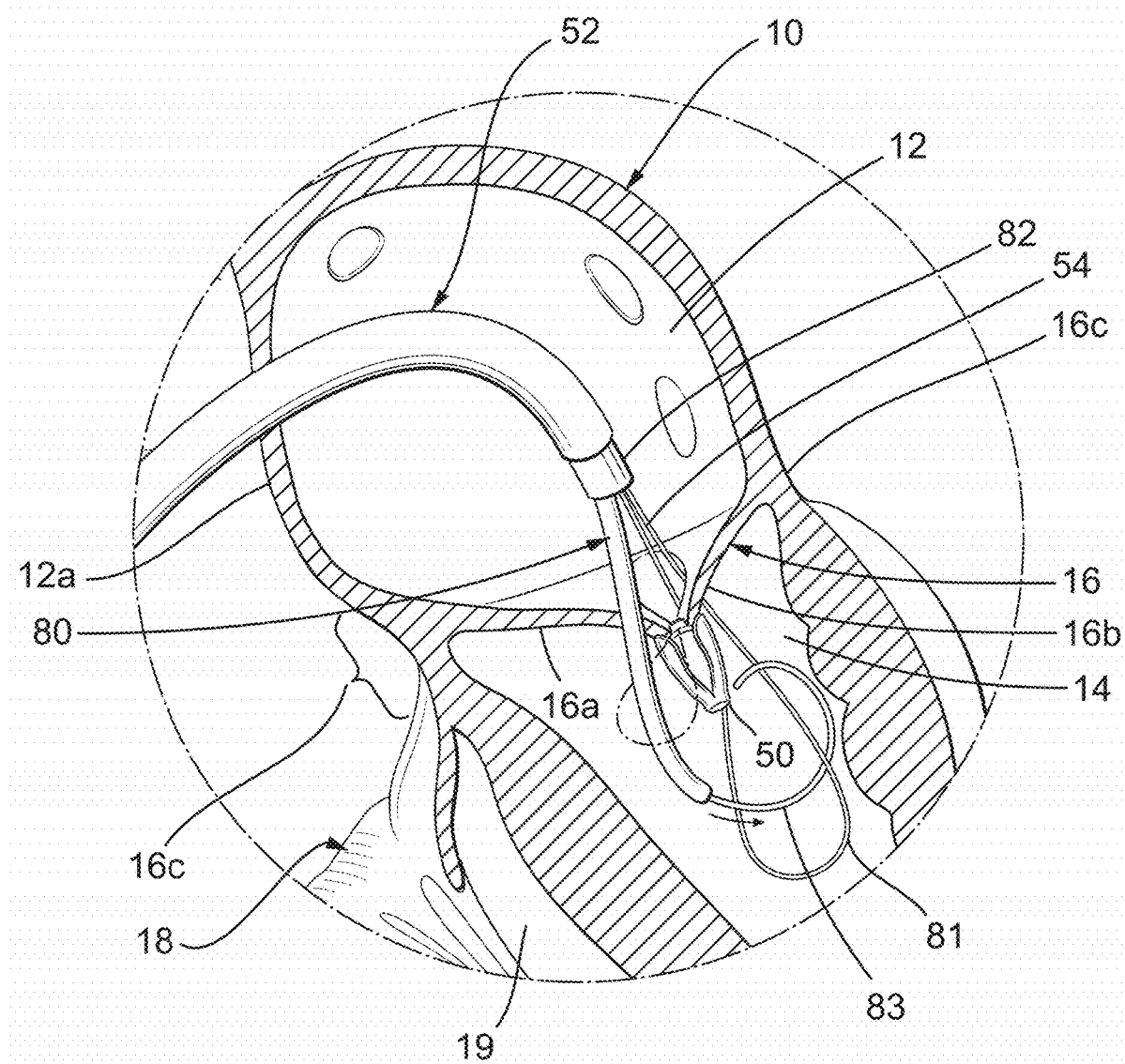
FIG. 10A is a schematic perspective view similar to FIGS. 1A and 5A, but illustrating another embodiment of a catheter-based system for delivering and implanting a selective occlusion device coupled with a pre-installed mitral valve leaflet clip structure.
Figure 10B:
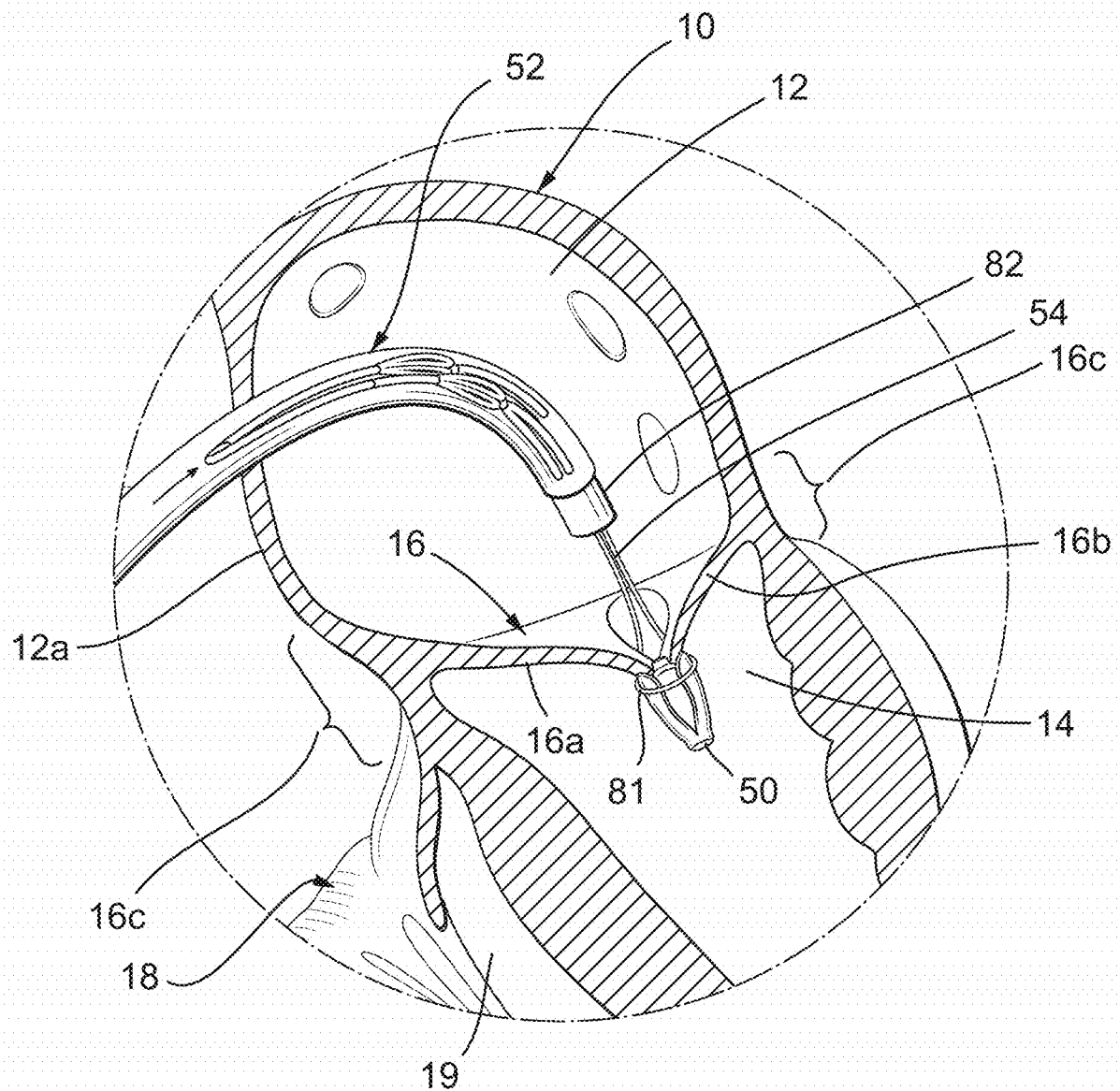
FIG. 10B is a view similar to FIG. 10A, but illustrating a subsequent step during the method.
Figure 10C:
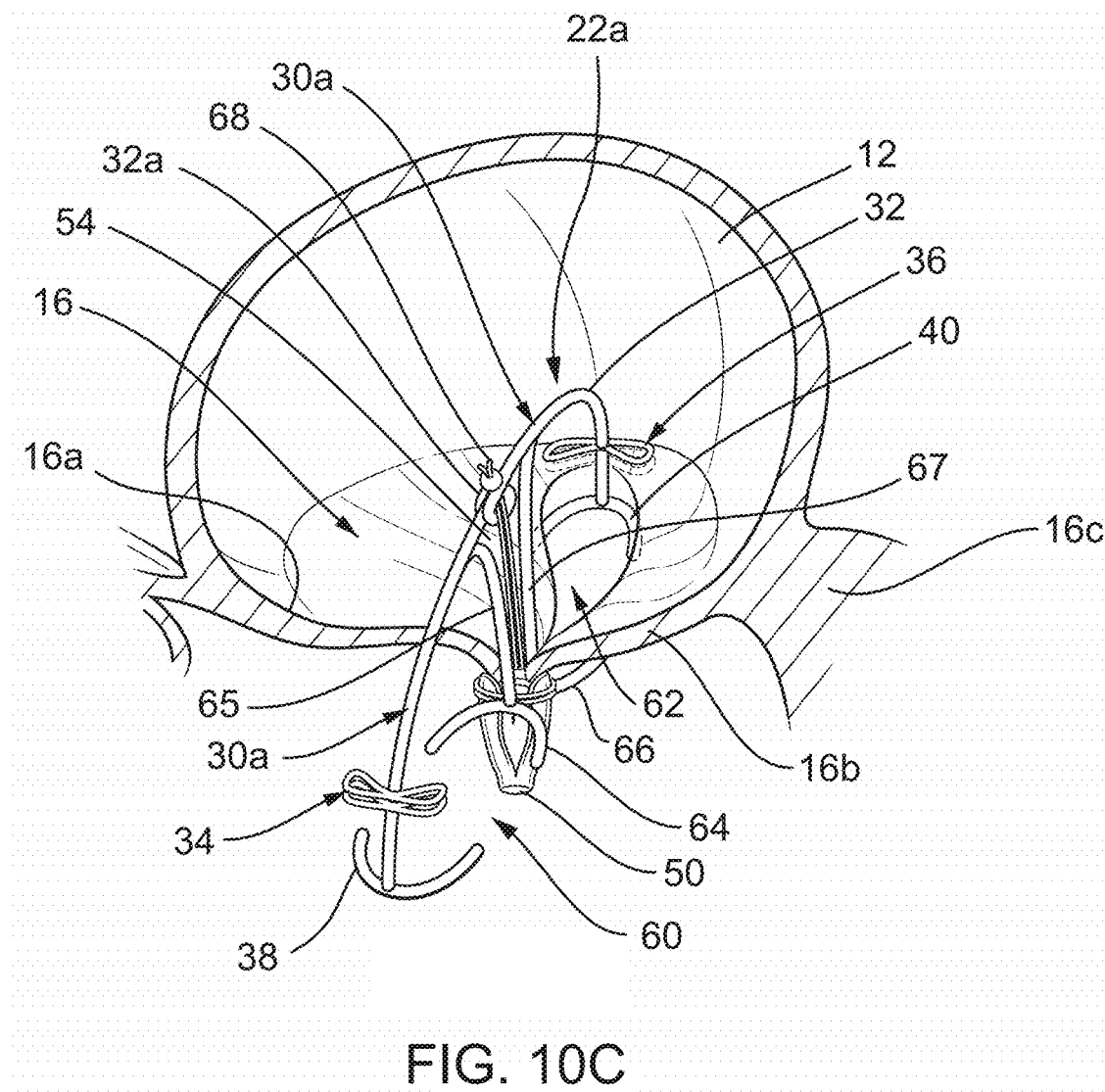
FIG. 10C is a perspective view, with the heart sectioned at the native mitral valve, illustrating the implantation of the selective occlusion device, but with the flexible membrane removed for clarity.

FIGS. 10A, 10B and 10C show another illustrative embodiment in which a transcatheter system 52 is used and, specifically, a clip structure capturing device 80 is used to help secure the selective occlusion device 22*a* in place. This may be particularly useful when applying a selective occlusion device such as according to the present disclosure to a previously implanted mitral clip structure 50. The clip structure 50 may be of any type or configuration. In cases where the clip structure 50 has failed to properly repair the mitral valve 16, or the mitral valve function has degraded over time, despite the clip repair procedure, this embodiment assists with the capturing of the previously implanted clip structure 50 and implantation of a selective occlusion device, such as frame structure 30*a* and flexible membrane 44*a*. In this regard, and as shown in FIGS. 10A and 10B, a lasso or suture loop device 81 is deployed from a catheter 82 and captures the clip structure 50 with assistance from a guide device 83. The suture, wire or other tensile member 54 that extends upwardly through the mitral valve 16 may be a part of the suture loop device 81 in this embodiment and may then be used as generally described above to guide and securely affix selective occlusion device 22*a*, to the clip structure 50, as shown in FIG. 10C. For clarity, the flexible membrane 44*a* has not been shown in FIG. 10C.

Figure 11A:
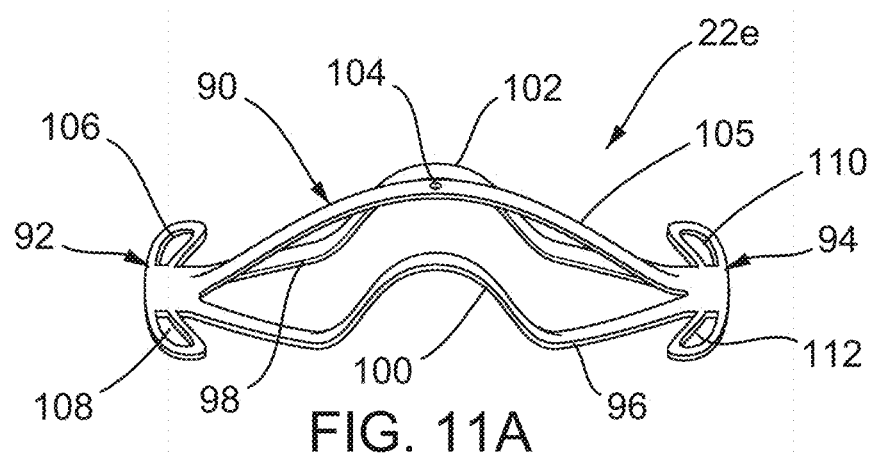
FIG. 11A is a perspective view showing another alternative embodiment of a selective occlusion device with the flexible membrane removed for clarity.
Figure 11B:
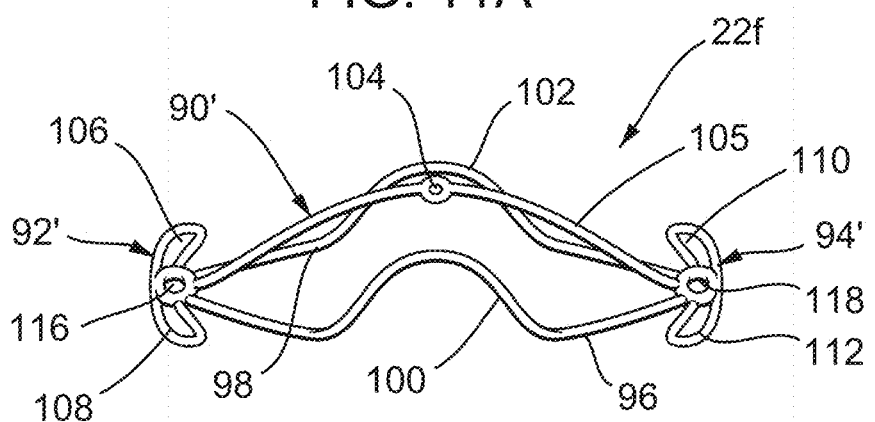
FIG. 11B is a perspective view showing another alternative embodiment of a selective occlusion device with the flexible membrane removed for clarity.
Figure 11C:
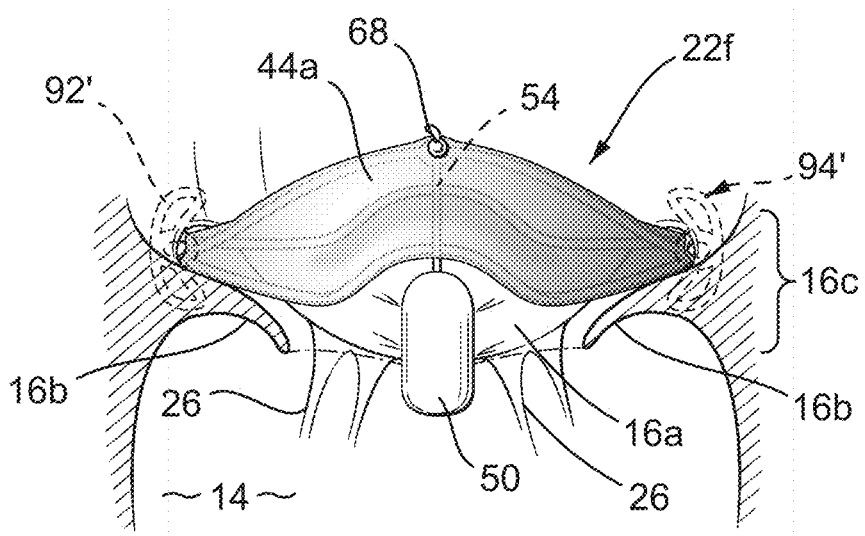
FIG. 11C is a front top perspective view of the device of FIG. 11A or 11B implanted in the native mitral valve.
Figure 11D:
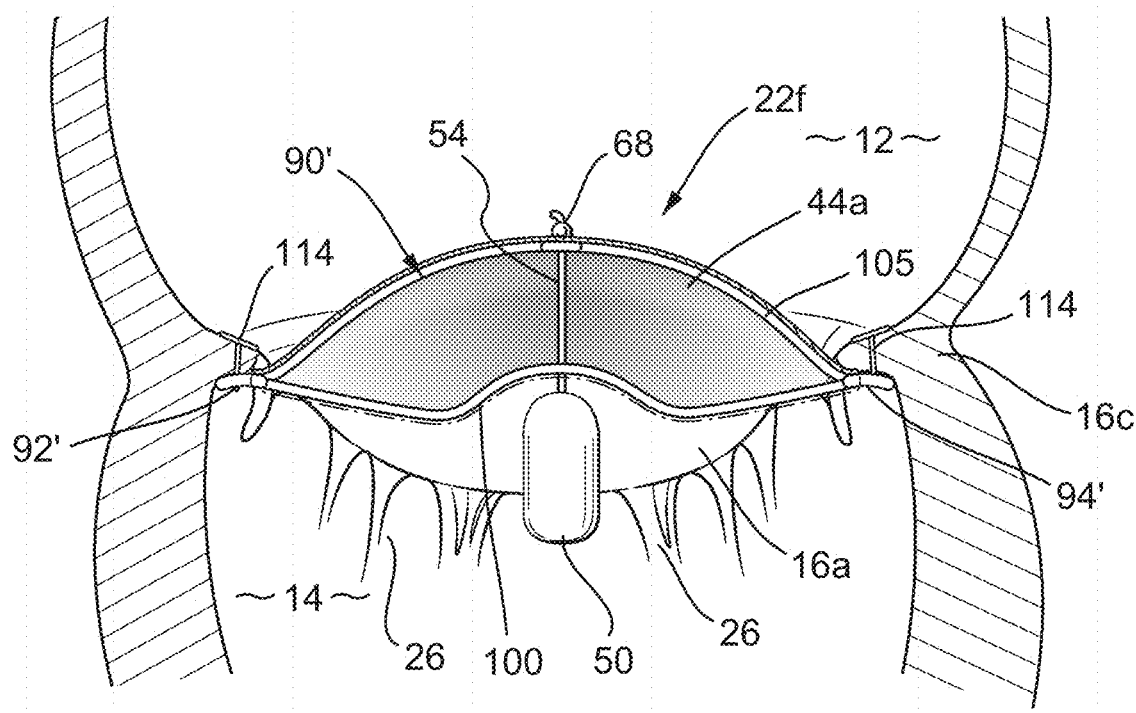
FIG. 11D is a front view of the device in FIGS. 11A through 11C.
Figure 11E:
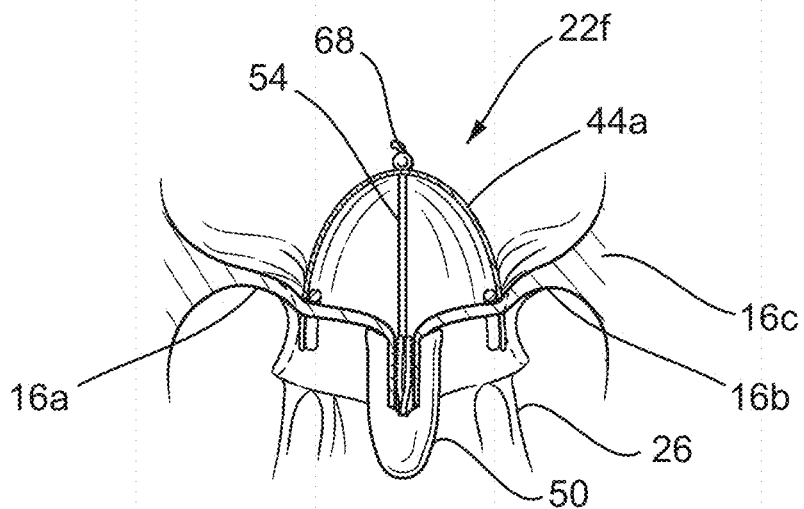
FIG. 11E is a transverse cross section of FIG. 11D.

FIGS. 11A and 11B illustrate two additional embodiments of selective occlusion devices 22*e*, 22*f*, without showing the flexible membranes, that may be used to prevent blood flow regurgitation through a heart valve such as, by way of example, the mitral valve 16. In these embodiments, a flexible membrane 44*a* (FIGS. 11C through 11E) may be secured over a frame structure 90, 90' from one end to the other, such as between two non-penetrating annulus connectors or, in other embodiments, penetrating connector portions 92, 94, 92', 94'. Advantageously, there are two spaced apart elongate frame members 96, 98 extending between the connectors 92, 94, 92', 94', each having an upward bend or hump 100, 102 creating a recessed space. As shown in FIG. 11C the flexible membrane 44*a* is carried on this frame structure 90, 90' and may be secured to the frame members 96, 98 along all or some of the lengths thereof. This can leave a desired portion of the flexible membrane 44*a* at the lower margin of the frame structures 90, 90' unsecured and able to expand or billow in outward direction during systole, generally as described above in prior described embodiments or in later described embodiments. This outward expansion or billowing action will allow the flexible membrane 44*a* to better contact or engage the natural leaflet tissue during systole to prevent regurgitation of blood flow. This will also allow for more exchange of blood beneath or within the flexible membrane to prevent blood stagnation and the resulting possibility of clotting which may embolize and cause stroke or other complications. The humps 100, 102 in each of the lower, spaced apart support members 96, 98 accommodate the clip structure 50 and generally receive that portion of the mitral valve 16 fastened together at the A2/P2 junction. A central connection element, such as a hole 104, is provided in a central frame member 105 and allows a wire, suture or other tensile member 54 to attach the frame structure 90, 90' to the clip structure 50. The central frame member connects the annulus connectors 92, 94 and 92', 94' together and arches over and across the mitral valve 16 in a manner similar to frame member 32. Suitable configurations of the frame structure 90, 90' may be used, such as any of those previously described, for accommodating one or more clip structures and forming a plurality of separate flexible membrane sections, for example, with one section on each side of a clip structure 50. FIGS. 11A and 11B also show another way of attaching a frame structure generally at the native annulus 16*c* with one or more holes 106, 108, 110, 112 to engage with a suitable fixation element or anchor 114 (FIG. 11D). The embodiment of FIG. 11D includes two additional fixation holes 116, 118 for receiving fasteners. In some embodiments such as shown in FIG. 11D, penetrating anchors may be used, such as rivets, T-bars, pledgets, or other fixation elements, although the benefits of non-penetrating connectors in accordance with this disclosure would be desirable, such as for purposes of allowing self-adjustment and reduced tissue damage.

Figure 12A:
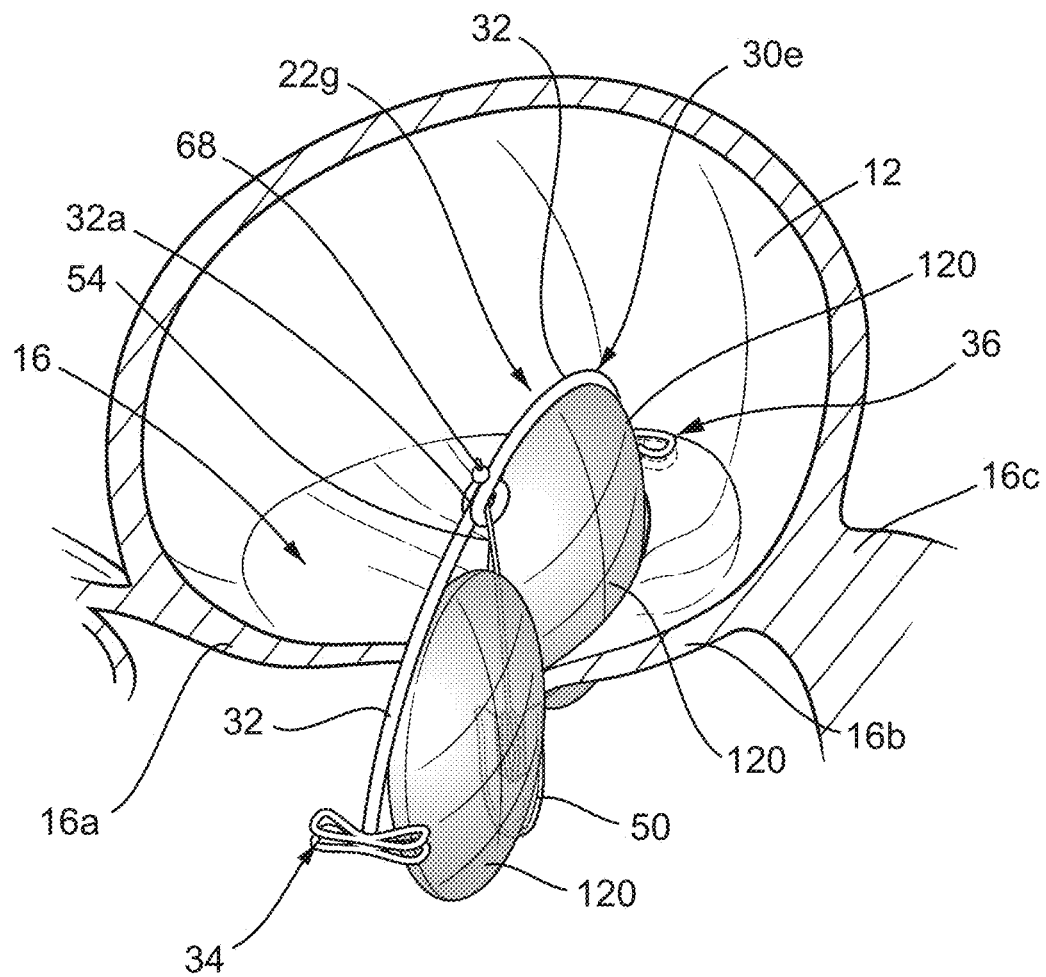
FIG. 12A is a perspective view of another alternative embodiment of a selective occlusion device implanted in the native mitral valve, which is shown in cross-section similar to previous figures.
Figure 12B:
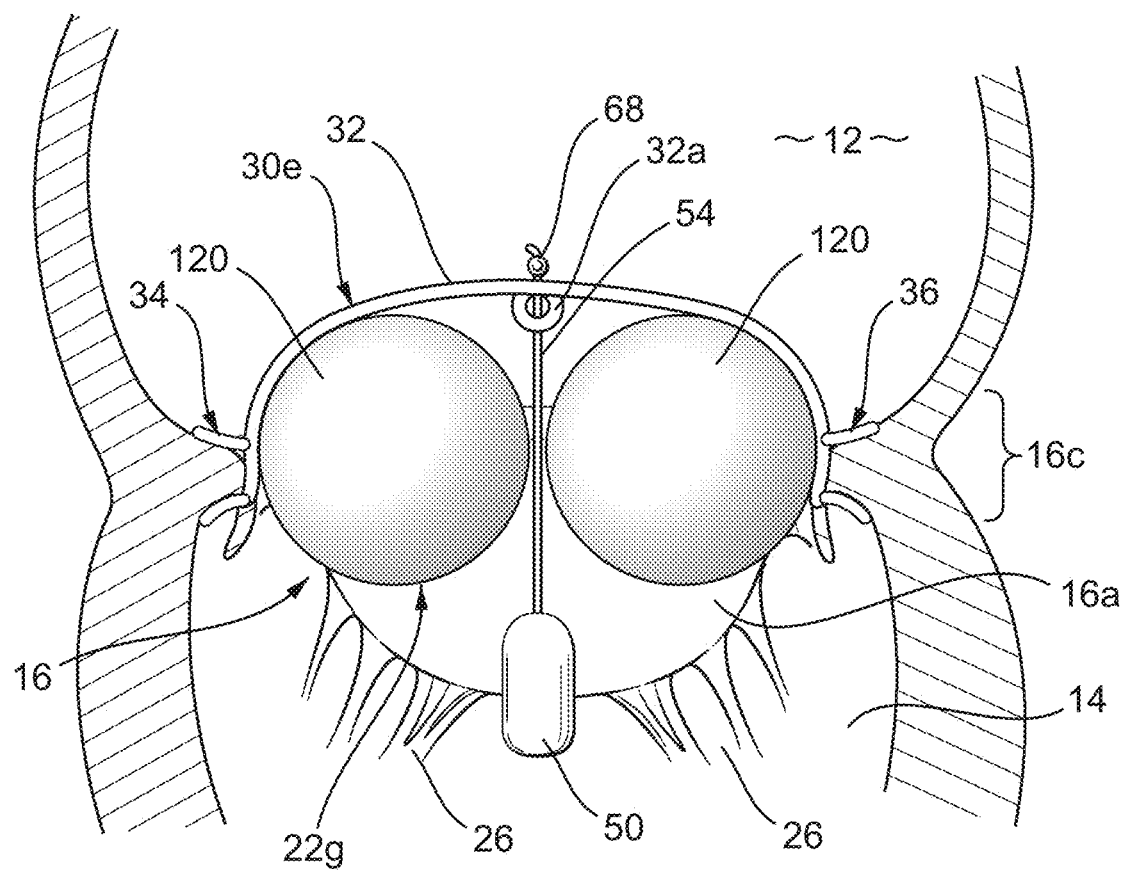
FIG. 12B is a cross-sectional view of the heart, taken at the native mitral valve, and showing the selective occlusion device of FIG. 12A in side elevation.
Figure 13A:
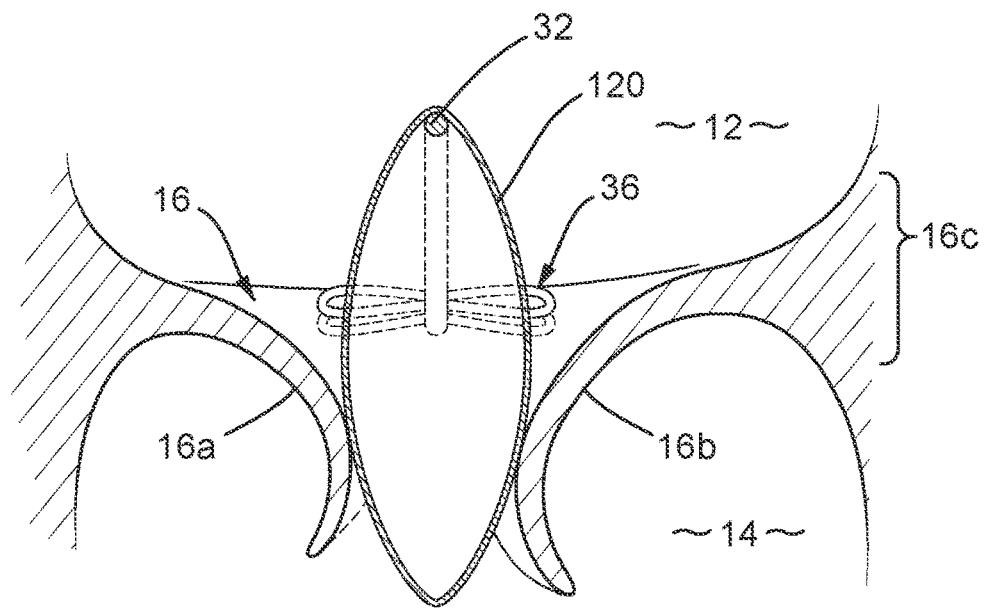
FIG. 13A is a transverse cross-sectional view taken through the mitral valve and generally through one of the selective occlusion elements of FIGS. 12A through 12D, to show sealing during systole.
Figure 13B:
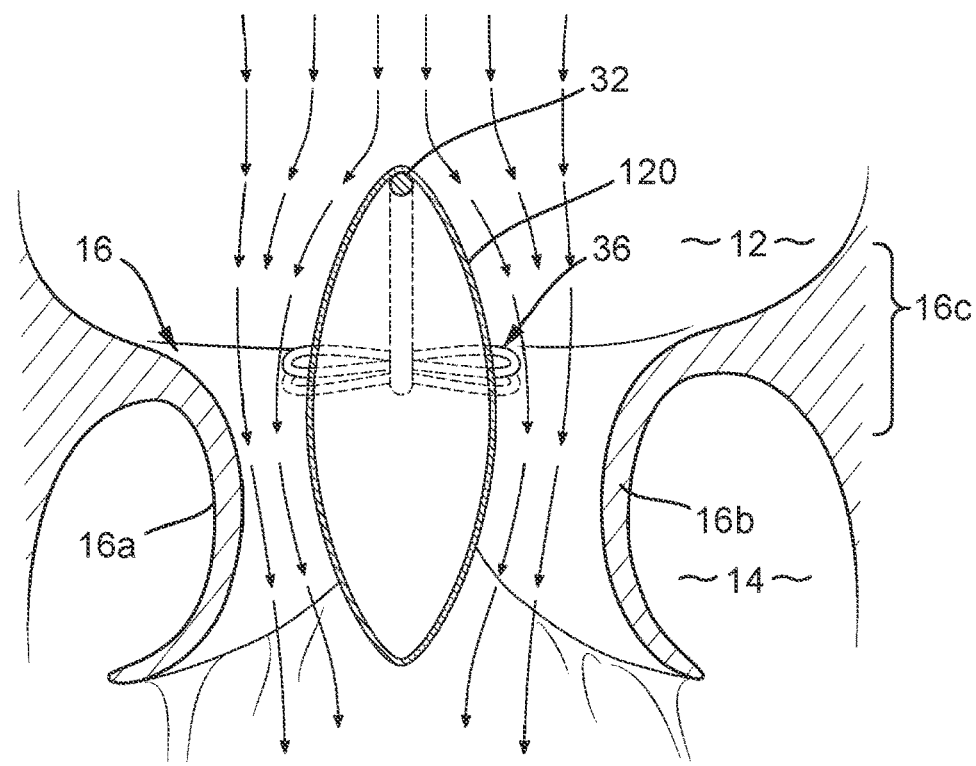
FIG. 13B is a view similar to FIG. 13A, but showing the selective occlusion element and the mitral valve when the heart is in the diastole phase.

FIGS. 12A and 12B illustrate another illustrative embodiment of a selective occlusion device 22*g*. Rather than employing a flexible membrane, this apparatus includes at least one rigid occlusion element 120. This embodiment is more specifically configured to operate in conjunction with mitral valve leaflets 16*a*, 16*b* that have been affixed together at a central location along their margins with a clip structure 50 such as a clip structure previously described. Therefore, two selective occlusion elements 120 are provided for reasons analogous to the two section flexible membrane embodiments described herein. The selective occlusion elements 120 are "rigid" in use within the mitral valve 16 in that they are static and need not flex inwardly or outwardly to engage and disengage the native mitral leaflets 16*a*, 16*b* during the systole and diastole portions of the heart cycle. Instead, these disk-shaped elements 120 retain their shape and are sized and located in the native mitral valve 16 such that the native mitral leaflets 16*a*, 16*b* engage the elements 120 during systole and disengage the elements 120 during diastole. This selective or cyclical interaction is shown in FIGS. 13A and 13B, to be described further below. The device 22*g* shown in FIGS. 12A and 12B includes a frame structure 30*e* that is configured to extend generally across the native mitral valve 16, with a frame member 32 and hinge 32*a* as generally described in previous embodiments, along with non-penetrating annulus connectors 34, 36 as also previously described. Further, the clip structure 50 is secured to the frame structure 30*e* with a crimp element 68 and a suture, wire or other tensile member 54, such as in one of the previously described manners. In this way, the first and second rigid, selective occlusion elements 120 are respectively disposed on opposite sides of the native mitral valve 16 and on opposite sides of the clip structure 50 to selectively include the openings in the native mitral valve 16 formed when the clip structure 50 is affixed to each leaflet 16*a*, 16*b* bringing central portions of the two leaflet margins together either in direct contact with each other or in contact with a spacer (not shown) disposed between the movable clip elements. In this embodiment, the frame structure 30*e* is formed with a curved or arch-type frame member 32 configured to extend over the native mitral valve 16 in the left atrium 12.

The selective occlusion device 22*g* is shown when the heart cycle is in systole in FIGS. 12A, 12B and 13A. The native anterior and posterior mitral valve leaflets 16*a*, 16*b* are shown being forced inwardly toward each other. There is no blood leak or regurgitation because the static occlusion elements 120 fill any residual gap between the anterior and posterior leaflets 16*a*, 16*b*. The elements 120 do not need to be of the depicted shape. Any shape of space filling would be sufficient if the gap between the two leaflets 16*a*, 16*b* is filled by the elements 120. The best shape could be determined at least partly by studying the shape of the gap between the native mitral valve leaflets 16*a*, 16*b* in systole after a clip structure 50 has been applied. The optimal shape for the elements 120 for a particular patient anatomy may even be custom manufactured for that patient with rapid manufacturing techniques. Advantages of using rigid/static element(s) 120 include their ability to withstand repeated cycling forces perhaps better than a design that relies on one or more moving valve elements that may be more susceptible to fatigue.

FIG. 12B more particularly shows a cut away view of the mitral valve 16 from commissure to commissure. At the commissures, the anchors or connectors 34, 36 are shown on each side—both above and below the leaflets 16*a*, 16*b*. Centrally, there is a clip structure 50 or other attachment that anchors to the mitral valve leaflets 16*a*, 16*b* either individually or together. A tensile or other connecting member 54 extends up from the clip attachment component 50 and attaches to the frame member 32 which extends across the valve 16 from commissure to commissure.

The frame structure 30*e* can be constructed of a metal material such as stainless steel or Nitinol. Nitinol or other shape memory or super-elastic material may be preferred as this can be collapsed for delivery via a catheter device inside the heart, and then expanded inside the heart for implantation.

The element(s) 120 may be constructed in a number of ways and have various shapes. They could be composed of a frame of metal such as Nitinol that could be collapsed for catheter delivery. The metal frame could be covered by a plastic material or other artificial material like silicone or Teflon or polyurethane. Animal or human pericardium and animal or human heart valve material or any of the materials typically used for heart valve leaflet construction could be used to cover the frame structure 30*e*. A synthetic material or bioengineered material could also be used to cover the frame structure 30*e*.

The inside of the static occlusion elements 120 could be hollow. Or, a bladder or sac could be inside to fill the hollow interior space of the element(s) 120. The bladder could be filled with air or any gas or a liquid such as saline, sterile water, blood, antibiotic or antiseptic fluid, polymer or curable fluid material. The use of a bladder to fill the inside of the element 120 could eliminate the need or reduce the need for a frame associated with the element 120.

The selective occlusion device 22*g* has commissural and leaflet attachments to anchor it in position. It would also be possible to create this apparatus without a leaflet attachment. For example, the attachment could be at the commissures only. It would not be necessary to have a clip structure 50 and a member connected to the frame member 32. In this case there would not need to be two occluding elements 120. A single occlusion element 120 could be used to fill any gap between the two leaflets 16*a*, 16*b*. The shape of course would be different—likely an oval surface to extend between the commissures. The frame of such an element could be similar to that previously shown and described in connection with the first embodiment or another configuration.

Figure 12C:
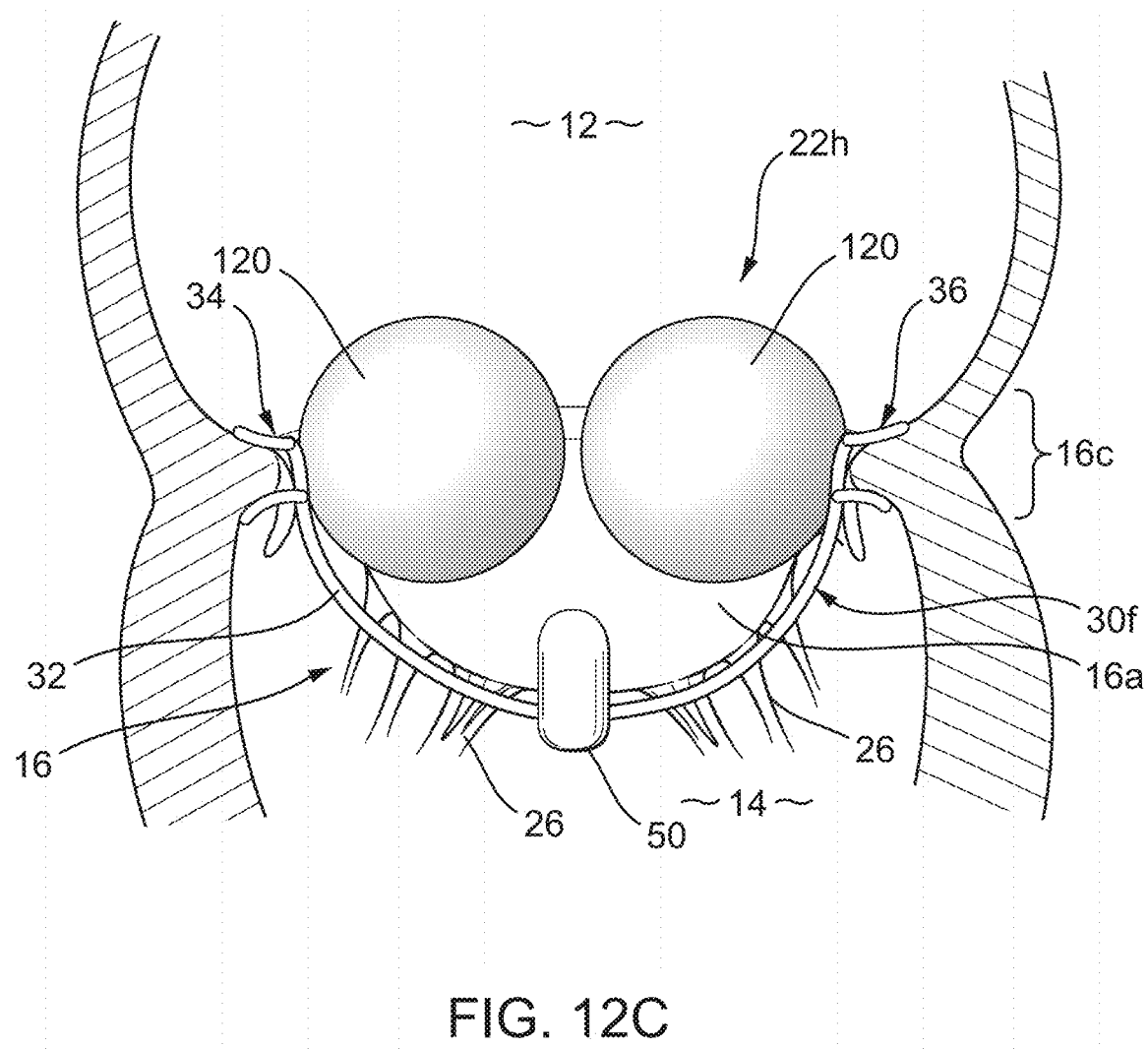
FIG. 12C is a view similar to FIG. 12B, but illustrating another alternative embodiment of a selective occlusion device implanted in a native mitral valve.

FIG. 12C shows another illustrative embodiment or variation of a selective occlusion device 22*h* mounted inside the heart to the native mitral valve 16. There are two selective occluding elements 120 attached to a frame structure 30*f*. The frame structure 30*f* is engaged with a clip structure 50 that is attaching the anterior and posterior leaflets 16*a*, 16*b* together centrally, e.g., near the A2/P2 junction. The frame structure 30*f* is stabilized by connectors 34, 36 at the commissures and annulus region 16*c* of the valve 16.

The embodiment of FIG. 12C is similar to that shown in FIGS. 12A and 12B. The difference here is that the support frame member 32 is not located above the elements 120 but below the elements 120. In other embodiments the support frame member 32 is located above the selective occlusion device and been directed to the left atrium. In this embodiment, the supporting frame member 32 is biased downward and toward the left ventricle, generally below the mitral valve 16. Also, in this embodiment, the frame member 32 can be directly connected to the clip structure 50 that attaches the two leaflets 16*a*, 16*b* and the frame structure 30*f* together. This may allow a procedure where the entire device is implanted at one time. The clip structure 50, with the selective occlusion device elements 120 coupled to frame structure 30*f*, could be delivered by a catheter (not shown). The clip structure 50 (with or without exposing the rest of the device) could be extruded outside the delivery catheter inside the heart 10. The clip structure 50 may then be closed on the native mitral valve anterior and posterior leaflets 16*a*, 16*b*. The remainder of the selective occlusion device 22*h* could be then released from the delivery catheter—placing the entire device in position. This may simplify the procedure to one step.

It is also important to note that in prior embodiments the frame structure has been above the clip structure 50, and in this embodiment, the frame structure 30*f* is below. It is also possible to have both an upper and a lower support frame structure (such as by combining two arc-shaped supports in one device). It would also be possible to join upper and lower arc support or frame members, so the support or frame structure is a complete loop or circle. This may provide further structural strength to the system.

Figure 12D:
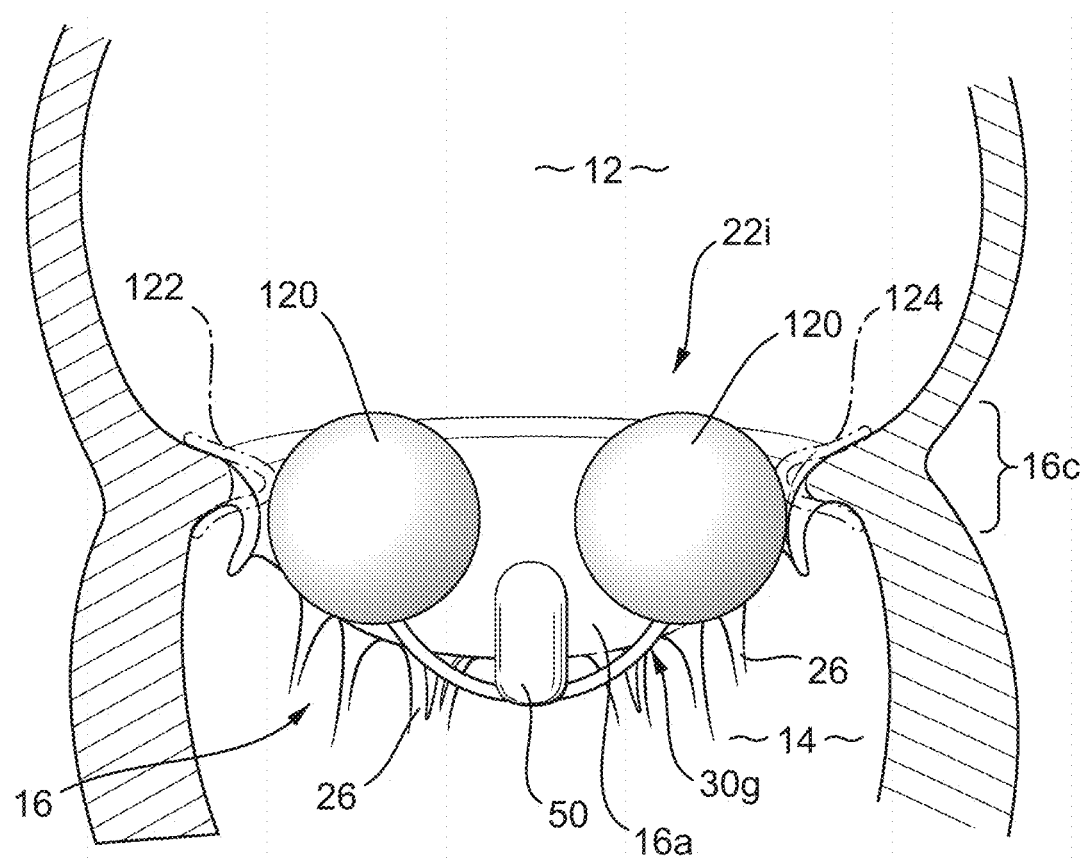
FIG. 12D is another view similar to FIG. 12C, but illustrating another alternative embodiment of a selective occlusion device implanted in the native mitral valve.

FIG. 12D is a side elevational view schematically illustrating another illustrative embodiment of a selective occlusion device 22*i* including first and second rigid or static selective occlusion elements 120 coupled with a frame structure 30*g*. In this embodiment, the rigid selective occlusion elements 120 are directly coupled to the frame structure 30*g*, which may be a frame member 32 coupled with the clip structure 50. As in previous embodiments, the clip structure 50 may directly couple respective margins of the anterior and posterior mitral leaflets 16*a*, 16*b*, or may couple these leaflet margins together against an intermediate spacer (not shown). This may be used to correctly orient and locate the rigid selective occlusion elements 120 on opposite sides of the clip structure 50 and within the side-by-side openings of the native mitral valve 16 created by the central clip structure 50. Optionally, additional connectors 122, 124 shown in broken lines may be used to help secure the rigid selective occlusion elements 120 in place at the commissures of the mitral valve 16.

FIGS. 13A and 13B schematically illustrate, in cross section, the functioning of the rigid, selective occlusion elements 120 shown in FIGS. 12A through 12D. Specifically, when the heart cycle is in systole the native mitral leaflets 16*a*, 16*b* will close against the rigid selective occlusion elements 120 to provide a fluid seal against regurgitation of blood flow. As shown in FIG. 13B, during diastole, the mitral valve leaflets 16*a*, 16*b* will spread apart and disengage from the rigid selective occlusion elements 120 to allow blood flow from the left atrium 12 into the left ventricle 14 between the rigid selective occlusion elements 120 and the respective native leaflets 16*a*, 16*b*. The one or more elements 120 fill any gap between the anterior and posterior leaflets 16*a*, 16*b*. When mitral regurgitation occurs due to failure of complete leaflet coaptation, the leaflets 16*a*, 16*b* are frequently pulled apart from each other in the plane of the valve 16 (here left-right). However, the situation may become more complex because the leaflets 16*a*, 16*b* tend to be pulled down into the ventricle 14 as well as apart from each other as mitral regurgitation becomes more severe over time. So, an up/down gap may also occur with one leaflet 16*a* or 16*b* sitting at a higher plane than the other leaflet 16*a*, 16*b*.

The advantage to a convexly curved outer surface of the element(s) 120 is that this surface can be shaped to adapt to a wide variety of defects that may occur between the anterior and posterior leaflets 16*a*, 16*b*. An outer, convexly curved surface of the element(s) 120 can accommodate leaflet gaps that are in the plane of the valve 16 (left right in the figure) and perpendicular to the plane of the valve 16 (up and down in the figure).

The selective occlusion device 22*g* is symmetric on each side. The elements 120 could also be constructed so that they are asymmetrical, i.e., not identical on opposite sides. For example, the posterior leaflet 16*b* may be more retracted into the left ventricle 14 than the anterior leaflet 16*a*. It may be useful to have adjustments in the element 120 on the side facing the posterior leaflet 16b to fill the gap left by a retracted posterior leaflet 16b. The element 120 may be constructed to be more prominent on the side of the element 120 adjacent to the posterior leaflet 16b than on the side adjacent or facing the anterior leaflet 16a. One or more elements 120 may be adjustable in shape, such as by an adjustable level of inflation to a hollow interior of the element 120 or other method, to accommodate any need to fill a gap between the leaflets 16a, 16b that would otherwise cause regurgitation.

Custom made or custom size elements 120 could also be made depending on the shape of the gap. A gap could be determined by echocardiography or CT and appropriately sized and shaped filling elements 120 could be selected based on measurements obtained with imaging. The valve defect that needs repair may be more shaped as a cylinder and a cylinder or pyramid-cylinder shape may be better to stop blood regurgitation than a lens or disc shape for the element(s) 120.

The margins of the element(s) 120 facing the oncoming flow of blood from the left atrium 12 has a tapering surface. This will allow the blood to flow smoothly into the left ventricle and avoid blood damage or hemolysis and to promote complete and unimpeded filling of the left ventricle 14. The edge of the element(s) 120 inside the left ventricle 14 also demonstrates a taper similar to the inflow region of the element(s) 120. When the heart begins to contract, blood will be ejected back toward the element(s) 120 and the native leaflets 16a, 16b will begin to move toward the element(s) 120 to produce a complete seal—preventing regurgitation of blood during systole.

Figure 13C:
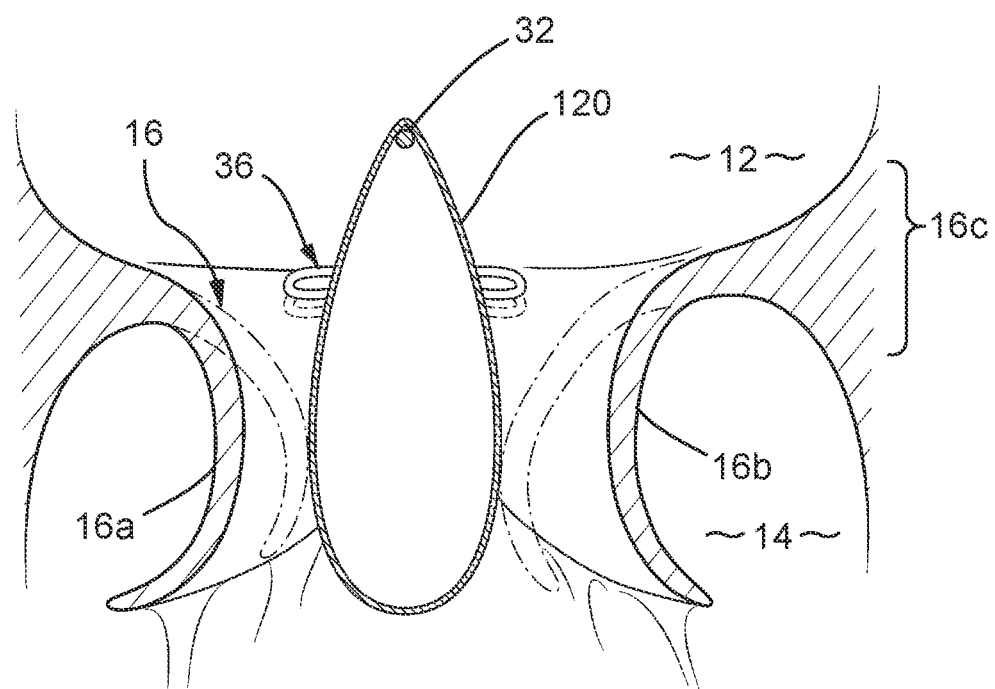
FIG. 13C is a view similar to FIG. 13B, but showing another embodiment of the selective occlusion element.

An additional option is provided and illustrated in FIG. 13C. The rigid selective occlusion element(s) 120 may be formed in a fluid efficient manner, such as a teardrop shape or other hemodynamic shape to prevent undesirable blood flow patterns and damage or hemolysis as the blood flows past the elements 120 in between the element 120 and the respective mitral leaflets 16a, 16b.

Figure 14A:
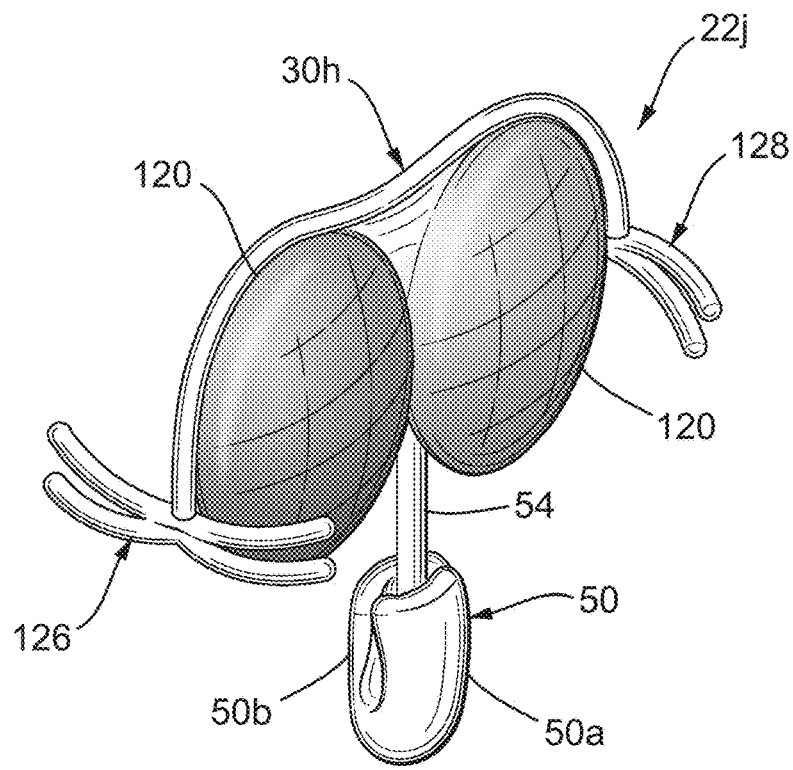
FIG. 14A is a perspective view of another alternative embodiment of a selective occlusion device and mitral valve clip structure.
Figure 14B:
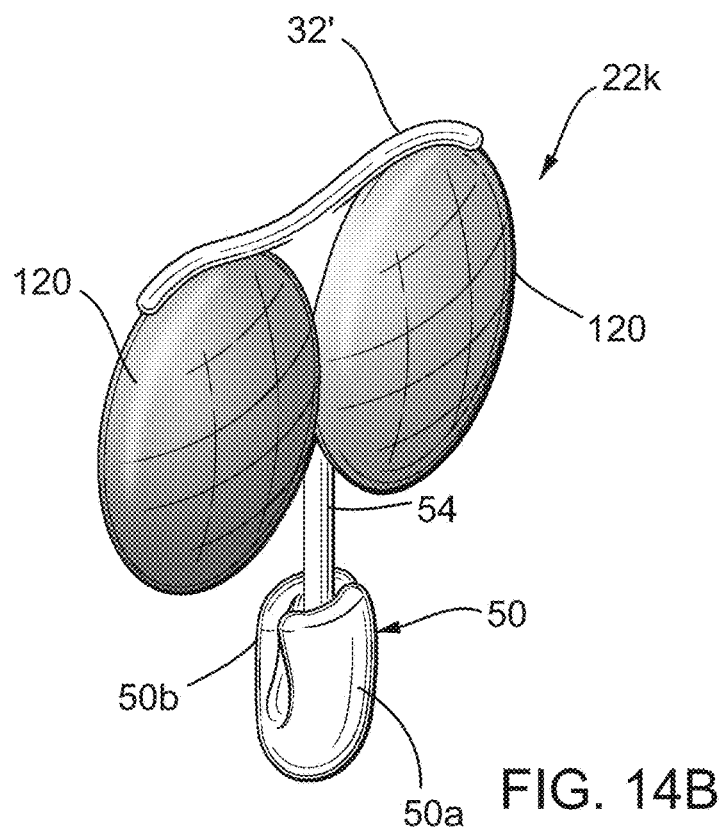
FIG. 14B is a perspective view of another alternative embodiment of a selective occlusion device and mitral valve clip structure.
Figure 14C:
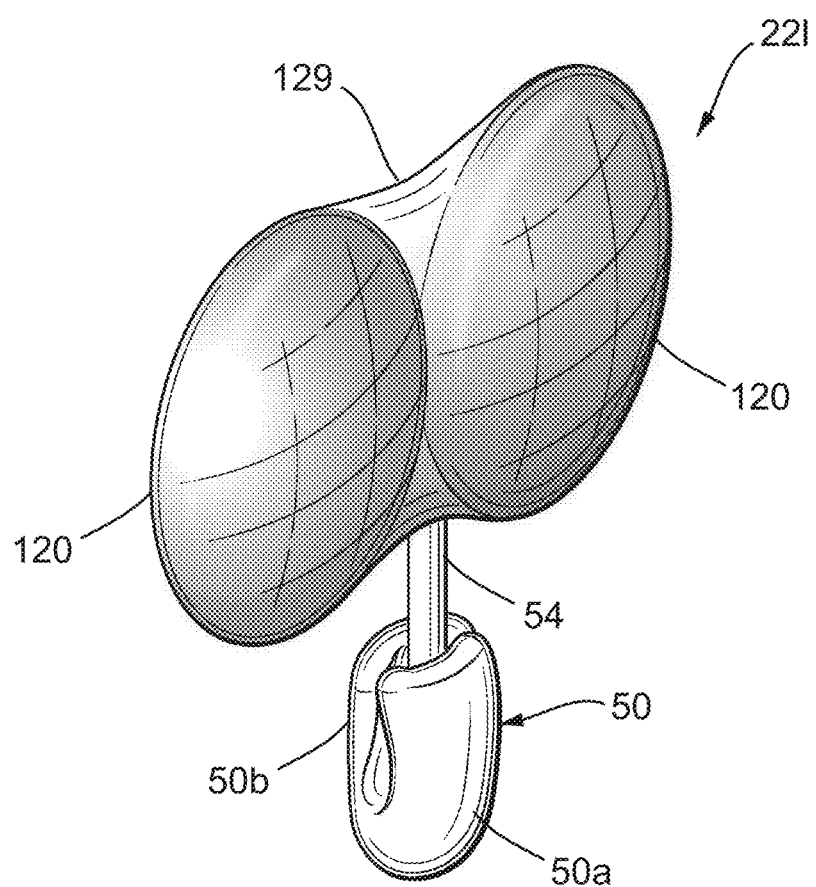
FIG. 14C is a perspective view of another alternative embodiment of a selective occlusion device and mitral valve clip structure.
Figure 15A:
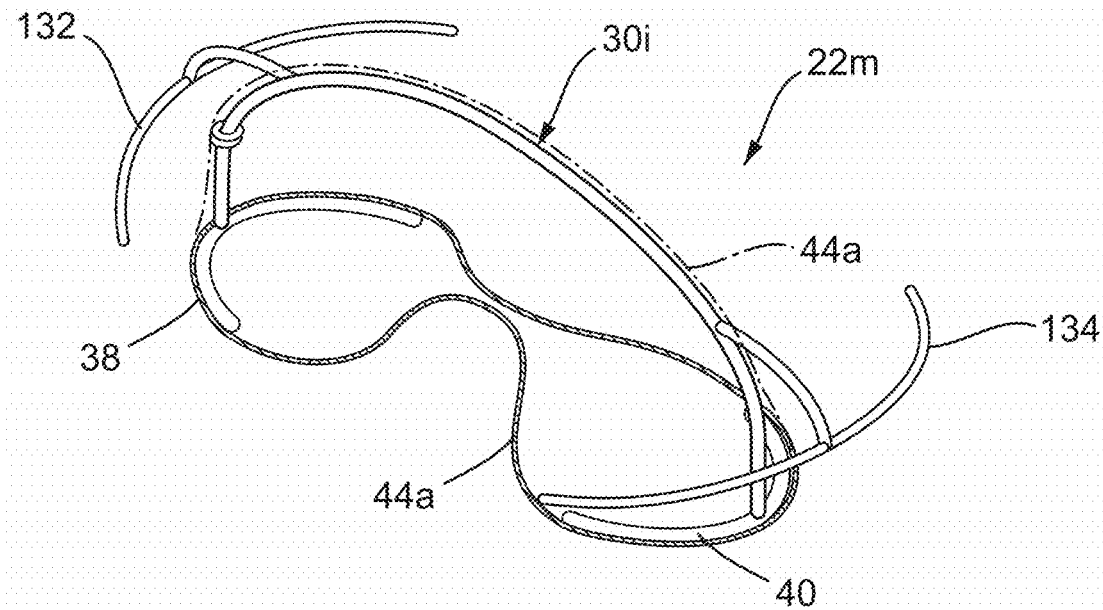
FIG. 15A is a perspective view of another alternative embodiment of a selective occlusion device with the flexible membrane of the device broken away for clarity.
Figure 15B:
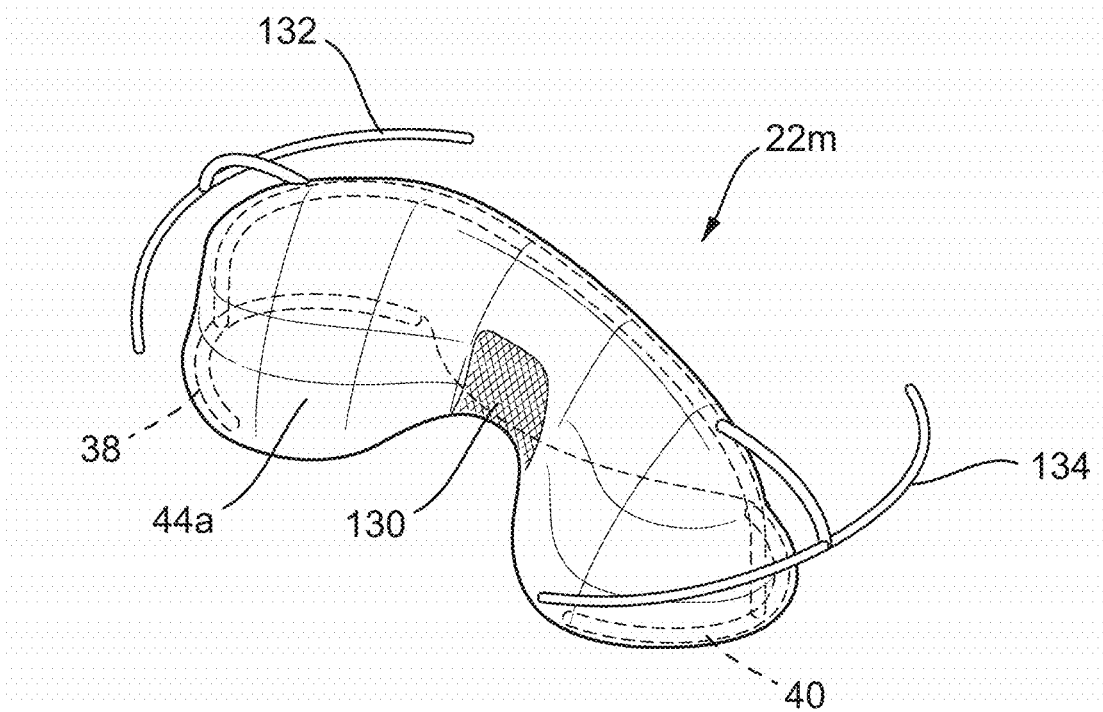
FIG. 15B is a perspective view similar to FIG. 15A, but further illustrating a flexible membrane on the frame structure.
Figure 15C:
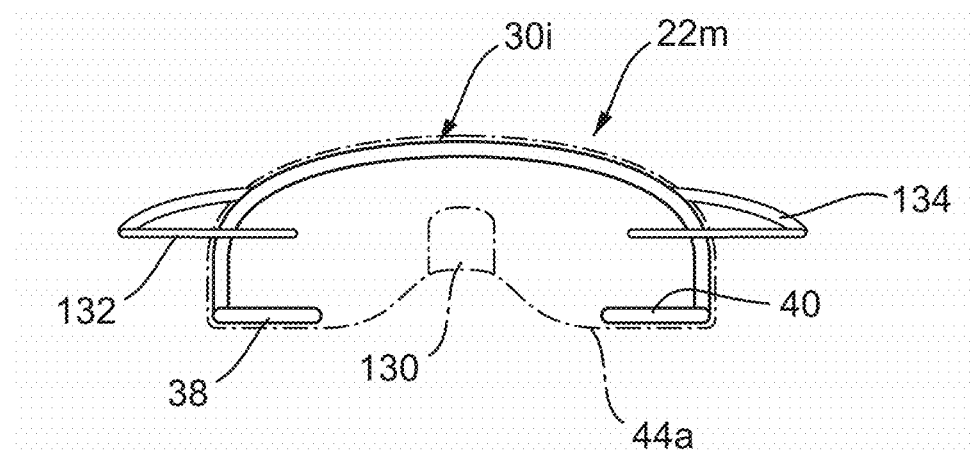
FIG. 15C is a side elevational view of the selective occlusion device shown in FIGS. 15A and 15 B with the flexible membrane removed for clarity.
Figure 15D:
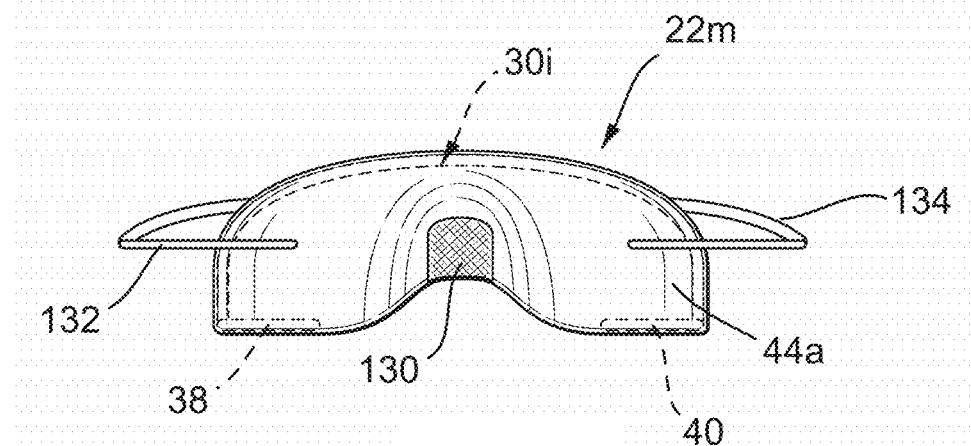
FIG. 15D is a side elevation view similar to FIG. 15C, but illustrating the flexible membrane applied to the frame structure.
Figure 15E:
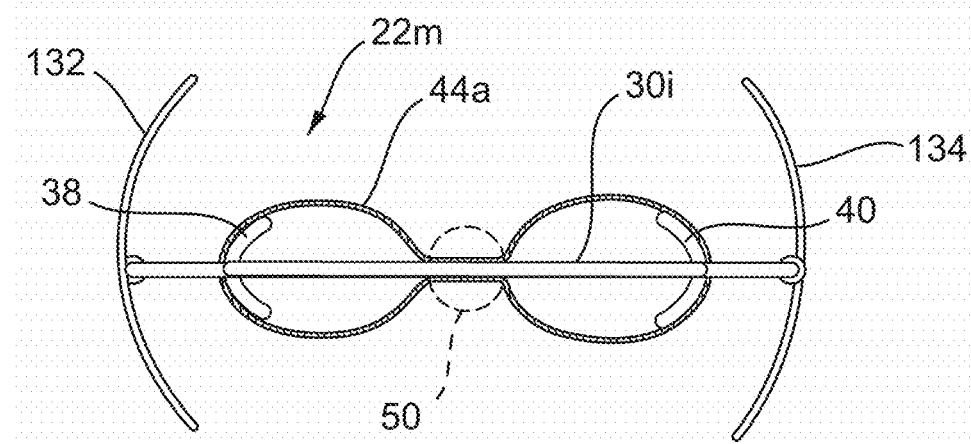
FIG. 15E is a top view of the device shown in FIGS. 15A through 15D, but illustrating the membrane cross-sectioned to show the membrane shape in the expanded or filled condition when the heart is in the systole phase.

FIGS. 14A, 14B and 14C illustrate additional embodiments of selective occlusion devices 22j, 22k, 22l that utilize rigid or static selective occlusion elements 120. These elements 120 function as discussed above in connection with FIGS. 12A through 12D and FIGS. 13A, 13B. In FIG. 14A the rigid or static selective occlusion elements 120 are coupled to a frame structure 30h that is secured along top margins of the elements 120. At each end of the frame structure 30h respective commissure connectors 126, 128 are provided that include connecting elements which operate the same as the butterfly type elements previously described by sandwiching mitral tissue or other heart tissue therebetween. Additional securement is provided by the clip structure 50 and a suitable tensile element or other connector 54, such as also previously described.

FIG. 14B illustrates an embodiment of a selective occlusion device 22k in the form of rigid or static elements 120 that are again generally disc shaped and secured together by a frame member 32', a tensile element or connector 54 and a connected clip structure 50.

FIG. 14C illustrates an embodiment of a selective occlusion device 22l in which the rigid selective occlusion elements 120 are secured together by fabric or other structure 129, and further secured through a tensile member or other connector 54 to a clip structure 50 which secures the selective occlusion device 22l to the native mitral valve 16 through a clipping action as previously described.

FIGS. 15A through 15E illustrate another embodiment of a selective occlusion device 22m including a flexible membrane 44a and a frame structure 30i. The flexible membrane 44a is secured to frame structure 30i that is also preferably flexible for reasons such as previously described. This embodiment is similar to previous embodiments utilizing flexible membranes 44a in conjunction with a mitral valve clip structure 50, but includes a central reinforced area such as a fabric area 130 allowing the native leaflet margin tissue to be a clipped against the reinforced fabric area 130 directly. The clip structure 50 is shown in broken lines in FIG. 15E. In this alternative, the native mitral tissue is not directly contacting abutting native mitral tissue but instead contacts and is secured against the reinforced central fabric area 130 of the flexible membrane 44a. This fabric or other reinforcing material 130 may, for example, be useful in situations where the remainder of the flexible membrane is formed from more delicate material such as biologic material. Annulus connectors 132, 134 are provided and rest against an upper portion of the annulus 16c as generally shown in other figures, such that the clip structure 50 (not shown in this embodiment) secures the selective occlusion device 22m to the reinforced, central area 130 from below, and the annulus connectors 132, 134 secure the selective occlusion device 22m from above by bearing against or otherwise coupling to the native annulus 16c.

Figure 16A:
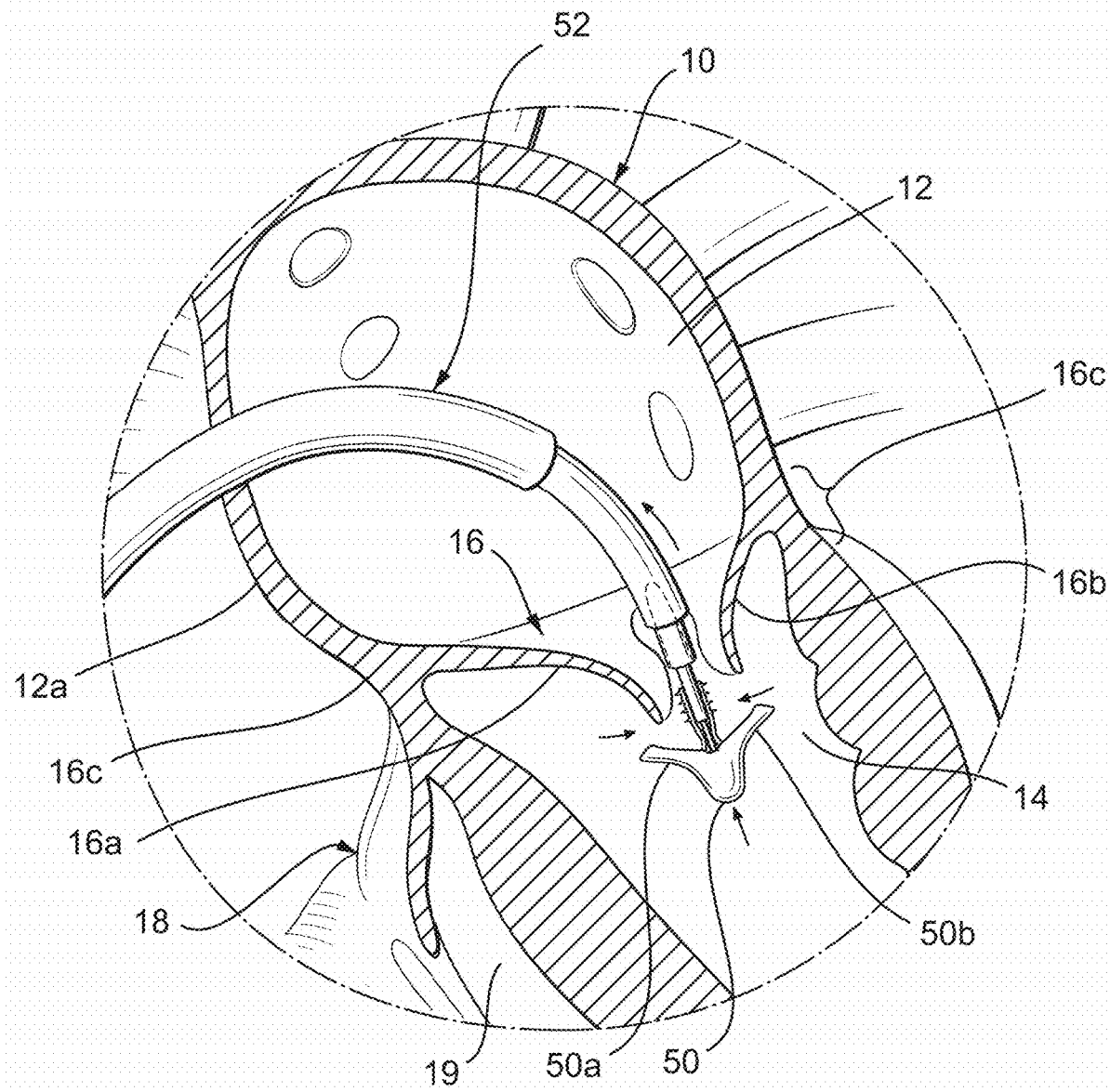
FIG. 16A is a perspective view of a system and of the heart, similar to FIG. 5A, but illustrating another alternative embodiment of a catheter-based system and method for implanting a selective occlusion device and a clip structure in the native mitral valve.
Figure 16B:
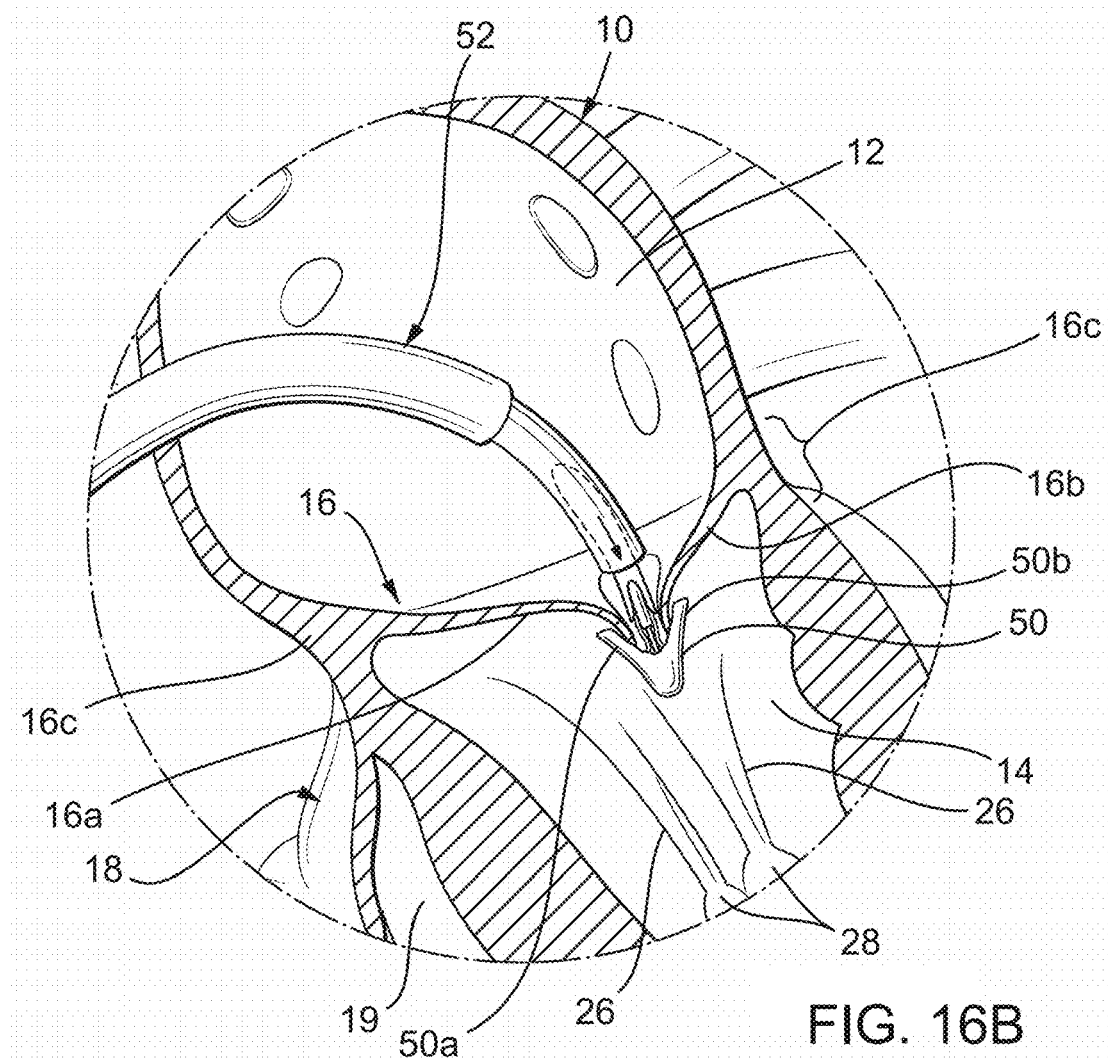
FIG. 16B is a perspective view similar to FIG. 16A, but illustrating a subsequent step in the method.
Figure 16C:
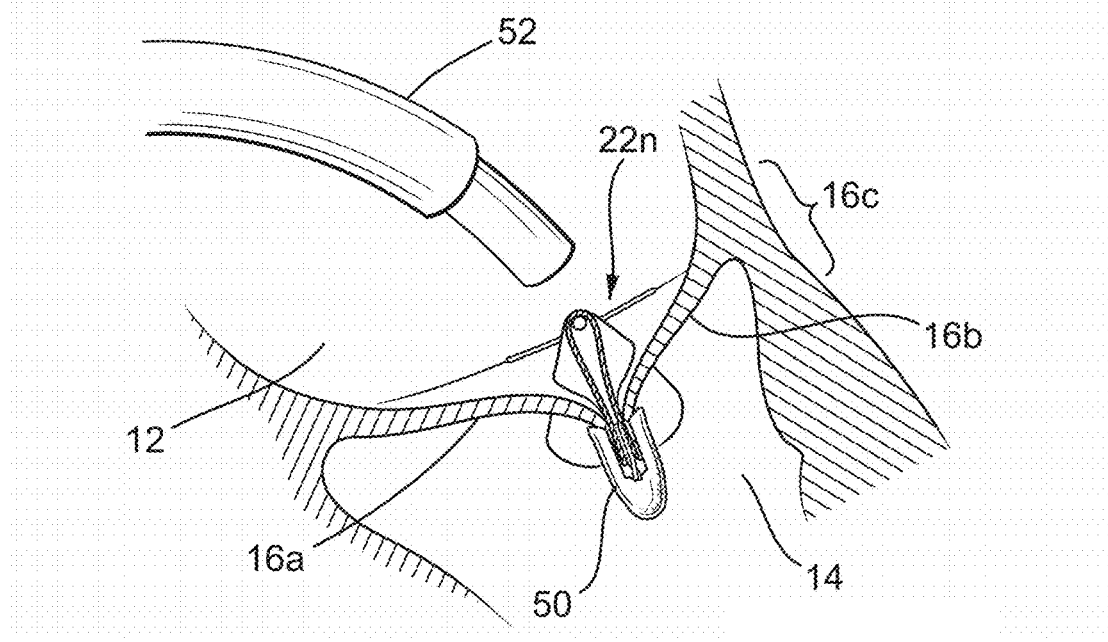
FIG. 16C is a view similar to FIG. 16B, but illustrating another subsequent step in the method.
Figure 16D:
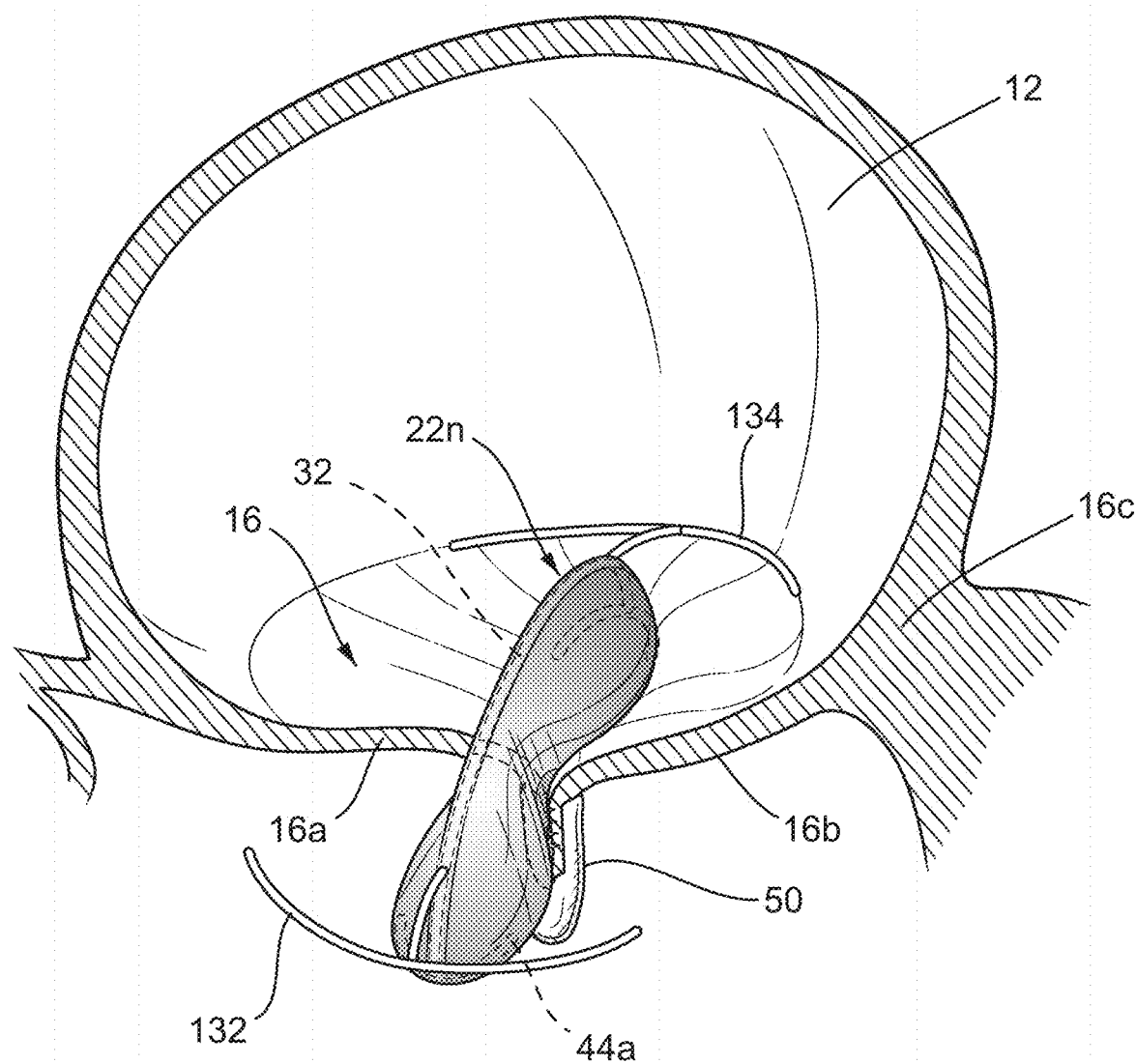
FIG. 16D is a perspective view illustrating the implanted selective occlusion device in the mitral valve of the patient.

FIGS. 16A through 16D illustrate another illustrative embodiment of a transcatheter delivered selective occlusion device 22n combined with a clip structure 50. Again, the clip structure 50 is used to affix a lower central margin portion of one leaflet 16a to a lower central margin portion of the opposing leaflet 16b, generally as previously described. Again, this clipping action may be for purposes of clipping the anterior leaflet 16a directly in contact with the posterior leaflet 16b at the central location, or clipping the anterior and posterior leaflets 16a, 16b against an intermediate spacer. In this embodiment, the selective occlusion device is coupled with the clip structure 50 delivered through one or more catheters 52. As shown in FIGS. 16A and 16B, the catheter assembly 52 is delivered transeptally into the left atrium 12 and downwardly through the native mitral valve 16 although other approaches may be used instead in the various embodiments. The clip structure 50 is extruded from the catheter assembly distal end and, in the open condition shown in FIG. 16A captures the leaflet margin portions as shown in FIG. 16B and is actuated to move one or both clip elements 50a, 50b together into the position shown in FIG. 16C to secure the central leaflet margin portions together. The remaining portion of the selective occlusion device 22n is then extruded from the distal end of the catheter assembly 52 as shown in FIG. 16C. As shown in FIG. 16D the selective occlusion device 22n, which may be, as illustrative examples, of the type shown in FIG. 16D or any of the types otherwise shown and described herein, or even other configurations contemplated hereby, self-expands into the mitral valve location. Operation of the selective occlusion device 22n may be generally as described herein, and securement of the device 22n occurs generally between the clip structure 50 and respective annulus connectors 132, 134. Specifically, as previously discussed, the annulus connectors 132, 134 provide a downward force for securing the device 22n generally at the annulus 16c, while the clip structure 50 provides an upward force to generally secure the selective occlusion device 22n therebetween in place in the native mitral valve 16.

Figure 17A:
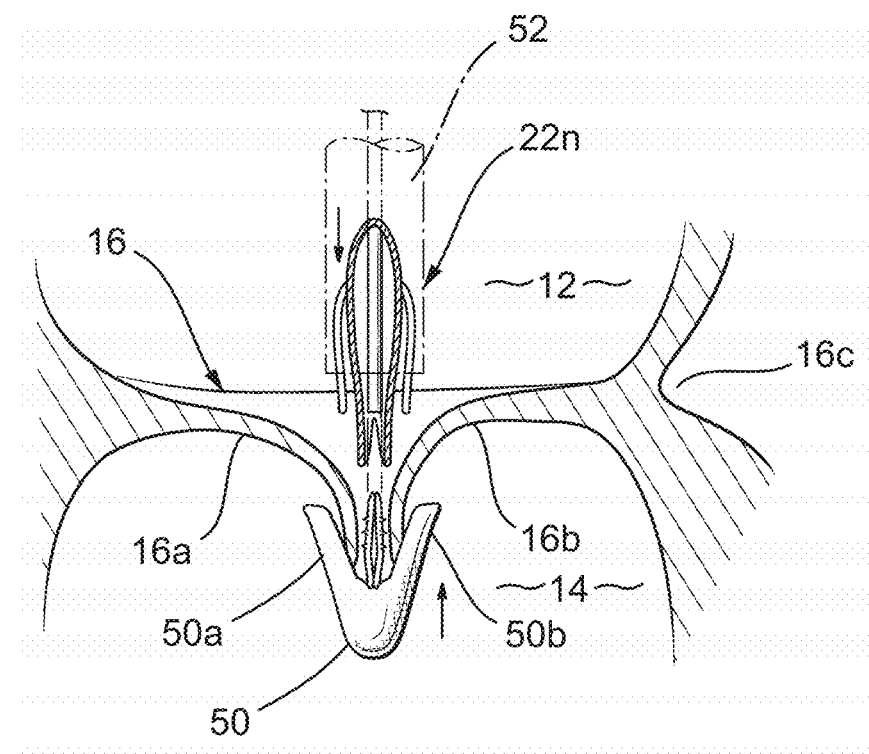
FIG. 17A is a side cross-sectional view of the native mitral valve and of the selective occlusion device of FIGS. 16A through 16D being implanted and secured to the mitral valve clip structure.
Figure 17B:
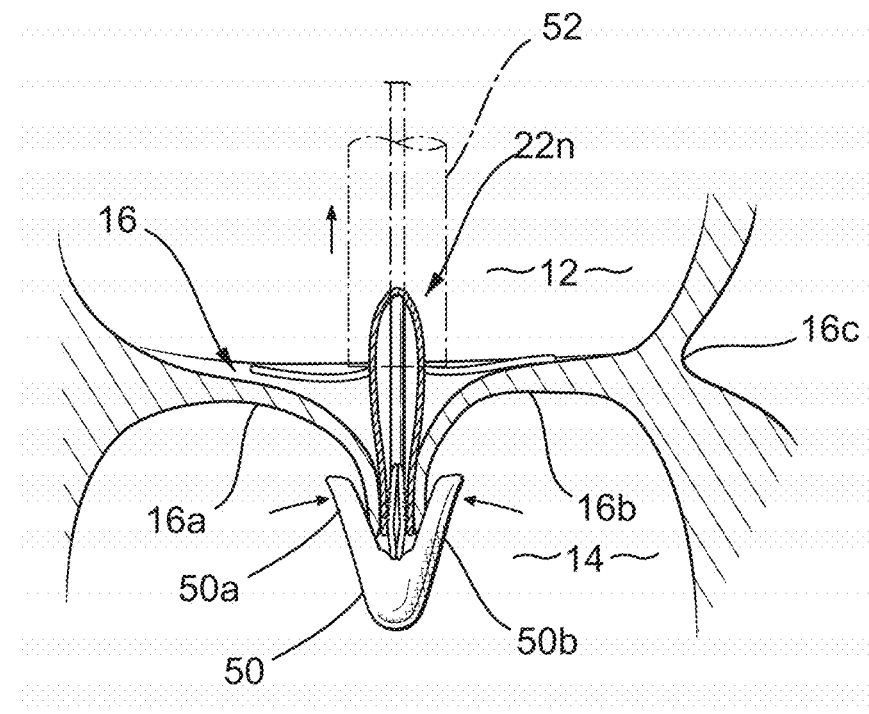
FIG. 17B is a side cross-sectional view similar to FIG. 17A, but illustrating a subsequent step in the method.
Figure 17C:
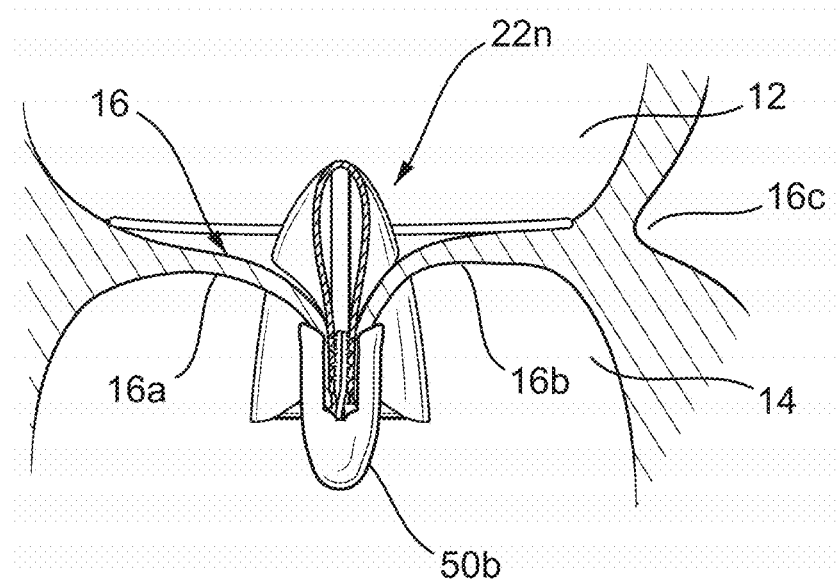
FIG. 17C is a side cross-sectional view similar to FIG. 17B, but illustrating another subsequent step in the method in which the apparatus is fully implanted.
Figure 18A:
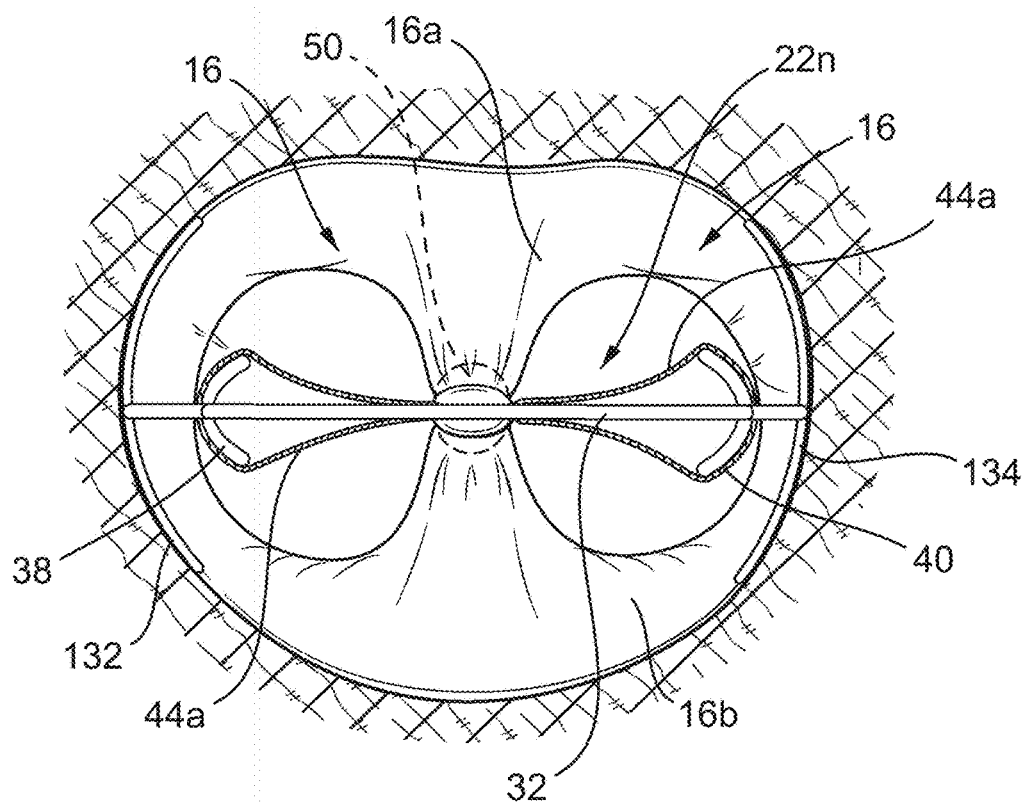
FIG. 18A is a cross sectional view of the selective occlusion device, as shown in FIGS. 16A through 16D and 17A through 17C, with the device and mitral valve shown when the heart is in the diastole phase.
Figure 18B:
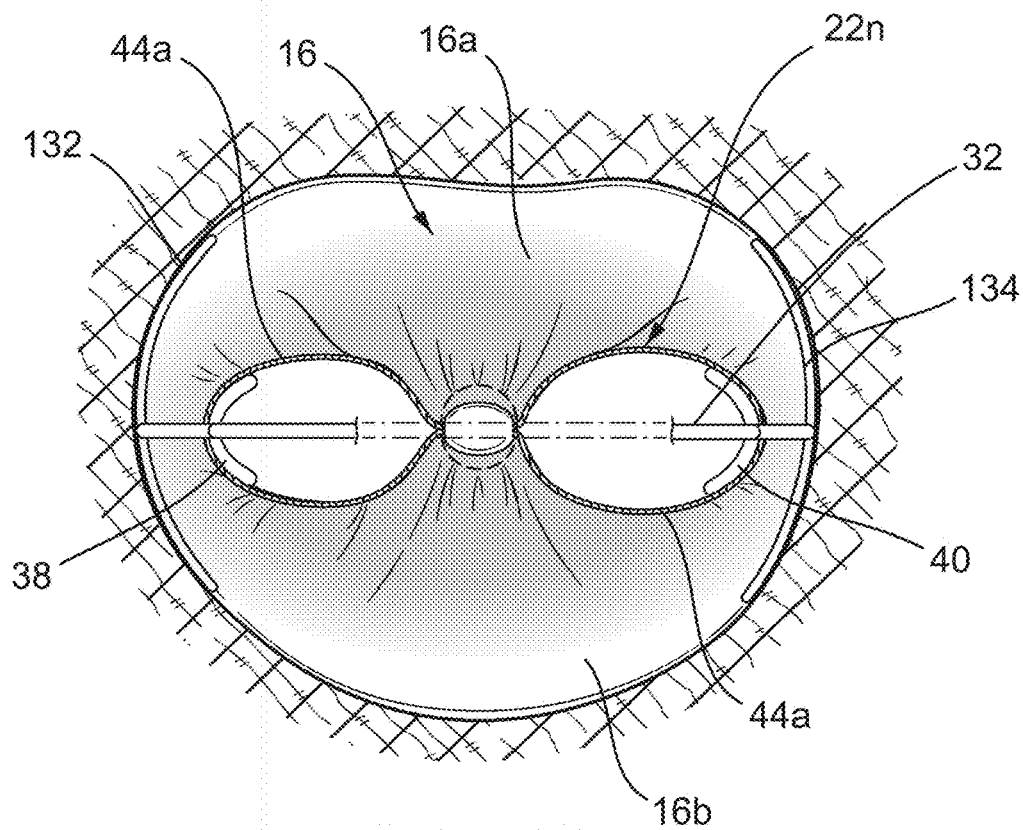
FIG. 18B is a view similar to FIG. 18A, but illustrating the device and the native mitral valve when the heart is in the systole phase.

FIGS. 17A through 17C illustrate an embodiment of an apparatus for transcatheter delivery and implantation. In this embodiment, the clip structure 50 is delivered below the mitral valve 50 generally as previously described, and the selective occlusion device 22*n* is delivered to a location above the native mitral valve 16. The selective occlusion device 22*n* is inserted into the mitral valve 16 and between the native leaflets 16*a*, 16*b*, and also between the clip elements as shown in the method proceeding from FIG. 17A to 17B. Once in position as shown in FIG. 17B, at least one of the clip elements is moved toward the other clip element to clip or clamp the leaflet margins together, as previously described, and also to clamp a lower central portion of the selective occlusion device 22*n* and, particularly, the flexible membrane 44*a* in this embodiment, such that the leaflet margins are secured together at the same time as the selective occlusion device 22*n* is secured and implanted in place within the native mitral valve 16. As shown in FIG. 17C, the selective occlusion device 22*n* is fully extruded from the catheter assembly, whereupon it self-expands into position in the native mitral valve 16 and functions as otherwise generally discussed herein. More particularly, FIGS. 18A and 18B illustrate the diastole and systole portions, respectively, of the heart cycle with the apparatus secured in place as described in connection with FIGS. 17A through 17C. In FIG. 18A, during diastole, blood flow is allowed between the native mitral leaflets 16*a*, 16*b* and the flexible membrane 44*a*, while in systole the flexible membrane 44*a*, in each section, fills with blood and thereby expands or inflates as the mitral leaflets 16*a*, 16*b* move toward one another and against the flexible membrane 44*a* to form a fluid seal preventing regurgitation of blood flow from the left ventricle 14 into the left atrium 12 of the heart 10.

Figure 19:
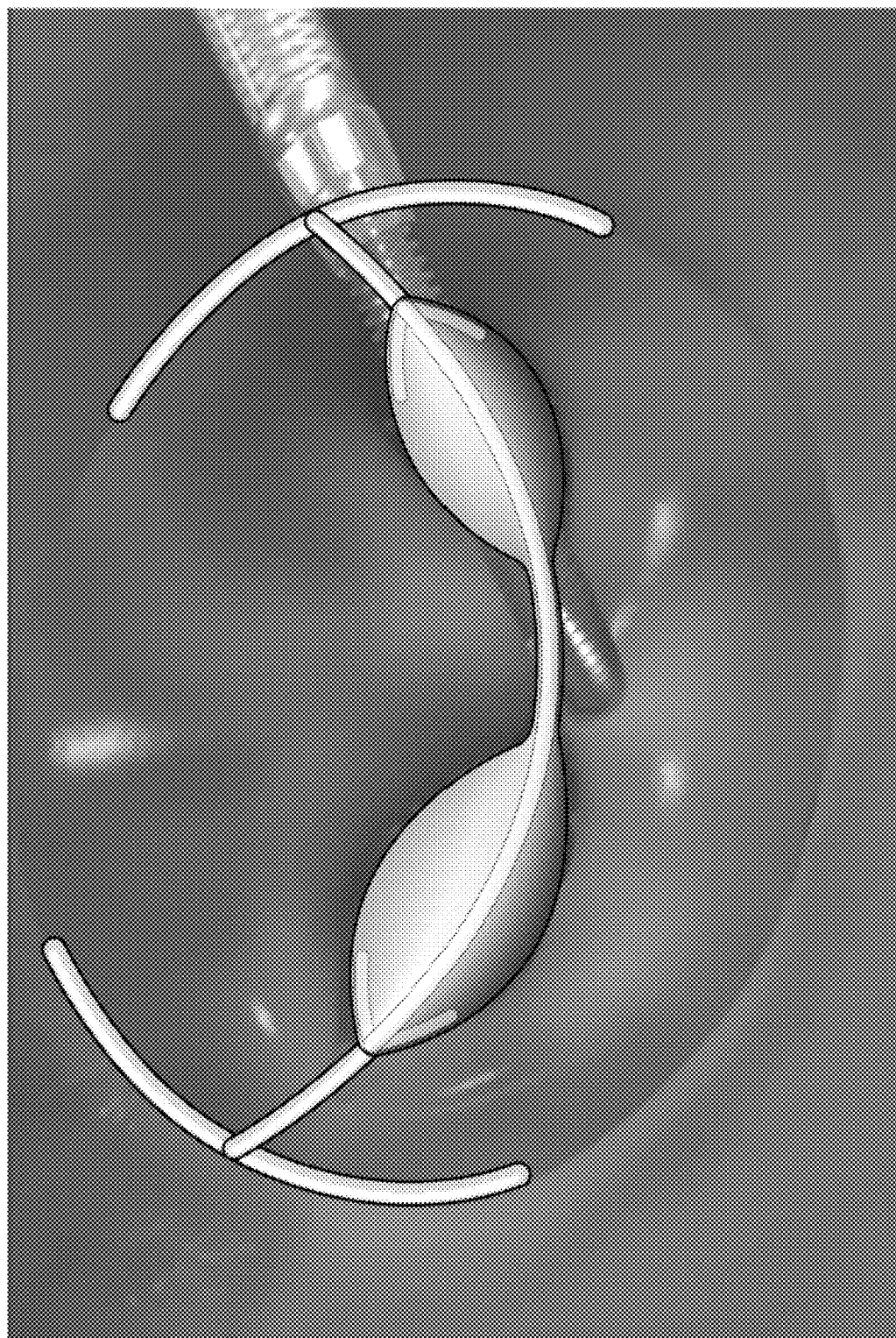
FIG. 19 is a top view schematically illustrating a representation for the shape of the selective occlusion device when implanted in a native mitral valve having an anatomical curvature.
Figure 20:
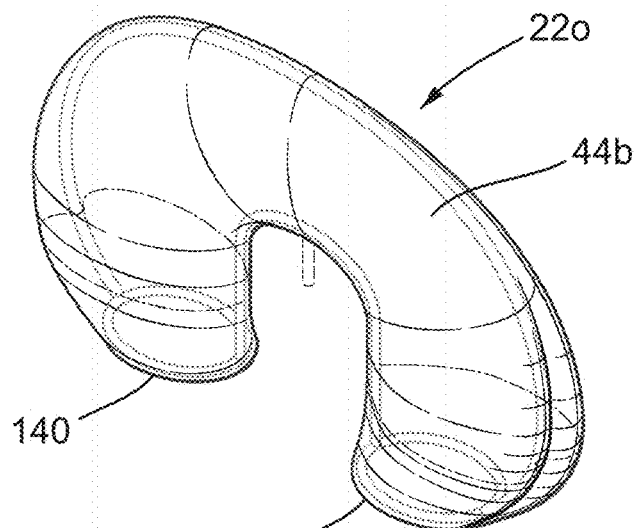
FIG. 20 is a perspective view of a selective occlusion device constructed in accordance with another alternative embodiment.

FIG. 19 is an anatomical view from above the native mitral valve 16 with the selective occlusion device 22*n* superimposed to show another representation for the configuration in which the selective occlusion device 22*n* is curved and flexes in accordance with the natural curvature of the mitral valve 16.

Figure 21A:
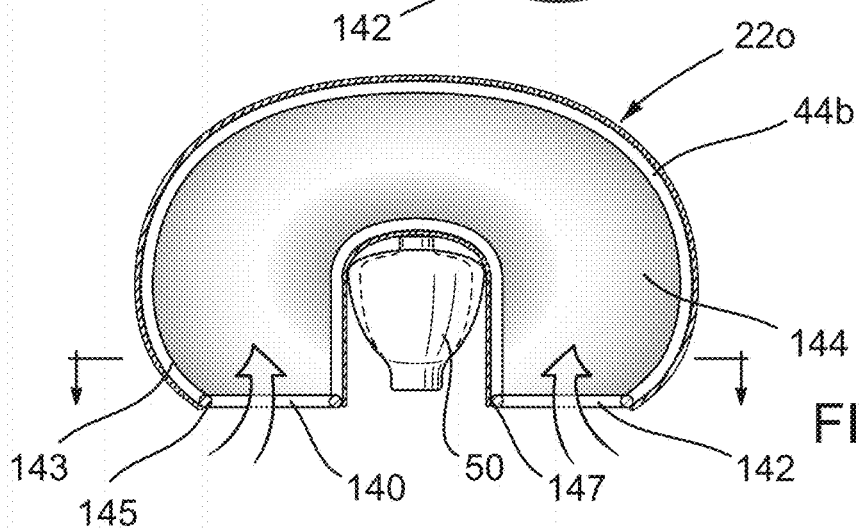
FIG. 21A is a side cross-sectional view taken generally lengthwise along a central portion of the device shown in FIG. 20.
Figure 21B:
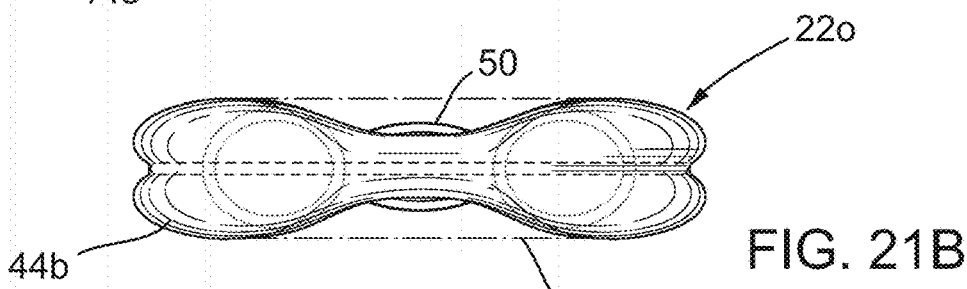
FIG. 21B is a top view of the device shown in FIG. 21A.
Figure 21C:
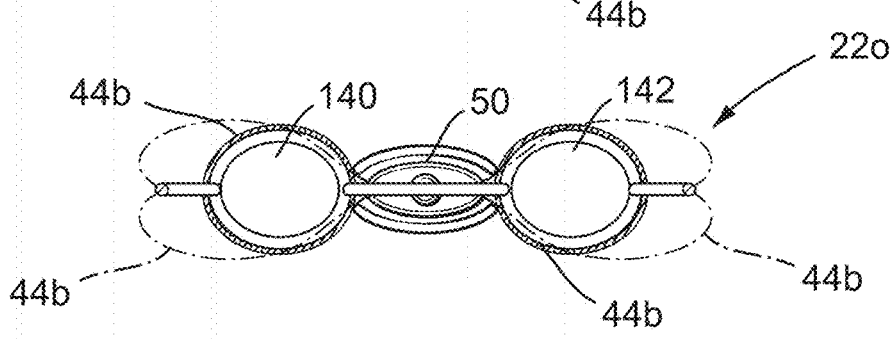
FIG. 21C is a cross-sectional view of the device shown in FIG. 21B.

FIGS. 20, 21A, 21B and 21C illustrate another embodiment for a selective occlusion device 22*o* and apparatus (combining the device 22*o* with a clip structure 50), in which the selective occlusion device 22*o* is configured generally as a two section device, but with the sections in fluid communication as best shown in FIG. 21A. A clip structure 50 is secured to the selective occlusion device 22*o* at a position between respective open ends 140, 142 of the sections. The clip structure 50 is used in the same manner as previously described. The flexible membrane 44*b* is supported by a flexible but strong frame structure 143, which may be formed in any manner contemplated herein, such as for allowing transcatheter delivery and implantation. The open ends 140, 142 are defined by hoop or ring portions 145, 147 of the frame structure 143. The hollow interior 144 of a flexible membrane 44*b* receives blood flow in the systole portion of the heart cycle and fluid communication between the two openings 140, 142 ensures better rinsing or washing during the heart cycle to reduce the chances of blood clots.

Figure 22A:
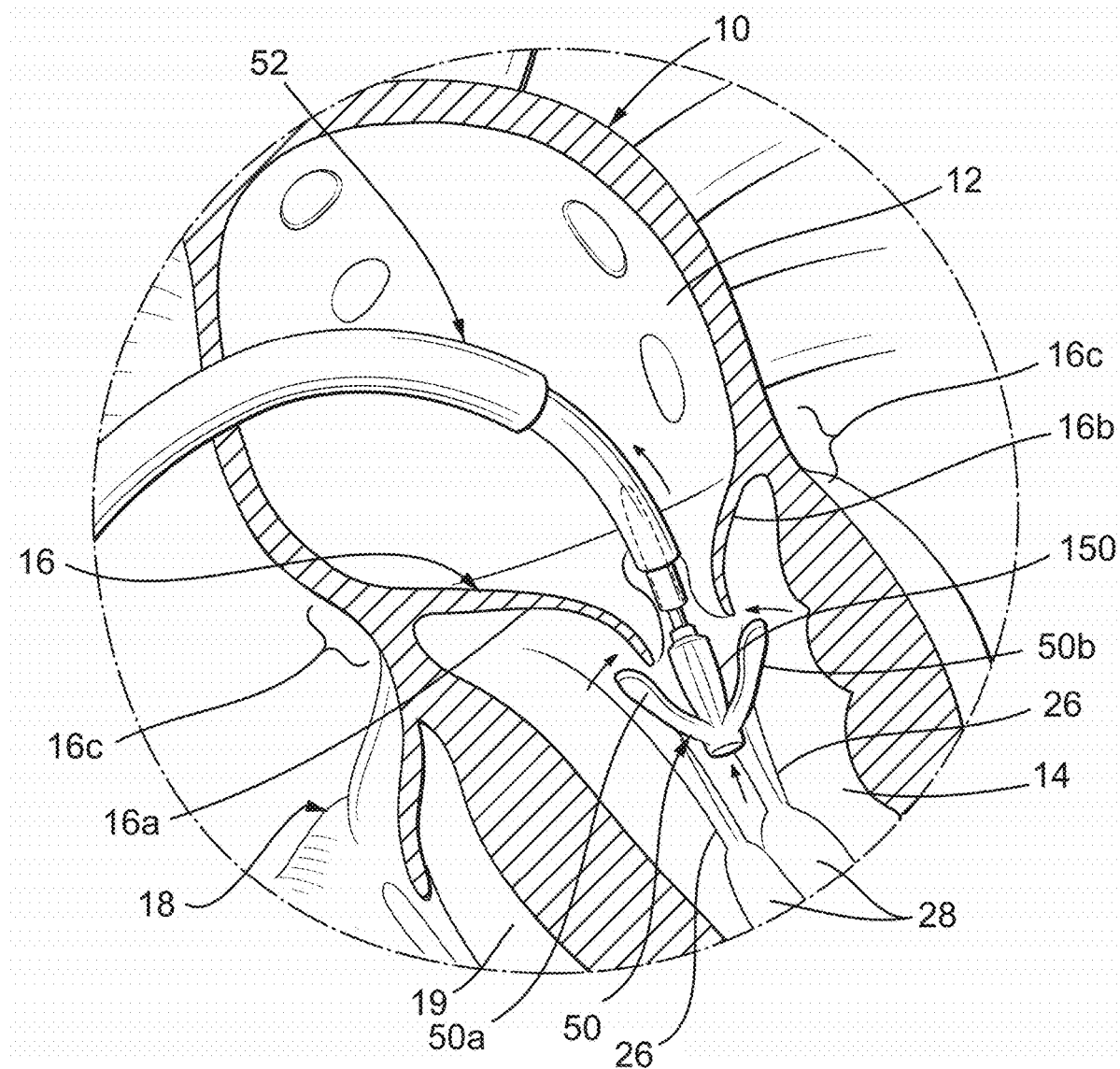
FIG. 22A is a perspective view of a catheter-based system and method according to another alternative embodiment being performed on a native mitral valve, shown in a schematic cross-sectioned portion of the heart.
Figure 22B:
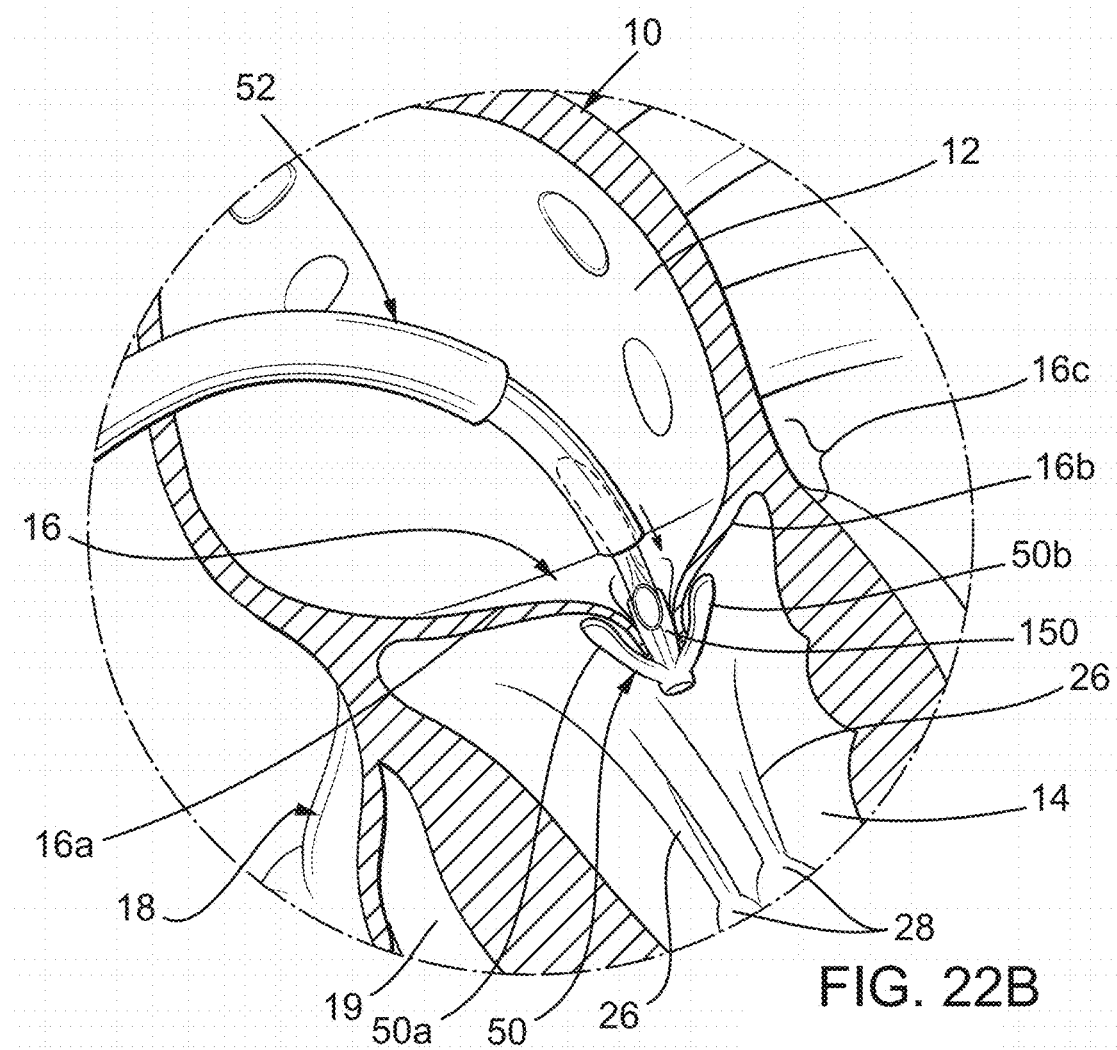
FIG. 22B is a view similar to FIG. 22A, but illustrating a subsequent step in the method.
Figure 22C:
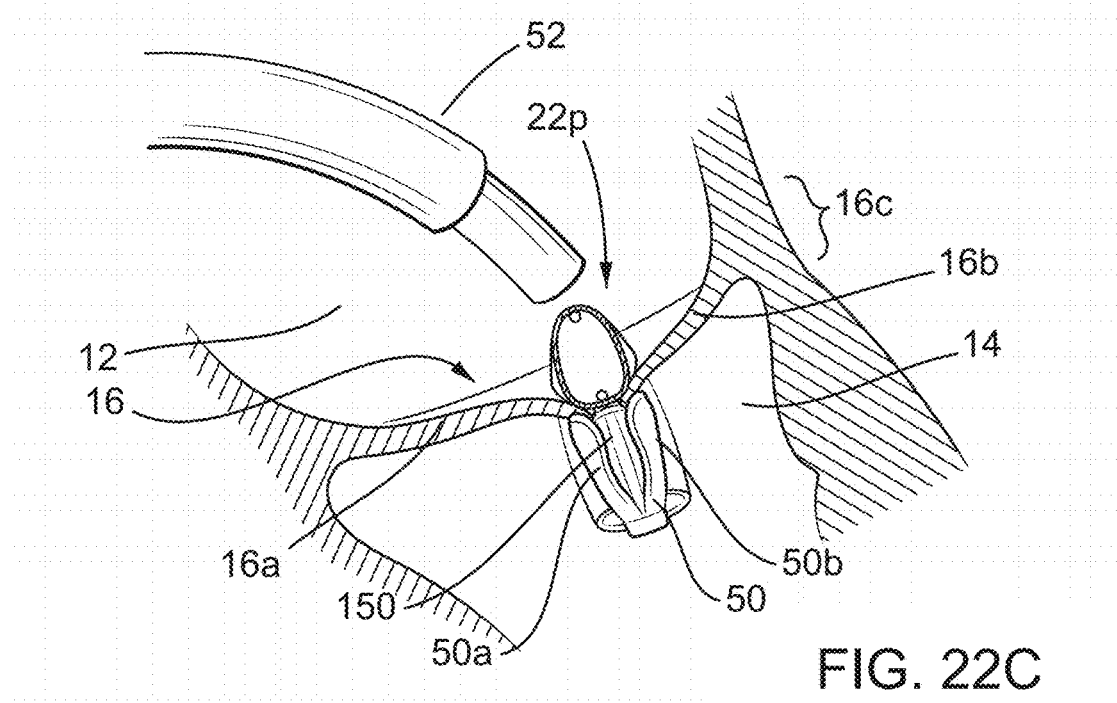
FIG. 22C is a view similar to FIG. 22B, but illustrating another subsequent step in the method.

FIGS. 22A through 22D illustrate another embodiment of an apparatus for transcatheter delivery and implantation of a clip structure 50 coupled with a selective occlusion device 22*p*. A difference with this embodiment is that the clip structure 50 clips the native mitral leaflets 16*a*, 16*b* against a central or intermediate spacer 150, instead of directly into contact with each other. The procedure is generally shown in FIGS. 22A through 22C in which the clip structure 50 is first extruded from the transseptally directed catheter assembly 52 generally at a location below the mitral leaflets 16*a*, 16*b*. The leaflets 16*a*, 16*b* are captured against the intermediate spacer 150, as shown in FIG. 22B. The leaflets 16*a*, 16*b* are secured firmly against the spacer 150 as shown in FIG. 22C by moving at least one of the clip elements 50*a*, 50*b* toward the other. In this embodiment, each clip element 50*a*, 50*b* is moved toward the central or intermediate spacer 150 to clamp leaflet tissue against the spacer 150. The selective occlusion device 22*p*, in this illustrative embodiment, is already secured to the clip structure 50 when it is extruded from the catheter assembly 52 as illustrated in FIG. 22C whereupon the selective occlusion device 22*p* self-expands into the implanted condition shown in FIG. 22D. It will be appreciated that the selective occlusion device 22*p* may be extruded and implanted as a separate component, as well as coupled to the clip structure 50 in a suitable manner, instead of being extruded in an already assembled form from the catheter or catheters 52.

Figure 22D:
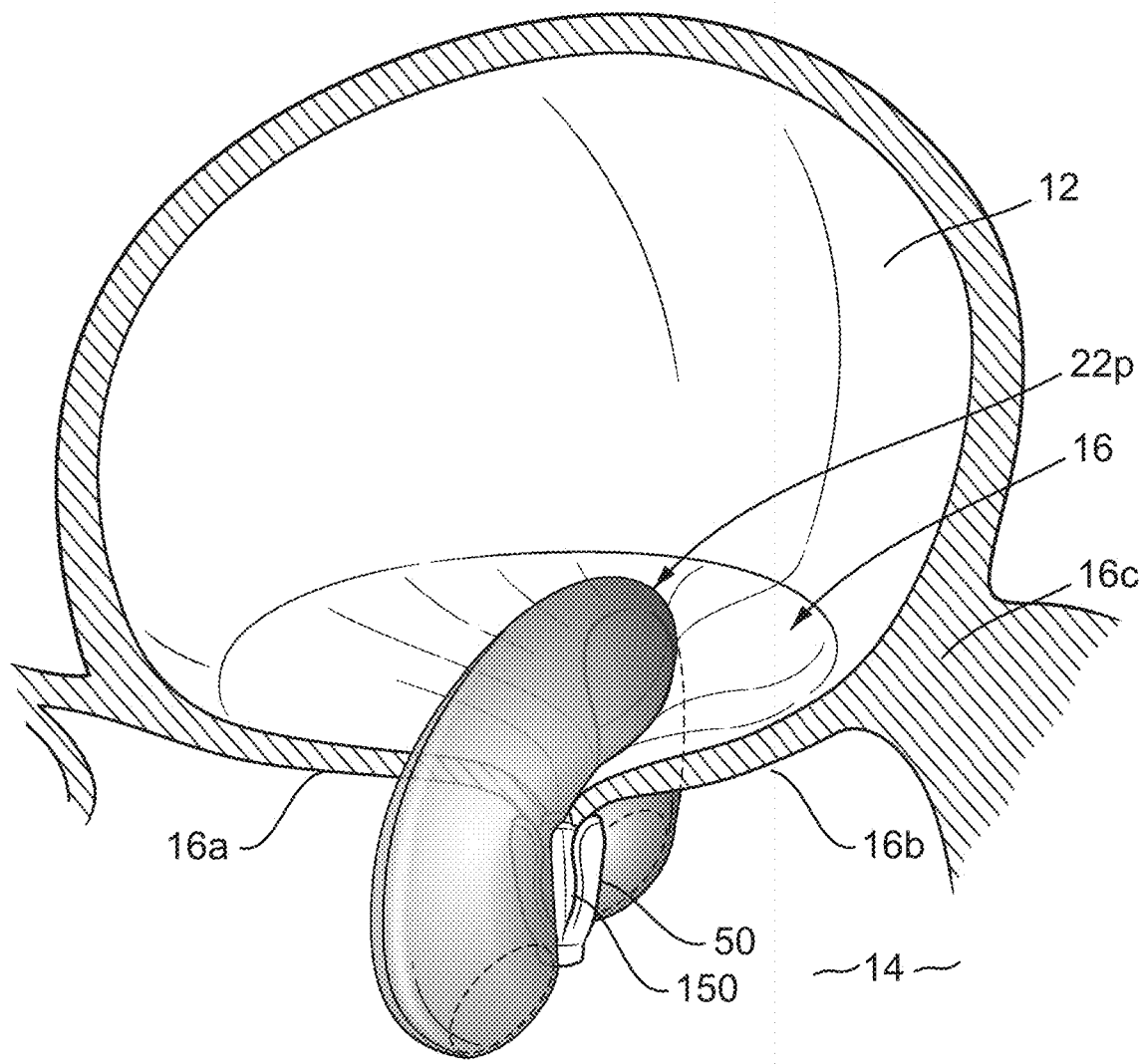
FIG. 22D is a perspective view illustrating the fully implanted apparatus in the native mitral valve, resulting from the method shown in FIGS. 22A through 22C.
Figure 22E:
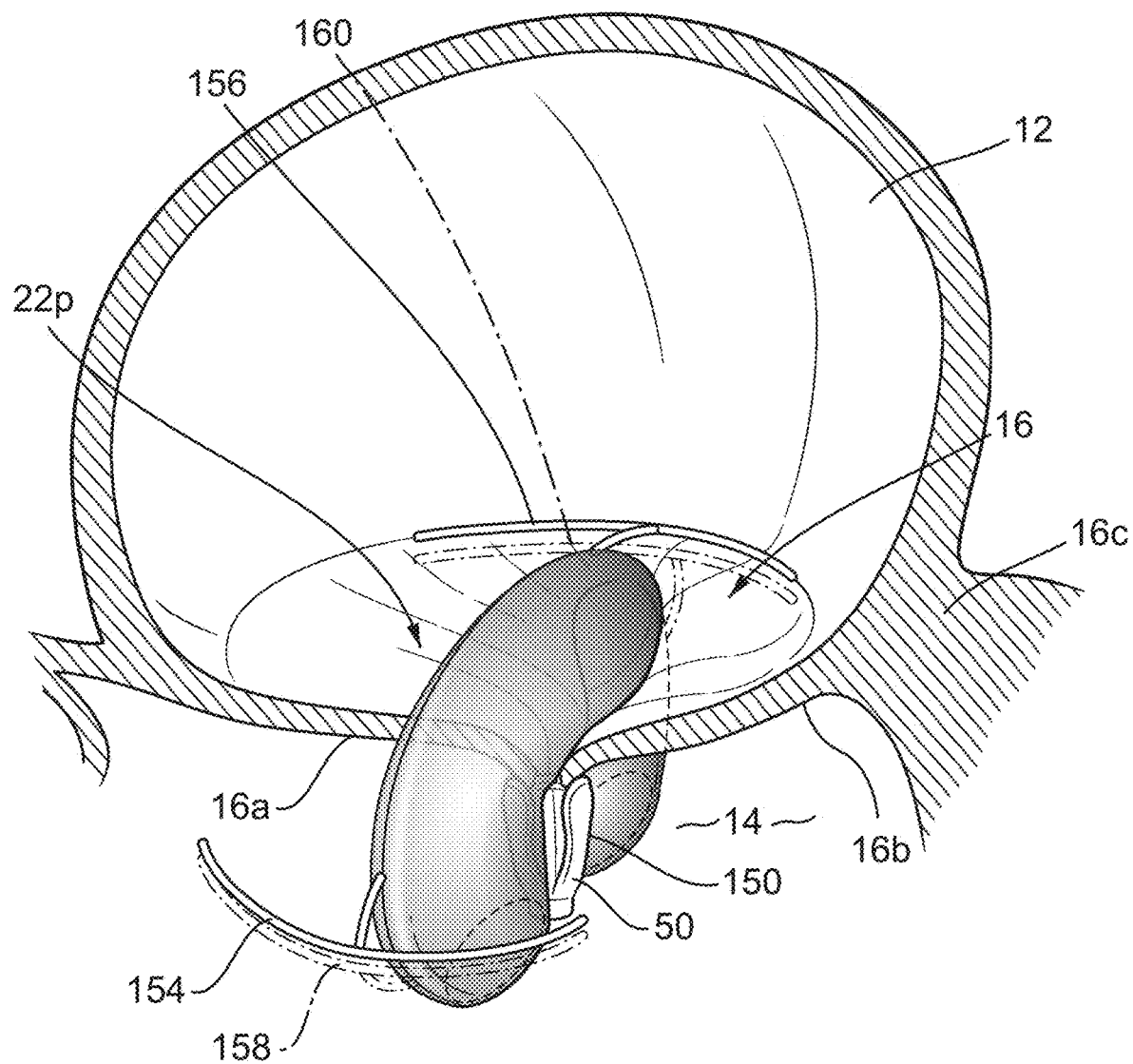
FIG. 22E is a view similar to FIG. 22D, but illustrating an alternative frame structure attached to the selective occlusion device.

FIG. 22E illustrates another embodiment, similar to that shown in FIG. 22D, but further illustrating respective annulus connectors 154, 156 as part of the selective occlusion device 22*p* in the form of frame members that bear against heart tissue generally at the annulus 16*c* in the left atrium 12 and, additionally or optionally, frame members or connectors 158, 160 (shown in broken lines) coupled with the selective occlusion device 22*p* and located in the left ventricle 14 abutting the annulus 16*c* from below. Use of both sets of annulus connectors 154, 156, 158, 160 results in sandwiching the heart tissue therebetween for better securement.

Figure 22F:
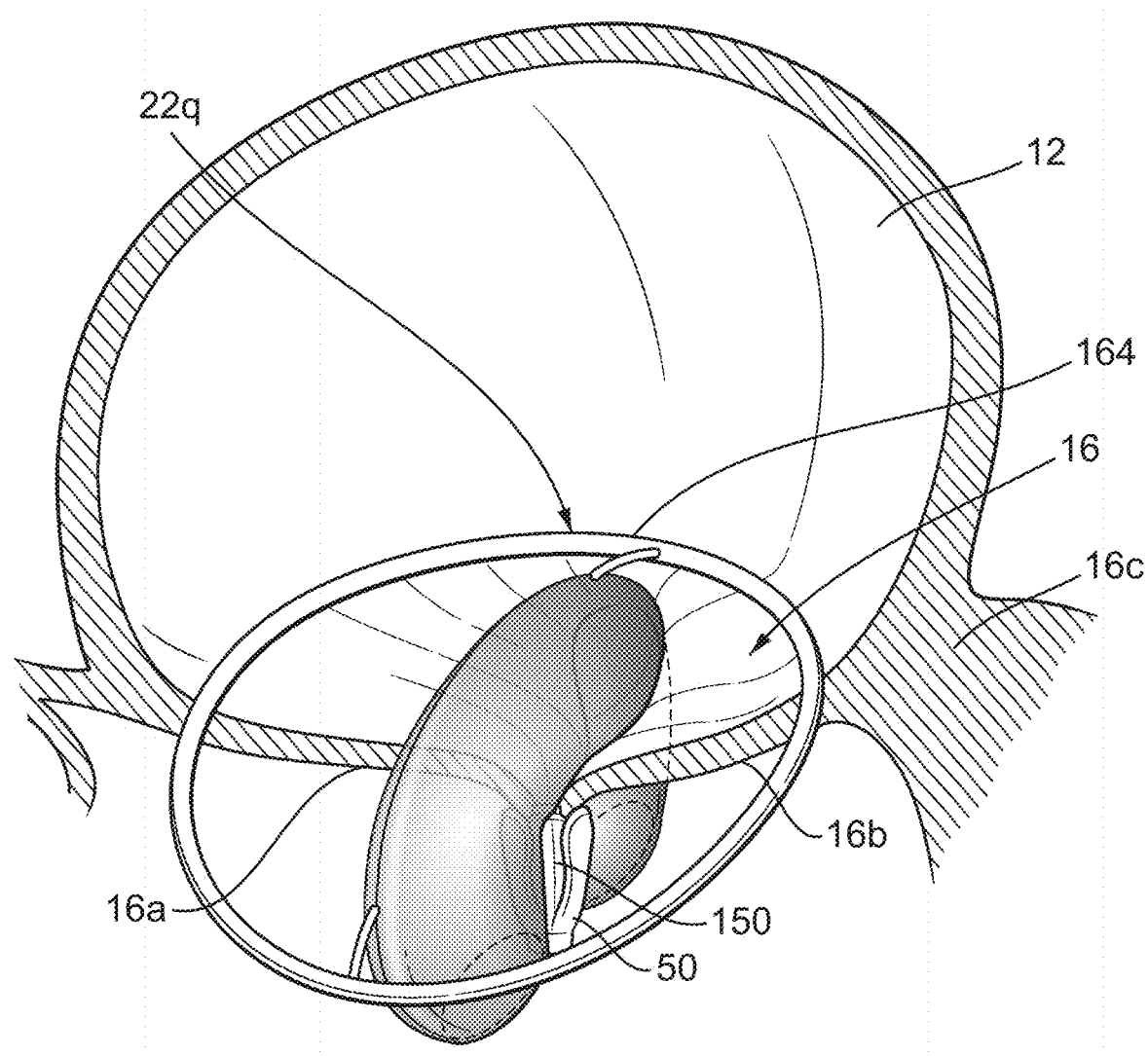
FIG. 22F is a view similar to FIG. 22E, but illustrating another alternative frame structure.

FIG. 22F illustrates another embodiment of a device 22*q*, similar to FIG. 22E, but illustrating a single annular connector 164 generally encircling the native mitral valve 16 formed as part of the selective occlusion device and anchoring the selective occlusion device 22*q* in the native mitral valve 16 securely, preventing rocking in any direction but allowing flexibility. As with all embodiments, the frame members may be formed of any desired material, such as flexible wire-like materials formed from polymers and/or flexible metals including super-elastic or shape memory materials. This can help achieve overall goals of the embodiments of flexibility for collapsed delivery and improved operation during implanted use, as well as resistance against failure due to fatigue in this application involving continuous cycling in the heart.

Figure 22G:
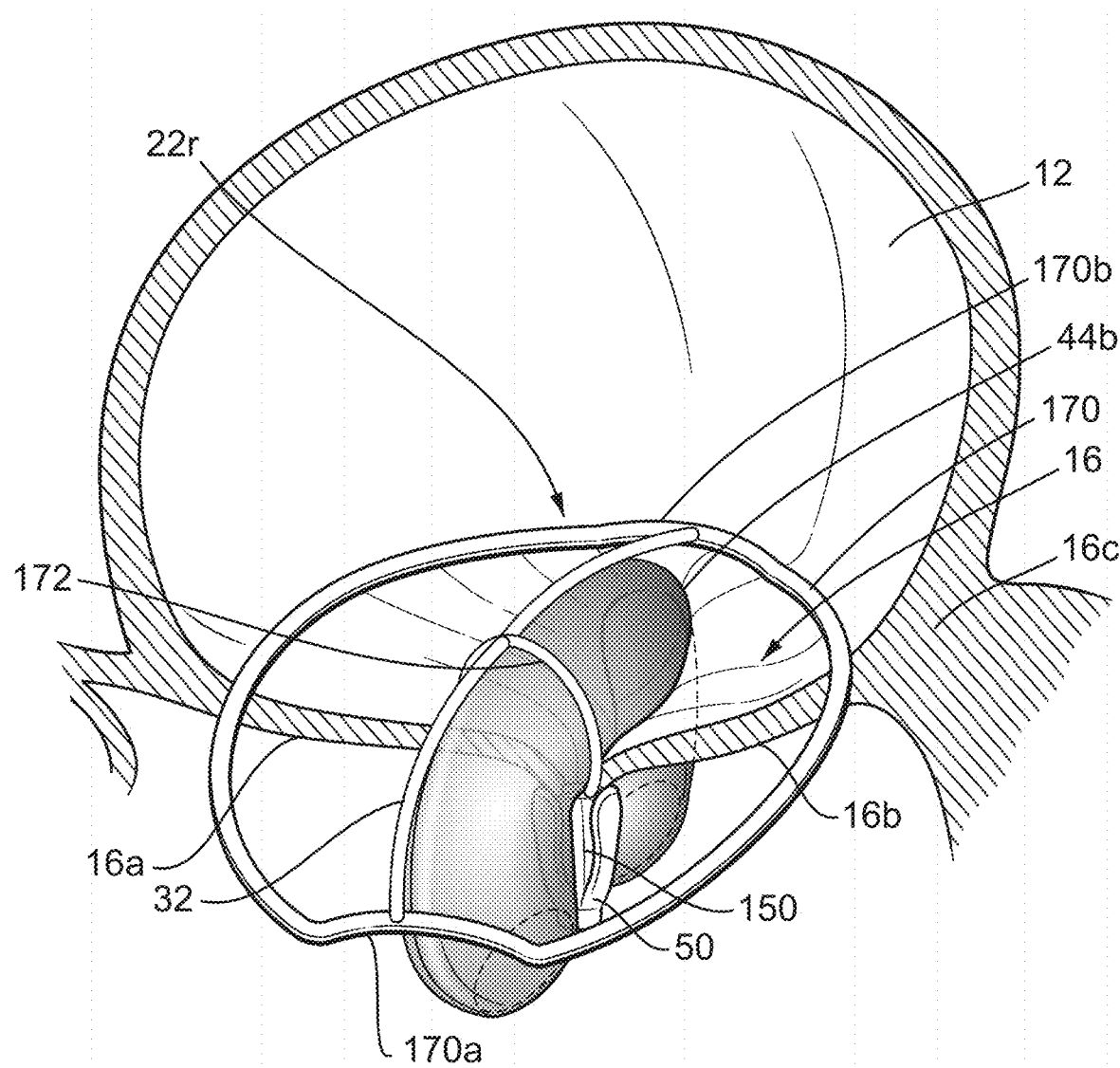
FIG. 22G is a view similar to FIG. 22F, but illustrating another alternative frame structure.

FIG. 22G illustrates another embodiment of a device 22*r*. The selective occlusion device 22*r* may be as described in connection with any other embodiment, but for illustrative purposes, is shown with a hollow flexible membrane 44*b*, while the frame structure has been modified as shown. The frame structure includes a generally annular frame member 170 such as described and shown in connection with FIG. 22F, but including raised portions 170*a*, 170*b* relative to other portions. The raised portions 170*a*, 170*b* are configured to be located adjacent and above the commissures of the native mitral valve 16 and are connected with a central frame member 32 extending generally across the native mitral valve 16 and formed as part of the selective occlusion device 22*r* such as with another connecting frame member 172. Such frame members at the annulus, as with all embodiments, may be above the annulus, below the annulus, or frame members/connectors may be above and below the annulus to sandwich tissue therebetween.

Figure 23A:
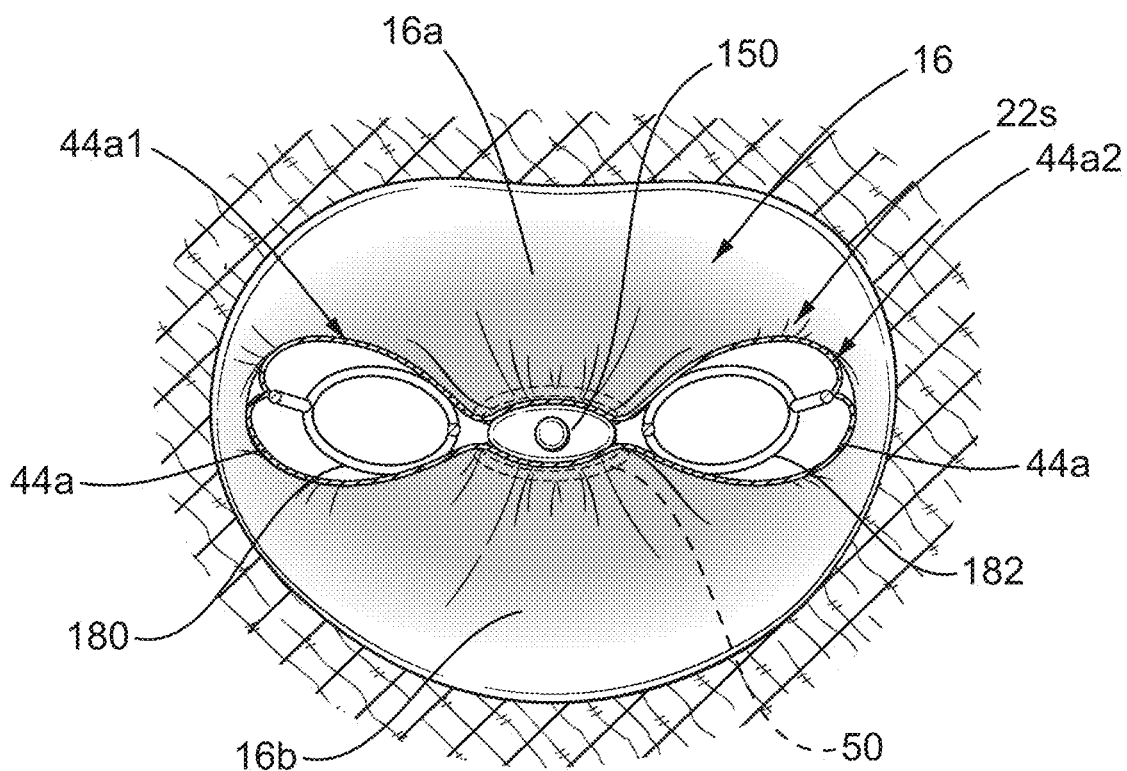
FIG. 23A is a cross-sectional view of a native mitral valve and another embodiment of a heart valve repair apparatus, shown with the heart in the systole phase.
Figure 23B:
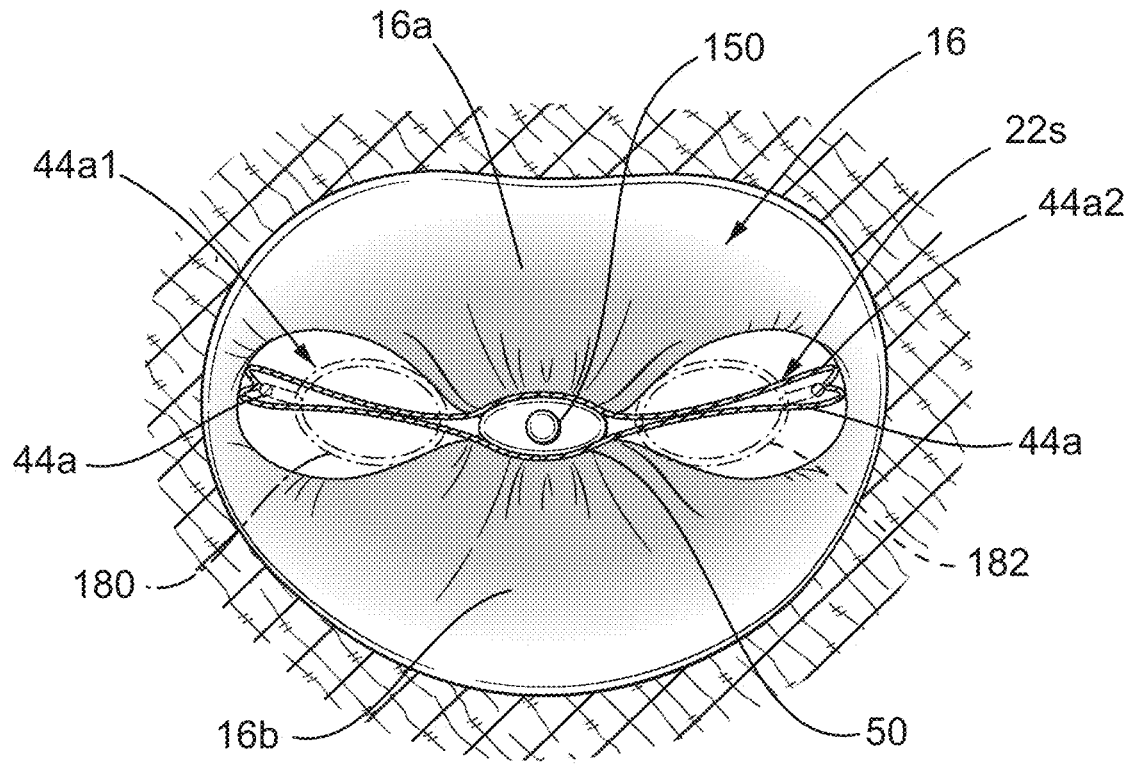
FIG. 23B is a view similar to FIG. 23A, but illustrating the apparatus and the mitral valve when the heart is in the diastole phase.

FIGS. 23A and 23B schematically illustrate a selective occlusion device 22*s* coupled with a central clip 50 including a spacer 150 implanted in a mitral valve 16. FIG. 23A illustrates the device 22*s* and the mitral valve 16 when the heart cycle is in systole, while FIG. 23B illustrates the mitral valve 16 and the selective occlusion device 22*s* when the heart is in diastole. The frame structure includes respective hoops or rings 180, 182 as shown in solid lines in FIG. 23A and broken lines in FIG. 23B. These define the openings 140, 142. A benefit of this frame configuration is that the frame will not contact the commissures during repeated heart cycling. The device, like other embodiments allows blood flow from the left atrium to the left ventricle in diastole but prevents blood flow during systole.

Figure 24:
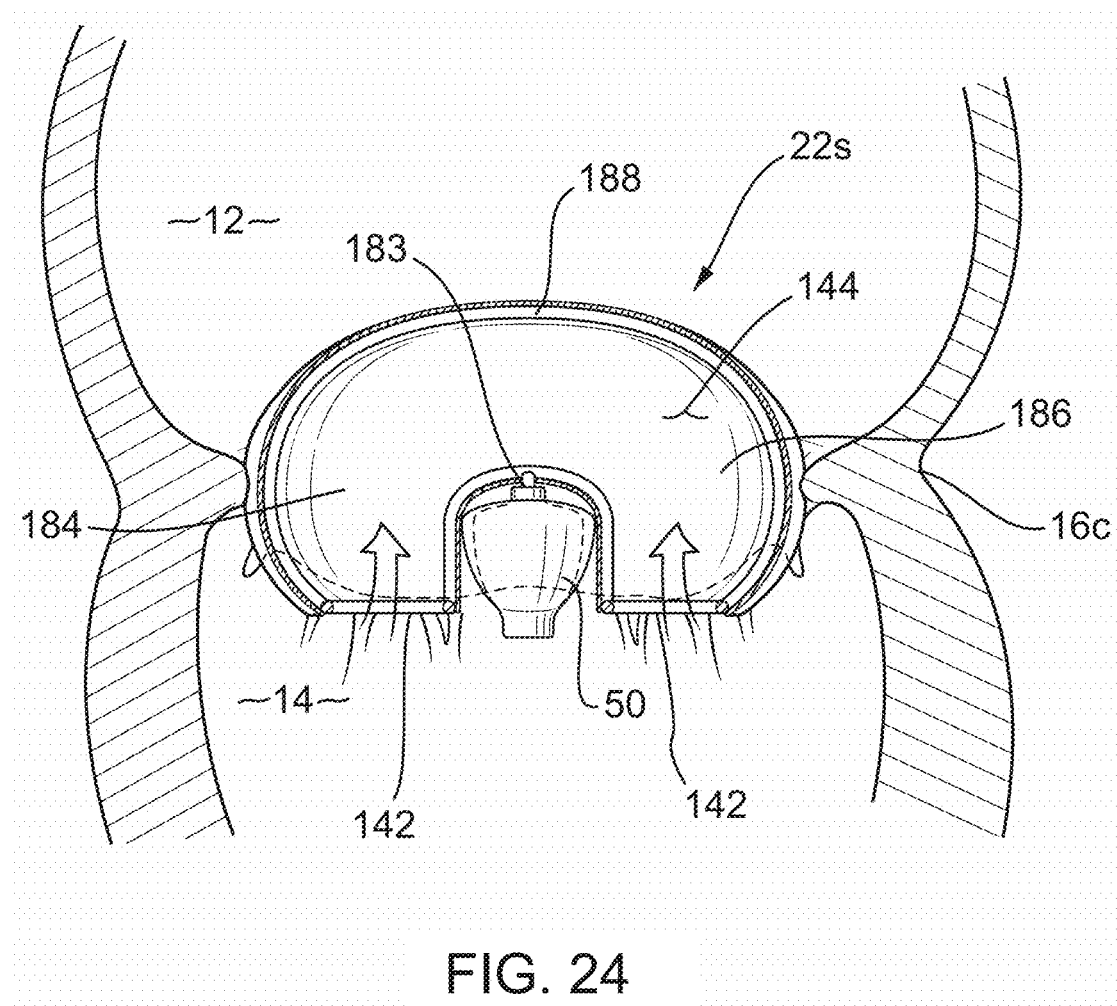
FIG. 24 is a side cross-sectional view of another alternative embodiment of a heart valve repair apparatus implanted in a native mitral valve.

FIG. 24 is a cross-sectional view schematically illustrating the mitral valve 16 and the implanted selective occlusion device 22s, coupled with a central clip structure 50 such as at a coupling 183. The selective occlusion device 22s is of a type with a hollow interior 144 having two fluid communicating sections 184, 186 and respective first and second openings 140, 142 and a closed end 188. Fluid communication between sections 184, 186 allows for better rinsing and washing action and reduced chance of clotting.

Figure 25A:
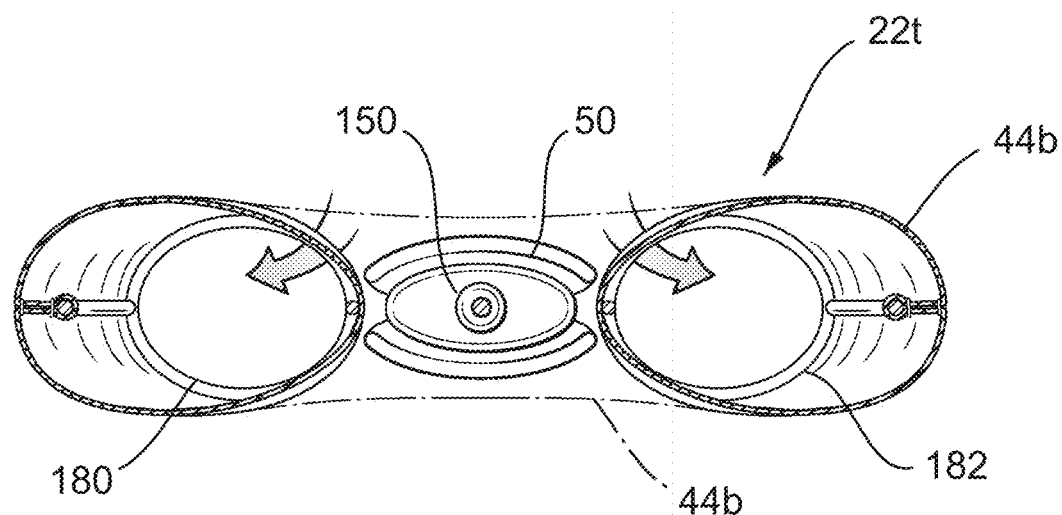
FIG. 25A is a cross-sectional view of another alternative embodiment of a heart valve repair apparatus.
Figure 25B:
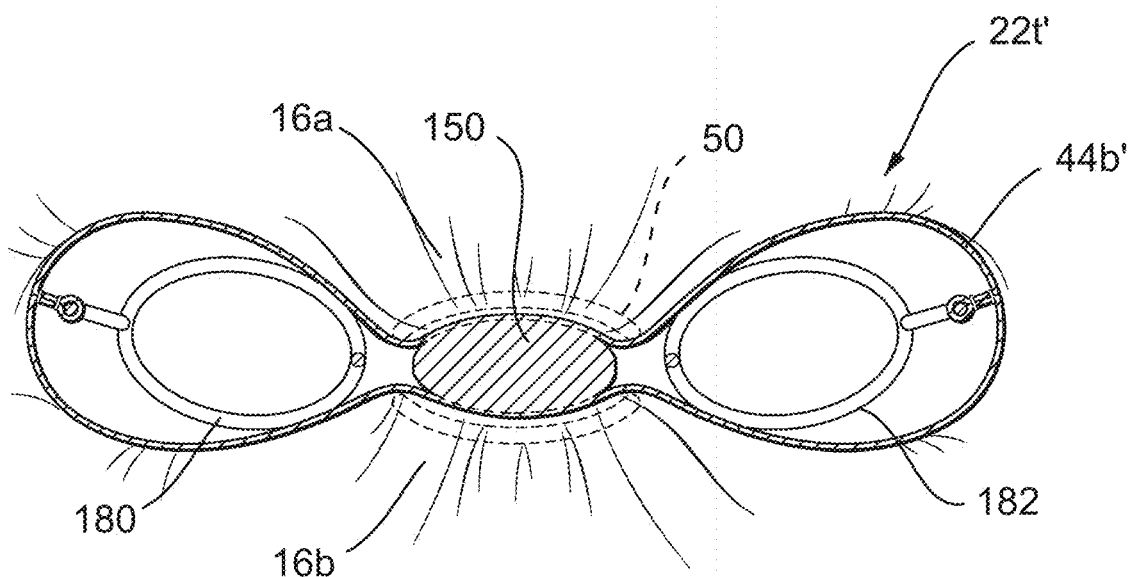
FIG. 25B is a cross-sectional view of another alternative embodiment of a heart valve repair apparatus implanted in a native mitral valve.

FIGS. 25A and 25B are schematic views of a selective occlusion device 22t, 22t' including a flexible membrane 44b, 44b' with FIGS. 25A and 25B showing the selective occlusion devices 22t, 22t' when the heart cycle is in systole. The difference between the two devices 22t, 22t' is that the flexible membrane 44b' is integrated into the spacer 150 of the clip structure 50, while the flexible membrane 44b is not. Flexible membrane 44b and/or another portion, such as a frame portion, of device 22t may be otherwise coupled to clip structure 50 such as in the manner shown in FIG. 24 or another suitable manner.

Figure 26A:
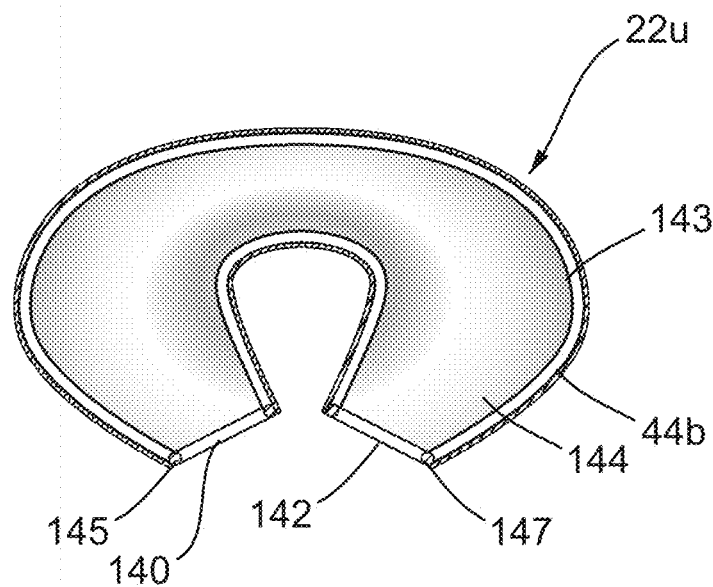
FIG. 26A is another alternative embodiment of a selective occlusion device shown in cross-section.
Figure 26B:
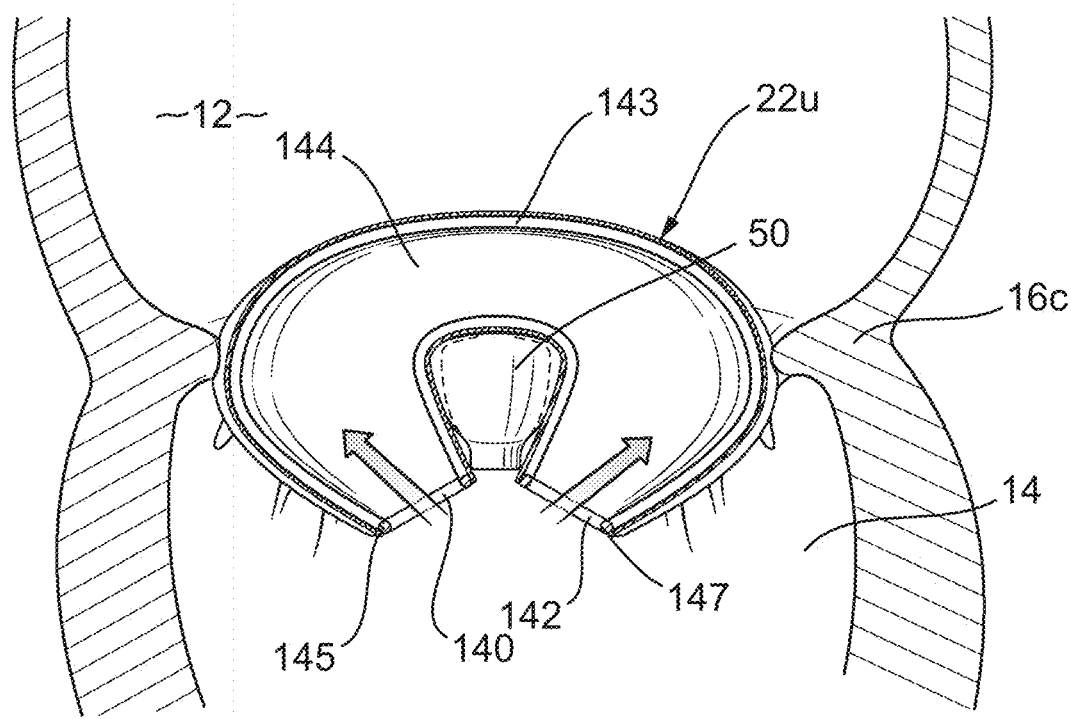
FIG. 26B is a schematic view illustrating the device of FIG. 26A implanted in a native mitral valve.
Figure 26C:
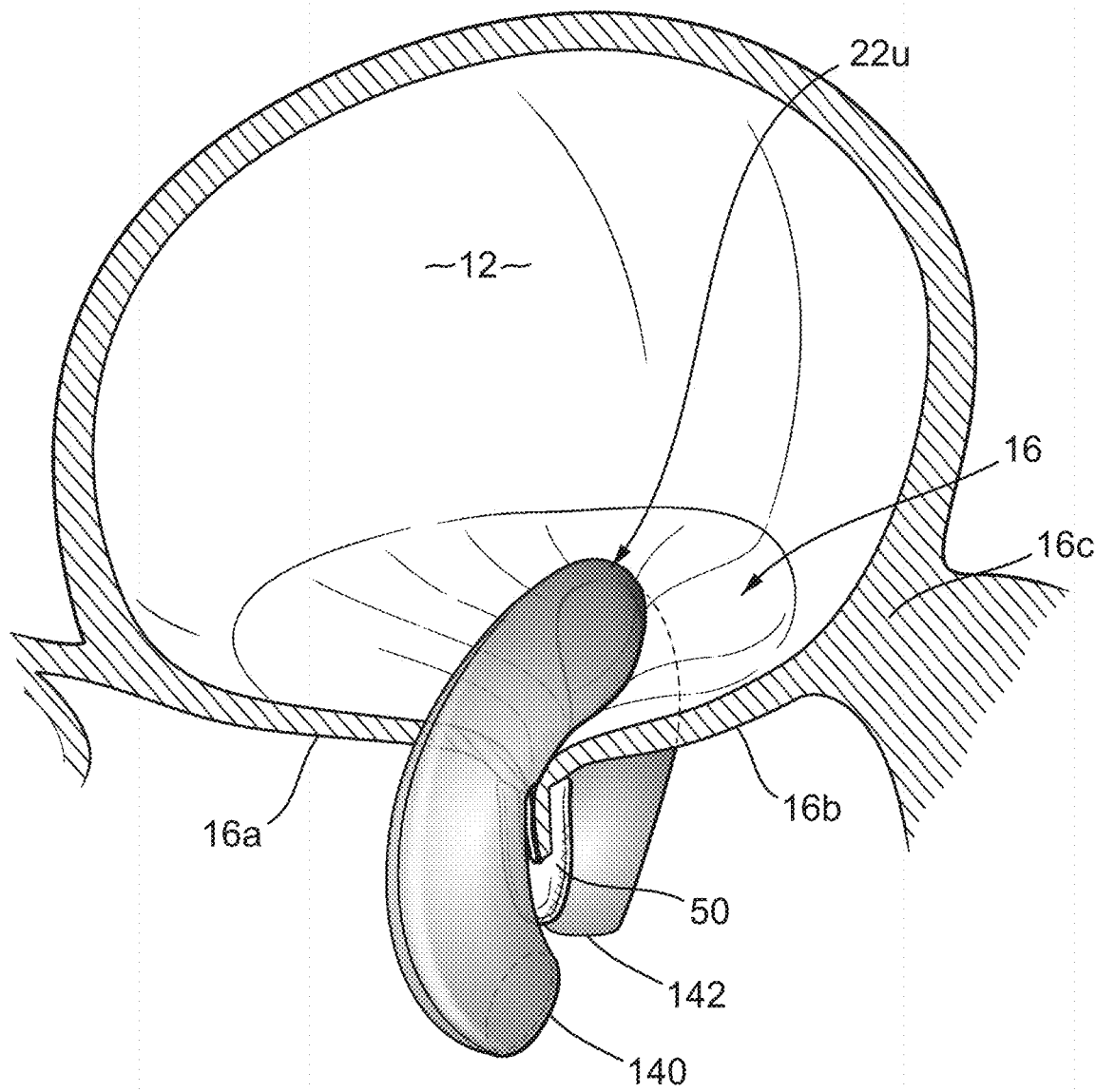
FIG. 26C is a perspective view illustrating the device of FIGS. 26A and 26B implanted in a native mitral valve.

FIGS. 26A, 26B and 26C schematically illustrate another illustrative embodiment of an apparatus including a central clip structure 50 (FIG. 26B) and a selective occlusion device 22u. The selective occlusion device 22u, as with previous devices shown and described herein, is a hollow fluid communicating structure having a flexible membrane 44b and allowing blood flow into the hollow interior 144 defined by the flexible membrane 44b in systole, as shown in FIGS. 26B and 26C. In diastole, the flexible membrane 44b collapses inwardly, as previously shown and described, to allow blood flow past the selective occlusion device 22u and between the native mitral leaflets 16a, 16b from the left atrium 12 into the left ventricle 14. In this embodiment, the orientation of openings 140, 142 and shape of the device 22u force blood flow, in systole, toward the commissure regions as shown by the arrows. These forces help retain the device 22u in place, in addition to any other securement such as the clip structure 50. In this way, rocking of the device 22u may be reduced and the device 22u can be more stable during implantation and use. These inlets 140, 142 are angled acutely away from the central clip structure 50 as shown in FIG. 26B.

Figure 26D:
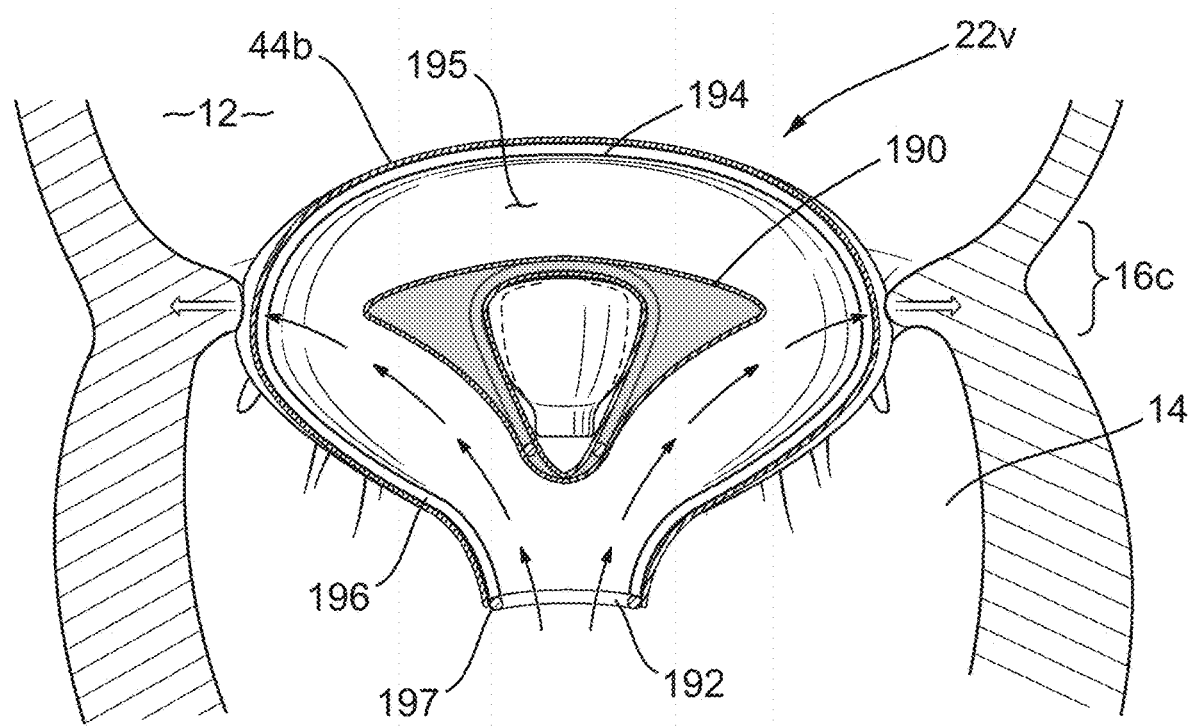
FIG. 26D is a cross-sectional view of another alternative heart valve repair apparatus implanted in a native mitral valve.

FIG. 26D illustrates another embodiment of a selective occlusion device 22v in which a suitable baffle structure 190 is provided within the selective occlusion device 22v for directing blood flow outwardly as shown by the arrows toward the connecting locations between the device 22v and the mitral annulus 16c. This helps to produce securement force and stabilization of the device 22v in the implanted condition. A single opening 192 is provided for in flow during systole and the device 22v includes a closed end 194 and a hollow interior 195, such that the device 22v fills with blood during systole and collapses to expel the blood during diastole as previously shown and described. A frame structure 196 is provided to support a flexible membrane 44b, generally as previously described, except that the frame structure is shaped and configured differently so as to form the single opening 192 defined by a hoop or ring frame member 197. It will be appreciated that the shapes and configurations of these structures may be modified from those shown in these illustrative examples.

Figure 26E:
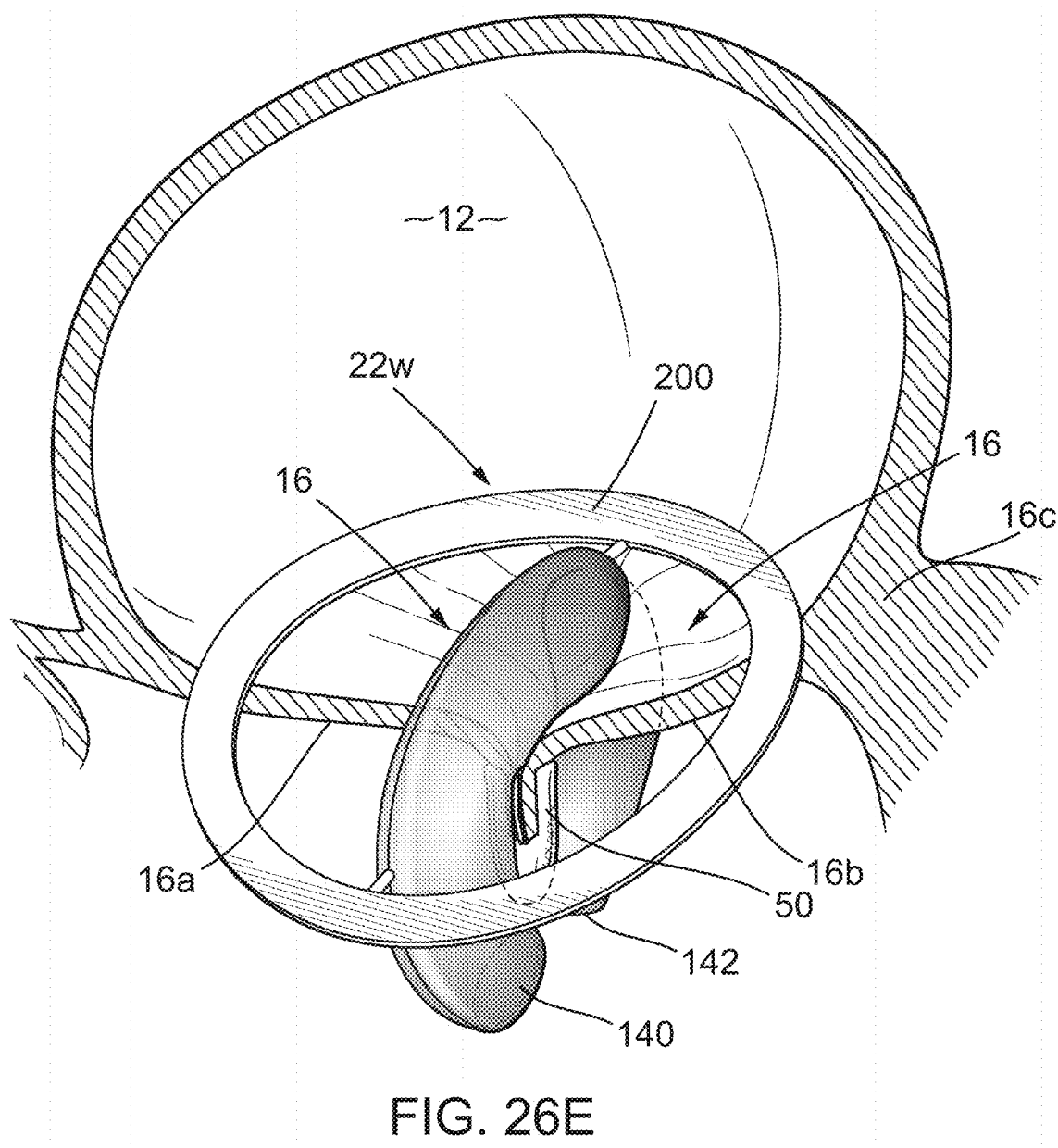
FIG. 26E is a cross-sectional view of another alternative heart valve repair apparatus implanted in a native mitral valve.

FIG. 26E is an embodiment of a device 22w that may be configured as previous embodiments have been described, in terms of the selective occlusion device 22w, but which includes a generally annular or circular frame 200 structure that is a flat element for securing the apparatus in place in the mitral valve 16. The frame structure 200 is shown to rest and/or be secured in the left atrium 12 abutting against heart tissue generally proximate the mitral annulus 16c. However, it will be appreciated that such a structure could be secured in other manners, and that an additional lower support may be provided to sandwich heart tissue therebetween.

Figure 27A:
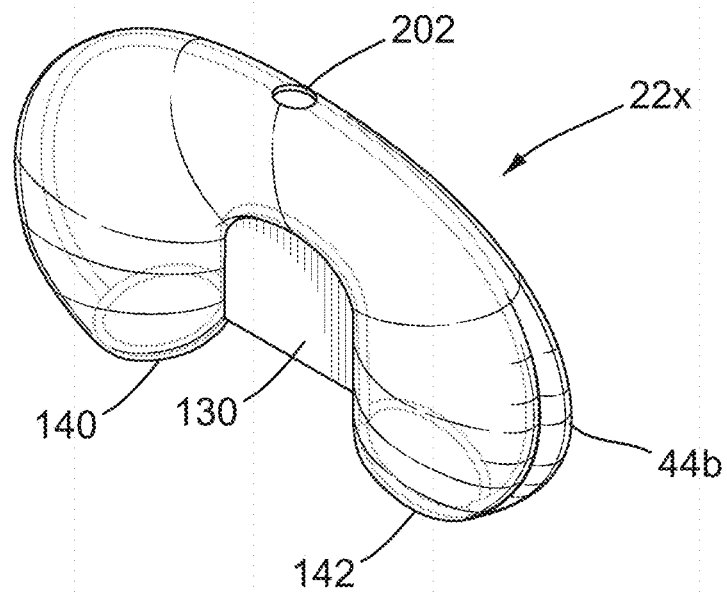
FIG. 27A is a perspective view of another alternative selective occlusion device.
Figure 27B:
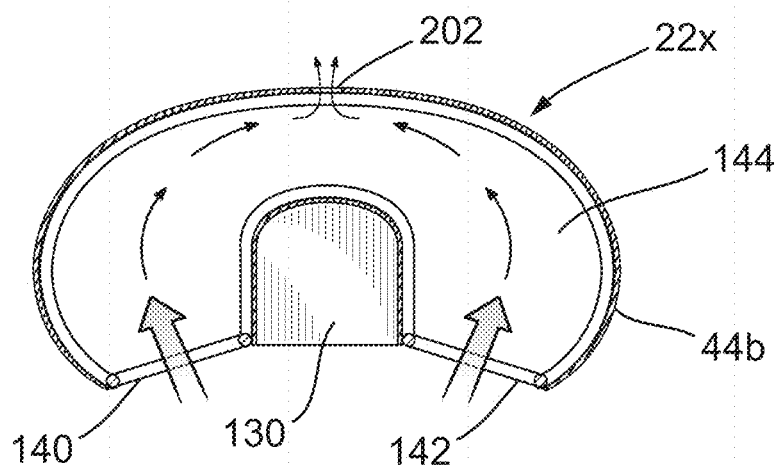
FIG. 27B is a lengthwise cross-sectional view of the device shown in FIG. 27A, schematically illustrating blood flow during the systole phase of the heart.
Figure 27C:
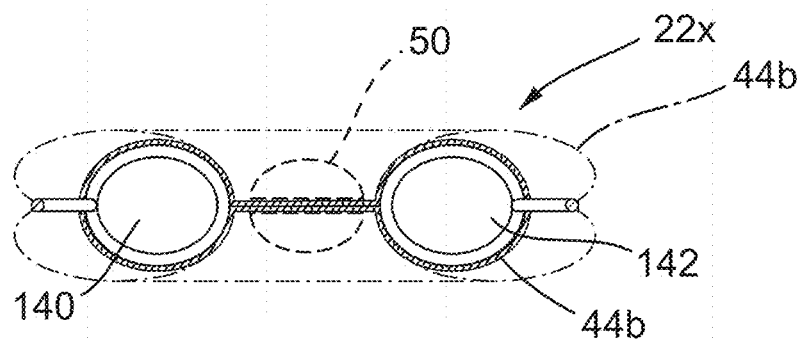
FIG. 27C is a transverse cross-sectional view illustrating the device of FIGS. 27A and 27B during systole.

FIGS. 27A through 27C illustrate another embodiment of a selective occlusion device 22x which may be constructed in accordance with previous described embodiments, but including at least one small vent 202 opposite to the two openings 140, 142 of the flexible membrane 44b. The vent 202 is not large enough to result in any significant regurgitation or leakage of blood in systole. To the extent that the vent 202 does not allow any significant regurgitation of blood, this end of the flexible membrane is closed while the opposite end includes at least one and, in this embodiment two openings 140, 142. Otherwise, this embodiment of the flexible membrane 44b operates and functions for purposes and in ways as previously shown and described. One or more vents 202 may, for example, provide a pressure relief to reduce the forces against the device 22x during high pressure systole portions of the heart cycle.

Figure 28A:
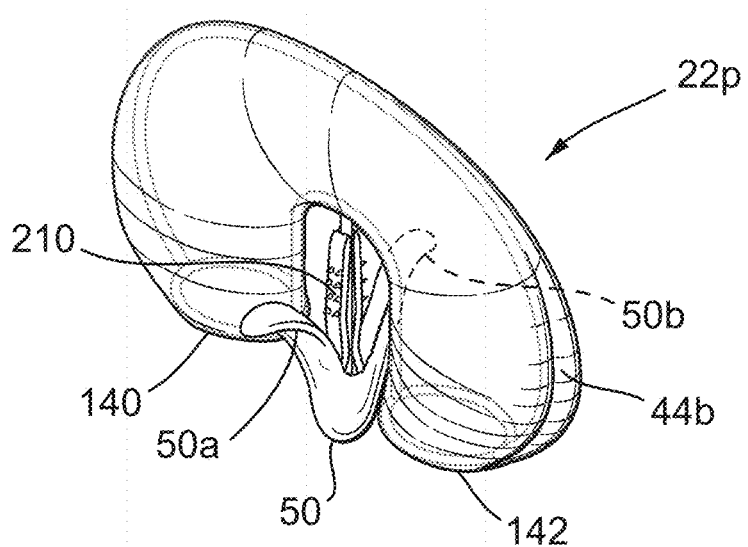
FIG. 28A is a perspective view illustrating another alternative embodiment of another apparatus including a selective occlusion device together with a mitral valve clip structure.
Figure 28B:
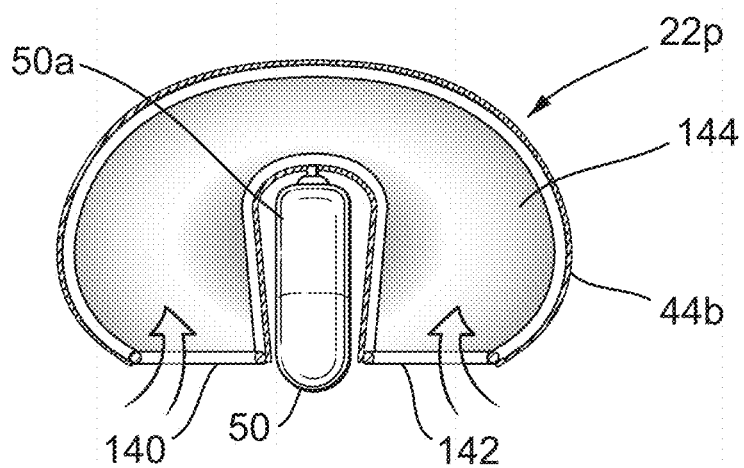
FIG. 28B is a lengthwise cross-sectional view illustrating the device and clip structure shown in FIG. 28A.
Figure 28C:
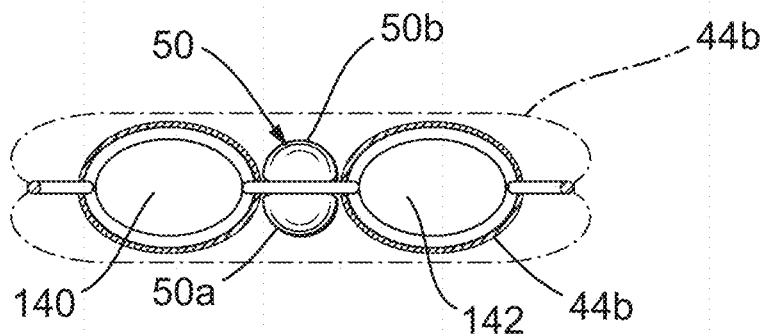
FIG. 28C is a transverse cross-sectional view illustrating the device of FIGS. 28A and 28B.

FIGS. 28A through 28C illustrate another embodiment of an apparatus comprised of a central clip structure 50 and the previously described selective occlusion device 22p. In this embodiment, the clip structure 50 includes a central gripping structure 210 which may have tines or other knurled, roughened or frictional surfaces. This will assist with clamping and retaining mitral leaflet margin tissue between the respective clip elements 50a, 50b and the selective occlusion device 22p. The clip structure 50 is secured to the selective occlusion device 22p, such as via the central gripping element 210. FIGS. 28B and 28C further illustrate that the selective occlusion device 22p operates in the same manner, for example, as described above with fluid communication between two generally adjacent openings 140, 142 for increased washing and rinsing.

Figure 29A:
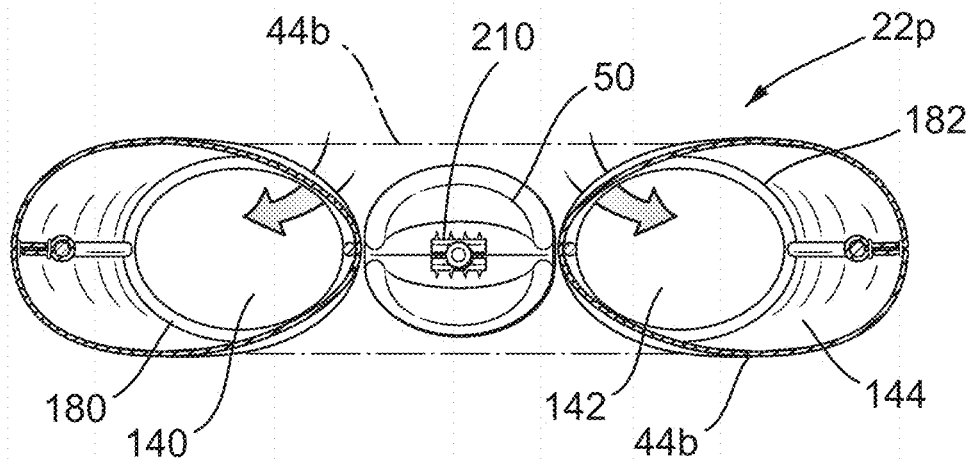
FIG. 29A is a cross-sectional view of a selective occlusion device and clip structure schematically illustrating blood flow between the interior membrane wall surfaces during the heart systole phase.
Figure 29B:
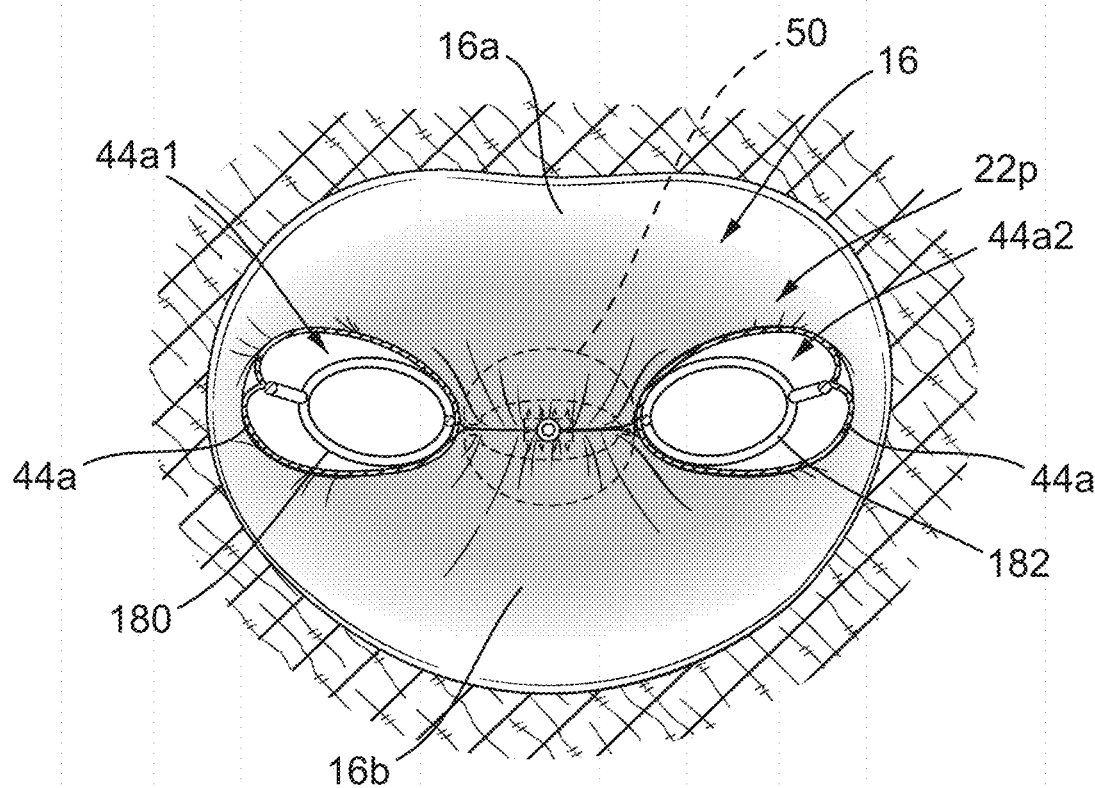
FIG. 29B is a cross sectional view of the apparatus of FIG. 29A implanted in the native mitral valve and illustrating the device and the mitral valve when the heart is in the systole phase.
Figure 30:
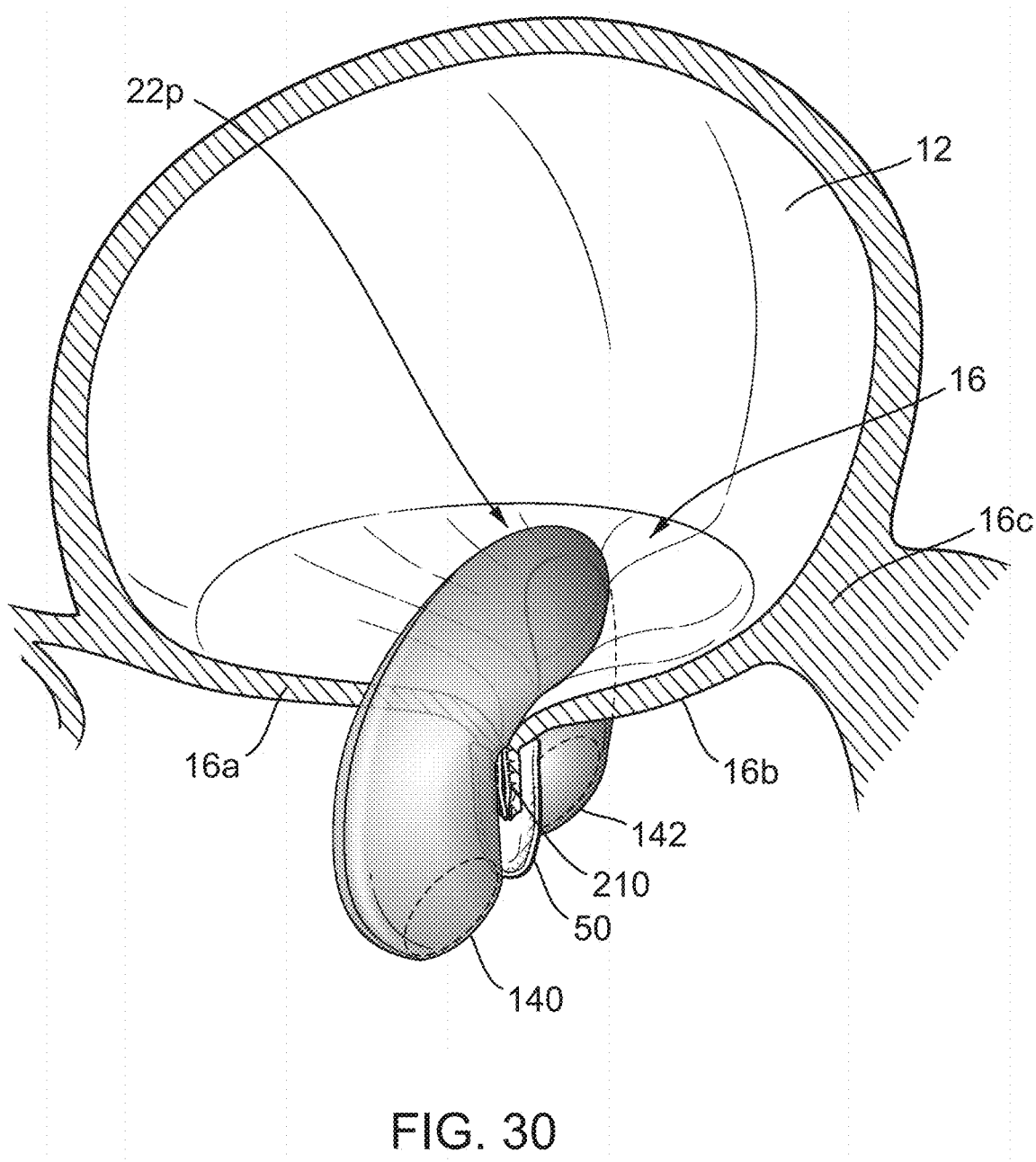
FIG. 30 is a perspective view illustrating the mitral valve in cross-section and the fully implanted selective occlusion device and clip structure.

FIGS. 29A, 29B and 30 illustrate the apparatus shown in FIGS. 28A through 28C in operation after being implanted in the mitral valve 16. Specifically, blood enters the selective occlusion device 22p through the open ends 140, 142 and fills the interior 144 defined by the flexible membrane 44b, whereupon the flexible membrane 44b expands or inflates to engage in contact with the native mitral leaflets 16a, 16b forming a fluid seal that prevents regurgitation of blood flow during systole (FIGS. 29A and 29B). This is shown in FIG. 29B with the anatomy of the mitral valve 16 further shown and the native leaflet tissue contacting the outside surfaces of the flexible membrane 44b during systole.

Figure 31:
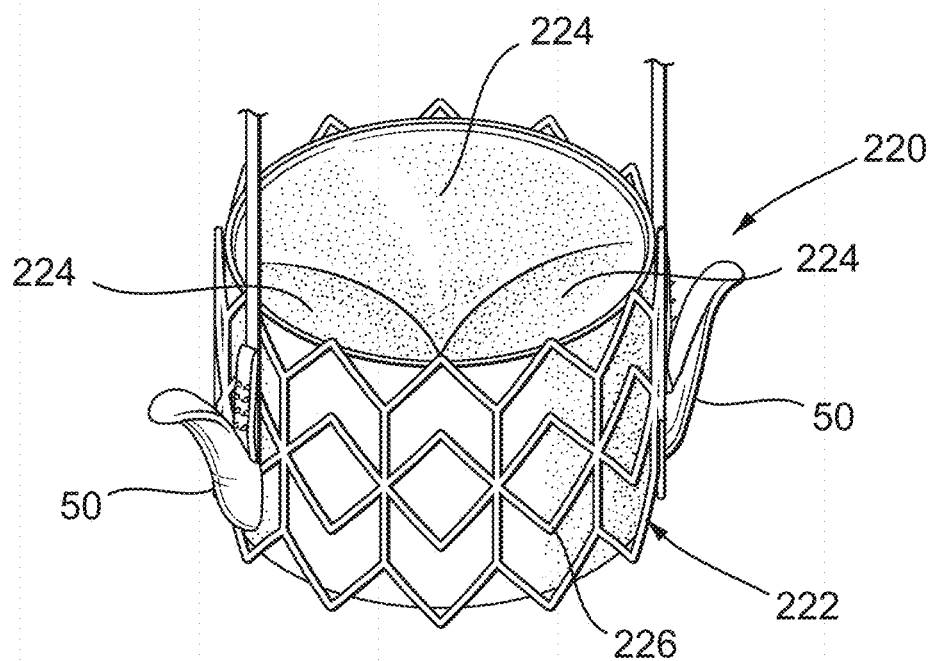
FIG. 31 is a perspective view of another alternative embodiment illustrating a prosthetic heart valve and leaflet clip structures.
Figure 32A:
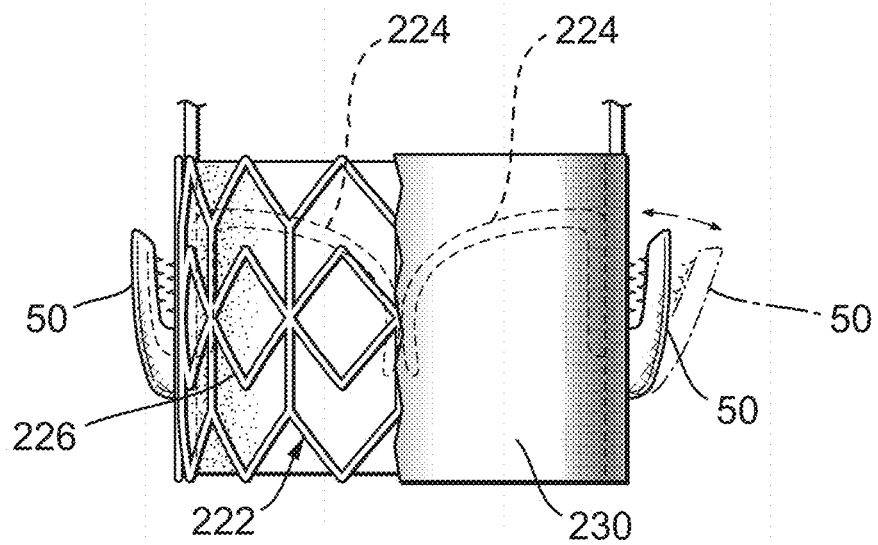
FIG. 32A is a side elevational view, partially fragmented to show the prosthetic heart valve and leaflet clip structures.

FIG. 31 illustrates another embodiment showing an expandable prosthetic heart valve 220, which may be comprised of a generally cylindrical outer or peripheral frame structure 222 and coupled with interior prosthetic leaflets 224 that open and close to control blood flow therethrough. This is different from the other versions of a selective occlusion device which have at least one movable valve element (e.g., the flexible membrane that operates in conjunction with a native mitral leaflet), in that this prosthetic heart valve 220 does not operate in conjunction with the native leaflet to control blood flow. Instead, the prosthetic leaflets 224 control blood flow through the prosthetic valve 220. Coupled to the frame structure 222 are clip structures 50 or elements that directly couple the expandable prosthetic heart valve 220 to heart valve leaflets, such as the mitral valve leaflets 16a, 16b as previously shown and described. FIG. 32A is a side elevational view partially fragmented to show the internal stent structure 226 exposed underneath an outer covering 230, which may be natural, synthetic, biologic, bioengineered, or any other suitable medical grade material useful for cardiac devices of this type.

Figure 32B:
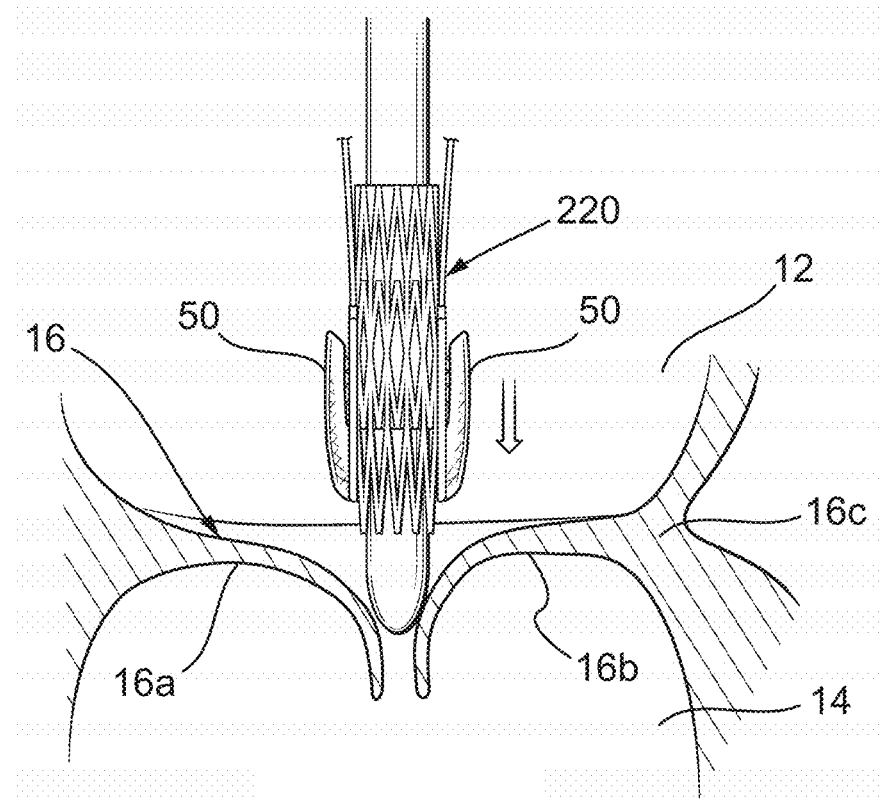
FIG. 32B is a side elevational view with the native heart valve in cross-section, illustrating an initial portion of the implantation procedure associated with the prosthetic heart valve of FIGS. 31 and 32A.
Figure 32C:
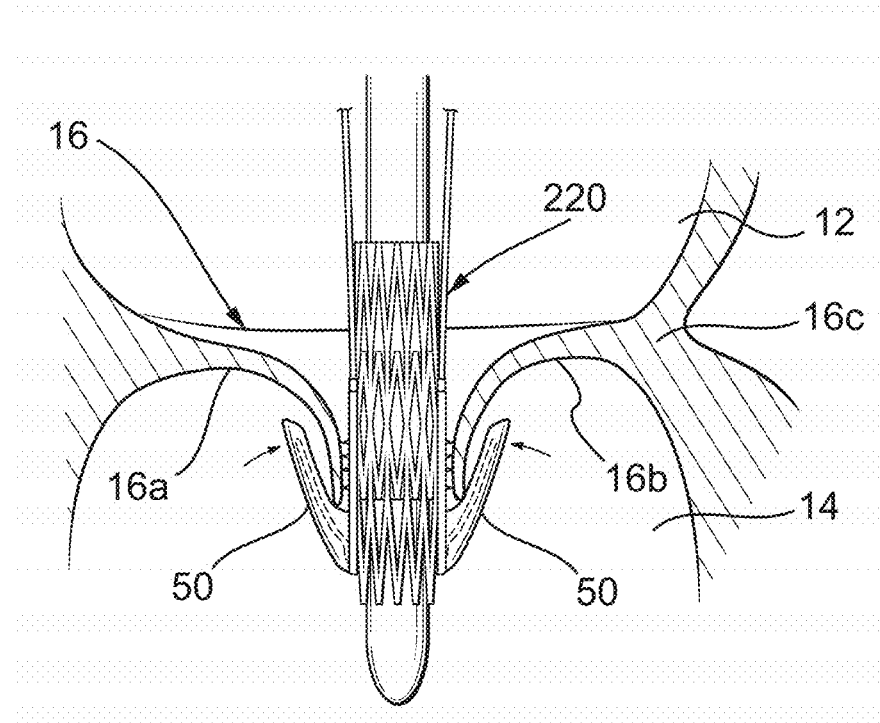
FIG. 32C is a view similar to FIG. 32B, but illustrating a subsequent step in the method.
Figure 32D:
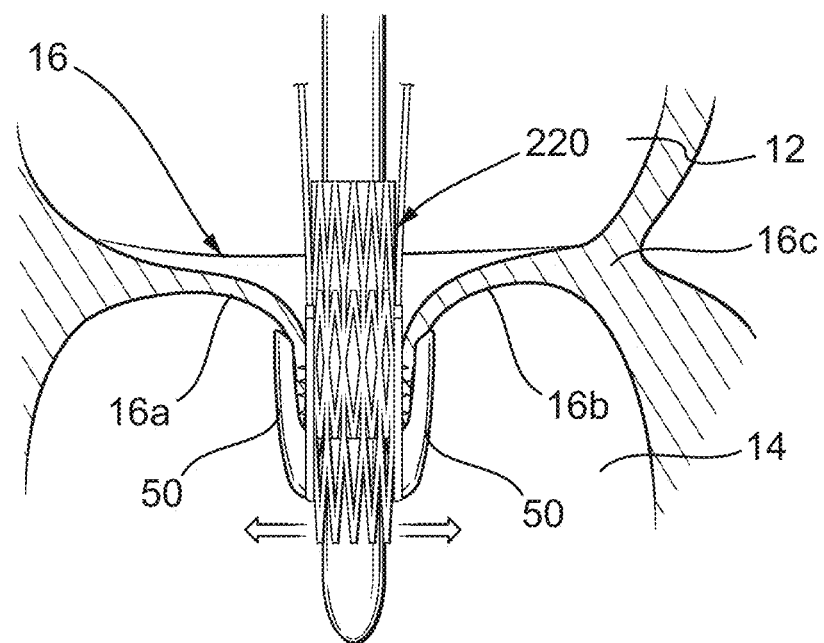
FIG. 32D is a view similar to FIG. 32C, but illustrating a subsequent step in the method.
Figure 32E:
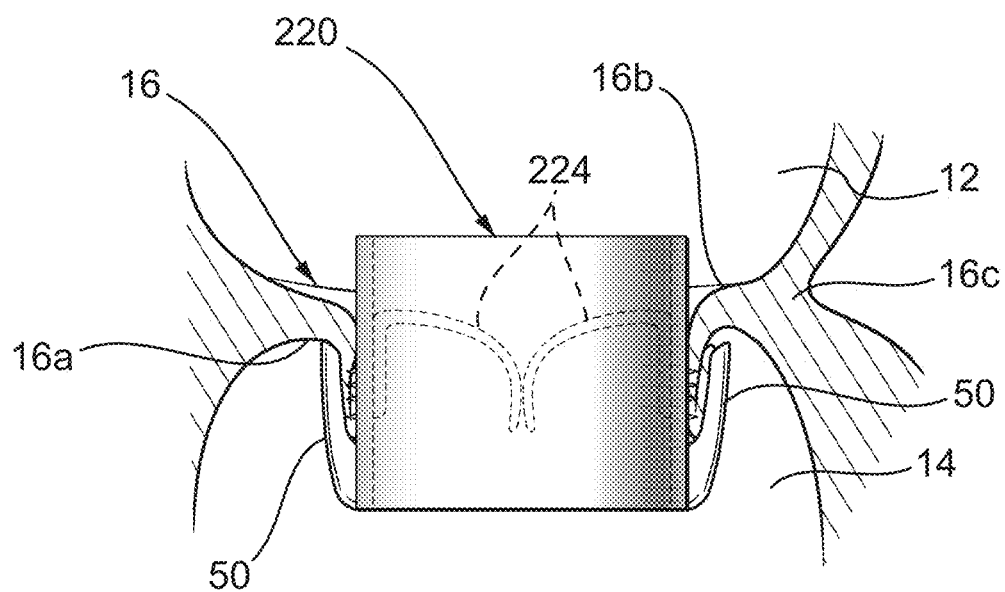
FIG. 32E is a view similar to FIG. 32D, but illustrating the fully implanted prosthetic heart valve clipped to the native heart valve leaflets and expanded into an implanted condition.

FIGS. 32B through 32E illustrate the succession of steps used to implant the prosthetic valve 220 of FIGS. 31 and 32A. In particular, this apparatus may be implanted through a transcatheter procedure, or a more invasive procedures such as a surgical procedure or keyhole type or other less invasive procedure. The collapsed or folded apparatus 220 is inserted between the mitral valve leaflets 16a, 16b as shown in FIG. 32B, the clip structures 50 are used to capture the lower margins of the mitral leaflets 16a, 16b (FIG. 32C) and clamp them as shown in FIG. 32D. The expandable prosthetic heart valve 220 is then expanded against the native mitral leaflets 16a, 16b as shown in FIG. 32E to secure the implanted prosthetic heart valve 220 in place within the native mitral valve 16. The prosthetic leaflets 224 then open and close, respectively during diastole and systole to allow and prevent the flow of blood through the prosthetic heart valve 220.

Figure 33:
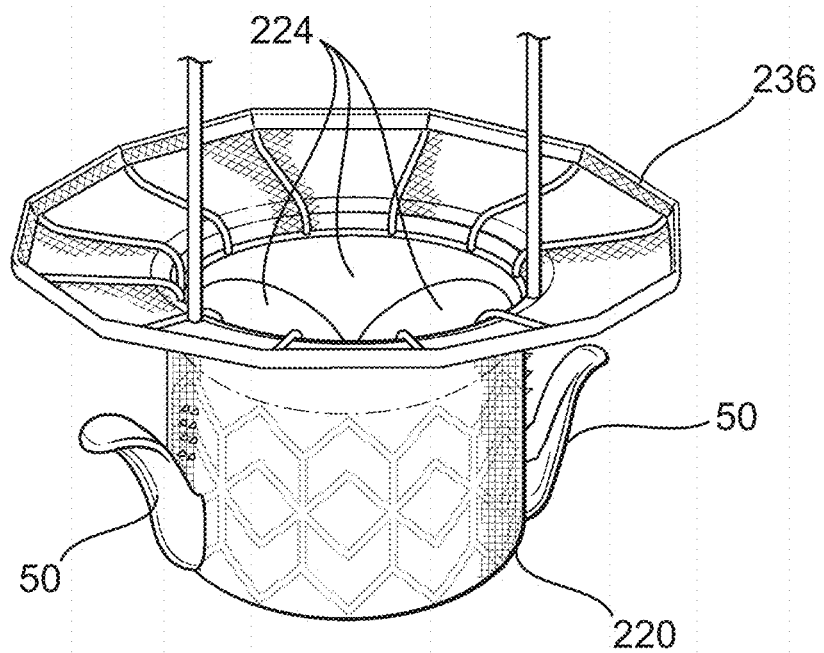
FIG. 33 is a perspective view of another alternative embodiment of a prosthetic heart valve and native leaflet clip structure.
Figure 34A:
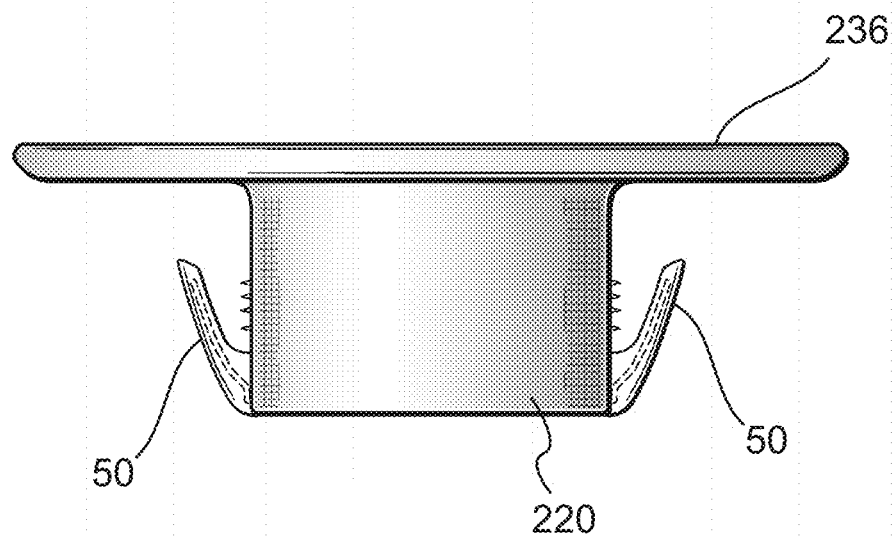
FIG. 34A is a side elevational view of the prosthetic heart valve illustrated in FIG. 33.
Figure 34B:
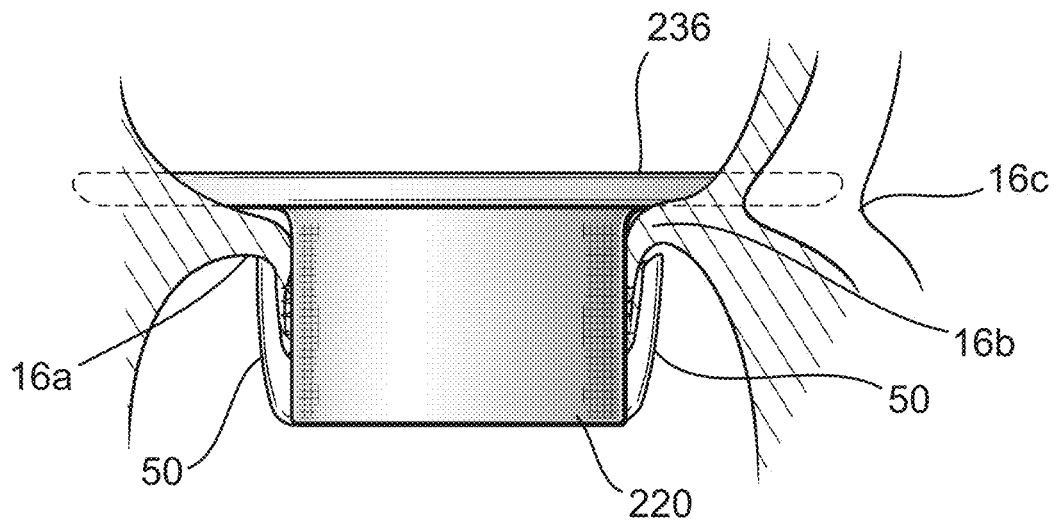
FIG. 34B is a view of the prosthetic heart valve of FIG. 34A implanted in a native heart valve.

FIG. 33 illustrates another embodiment, similar to the previous embodiment shown in FIG. 32, but adding an upper flange element 236 that helps secure the prosthetic heart valve 220 by stabilizing the heart valve 220 within the left atrium 12. In this regard the flange 236 is mounted above the native mitral valve 16. The flange 236 may abut against heart tissue in the lower portion of the left atrium 12. FIG. 34A is a side elevational view of the prosthetic heart valve 220 shown in FIG. 33. FIG. 34B is an illustration of the prosthetic heart valve 220 shown secured in place within the native mitral valve 16.

Figure 35A:
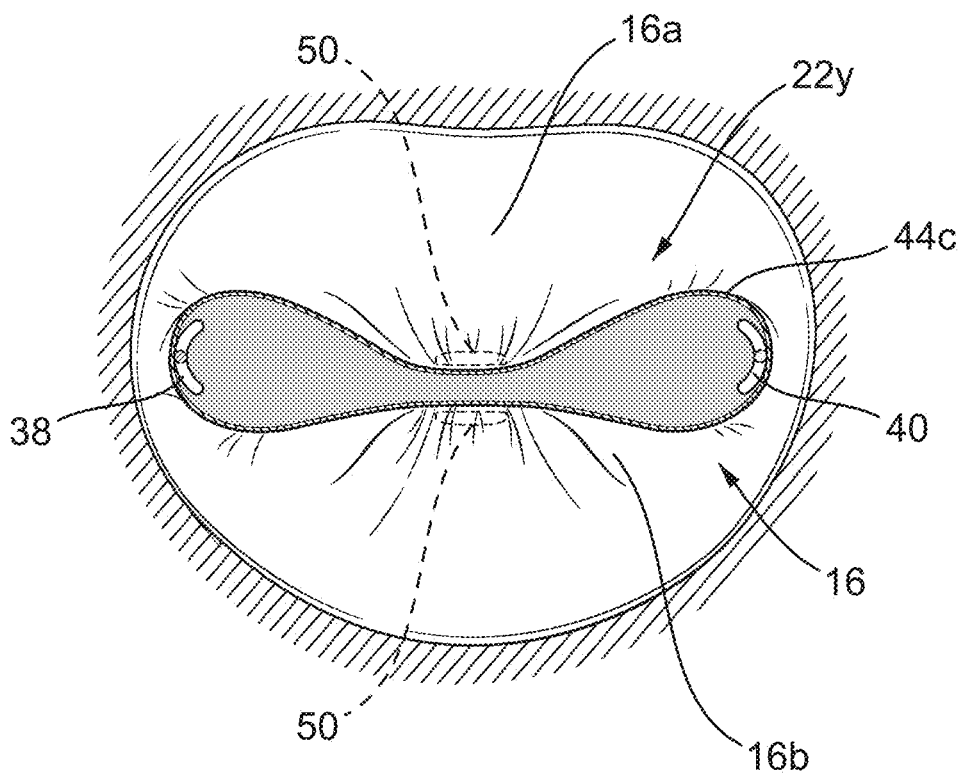
FIG. 35A is a cross sectional view similar to FIG. 29B, but illustrating another illustrative embodiment of a heart valve repair apparatus implanted in a mitral valve and showing the systole phase of the heart cycle.
Figure 35B:
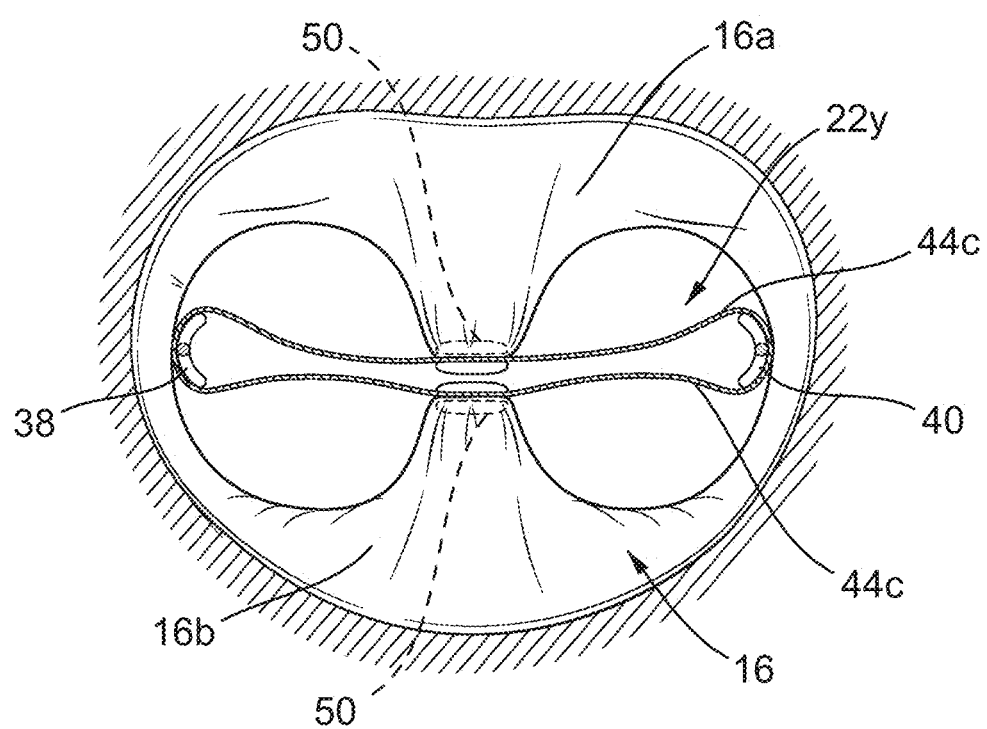
FIG. 35B is a cross sectional view similar to FIG. 35A, but illustrating the apparatus and mitral valve when the heart cycle is in the diastole phase.

FIGS. 35A and 35B show another embodiment of a selective occlusion device 22y mounted in a native mitral valve 16, as viewed in cross section. This embodiment includes a flexible membrane 44c with an open end facing the left ventricle 14, as in other embodiments, and receiving blood flow from below when the heart cycle is in systole (FIG. 35A). In this portion of the heart cycle, the flexible membrane 44c expands against the native leaflets 16a, 16b to reduce regurgitation as previously discussed. In diastole, the flexible membrane collapses and expels the blood therein (FIG. 35B). Blood then travels in the reverse direction, generally, through the mitral valve 16 by flowing between the native leaflets 16a, 16b and outer surfaces of the collapsed membrane 44c. A difference between this embodiment and others is that multiple clip structures 50 are used to secure the selective occlusion device 22y directly to the leaflets 16a, 16b. The leaflets 16a, 16b are not clipped to each other. It will be appreciated that even further clip structures 50 may be used in this embodiment as well as others. In this embodiment, a clip structure 50 secures one side of the flexible membrane 44c to the anterior leaflet 16a and another clip structure 50 secures the flexible membrane 44c to the posterior leaflet 16b.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and method and illustrative examples shown and described. Accordingly, departures may be made from such details without departing from the scope of the general inventive concept. For example, any of the individual features or aspects described herein may be utilized alone or together in any combination depending on the desired results and attendant advantages.

The invention claimed is:

1. Apparatus for treating blood flow regurgitation through a native heart valve including first and second native leaflets, the apparatus comprising:
a selective occlusion device sized and configured to be implanted in the native heart valve and selectively operating with at least one of the first or second native leaflets to allow blood flow through the native heart valve when the heart cycle is in diastole and reduce blood flow regurgitation through the native heart valve when the heart cycle is in systole,
a clip structure coupled with the selective occlusion device, the clip structure including a pair of clip elements, with at least one of the clip elements movable between open and closed positions, the clip structure configured to be affixed to a margin of at least one of the first or second native leaflets to secure the selective occlusion device to the native heart valve with the clip elements capturing leaflet tissue therebetween in the closed position.

2. The apparatus of claim 1, wherein the clip structure includes a first clip and a second clip, the pair of clip elements being a first pair of clip elements, the first clip including the first pair of clip elements, the second clip including a second pair of clip elements, with at least one of the clip elements of each pair of clip elements movable between open and closed positions relative to the other clip element of each pair of clip elements, and wherein the first clip is configured to attach the first native leaflet to the selective occlusion device and the second clip is configured to attach the second native leaflet to the selective occlusion device.

3. The apparatus of claim 2, wherein the selective occlusion device includes a prosthetic heart valve including a movable valve element configured to selectively control blood flow through the native heart valve.

4. The apparatus of claim 3, wherein the movable valve element includes a flexible membrane configured to engage at least one of the first or second native leaflets of the native heart valve when the heart cycle is in systole and disengage the at least one of the first or second native leaflets when the heart cycle is in diastole.

5. The apparatus of claim 3, wherein the movable valve element includes a flexible membrane configured to engage the first and second native leaflets of the native heart valve when the heart cycle is in systole and disengage the first and second native leaflets when the heart cycle is in diastole.

6. The apparatus of claim 5, wherein the flexible membrane includes a closed end and an open end, and the open end receives blood flow when the heart cycle is in systole to expand the membrane into engagement with the first and second native leaflets and the open end closes when the heart cycle is in diastole to allow blood flow between the membrane and the first and second native leaflets.

7. The apparatus of claim 1, further comprising:
a frame structure coupled with the clip structure, and a non-penetrating annulus connector coupled with the frame structure, the annulus connector configured to engage with heart tissue without penetrating through the tissue, wherein the frame structure is configured to extend across the native heart valve generally between the commissures and the selective occlusion device is secured in place generally between the clip structure and the annulus connector.

8. The apparatus of claim 7, wherein the annulus connector provides a first force on heart tissue generally at the annulus, and the clip structure provides a second, opposing force at a lower margin of at least one of the first or second native leaflets to hold the selective occlusion device therebetween.

9. The apparatus of claim 1, wherein the selective occlusion device includes a prosthetic heart valve including a movable valve element configured to selectively control blood flow through the native heart valve.

10. Apparatus for treating blood flow regurgitation through a native heart valve including first and second native leaflets, the apparatus comprising:
a selective occlusion device sized and configured to be implanted in the native heart valve, the selective occlusion device including a prosthetic heart valve including a flexible membrane configured to selectively control blood flow through the native heart valve by engaging at least one of the first or second native leaflets of the native heart valve when the heart cycle is in systole and disengaging the at least one of the first or second native leaflets when the heart cycle is in diastole; and
a clip structure coupled with the selective occlusion device, the clip structure configured to be affixed to a margin of at least one of the first or second native leaflets to secure the selective occlusion device to the native heart valve.

11. The apparatus of claim 10, wherein the flexible membrane is configured to engage the first and second native leaflets of the native heart valve when the heart cycle is in systole and disengage the first and second native leaflets when the heart cycle is in diastole.

12. The apparatus of claim 11, wherein the flexible membrane includes a closed end and an open end, wherein the open end receives blood flow when the heart cycle is in systole to expand the membrane into engagement with the first and second native leaflets and the open end closes when the heart cycle is in diastole to allow blood flow between the membrane and the first and second native leaflets.

13. The apparatus of claim 11, further comprising:
a frame structure coupled with the clip structure, and
an annulus connector coupled with the frame structure, the annulus connector configured to engage with heart tissue generally at the annulus of the native heart valve,
wherein the frame structure is configured to extend across the native heart valve and the prosthetic heart valve is secured in place generally between the clip structure and the annulus connector.

14. The apparatus of claim 13, wherein the clip structure includes a pair of clip elements movable between open and closed positions and a spacer mounted between the pair of clip elements, the clip elements configured to capture native leaflet tissue between the clip elements and the spacer when the clip elements are in the closed positions.

15. The apparatus of claim 1, wherein the selective occlusion device includes a rigid element sized and configured to be implanted in the native heart valve such that at least one of the first or second native leaflets engages the rigid element when the heart cycle is in systole to reduce blood flow through the native heart valve, and the at least one of the first or second native leaflets disengages the rigid element when the heart cycle is in diastole to allow blood flow through the native heart valve.

16. The apparatus of claim 1, further comprising:
at least one catheter carrying the selective occlusion device and the clip structure, wherein the at least one catheter is configured to deliver the selective occlusion device and the clip structure to the site of the native heart valve, and the selective occlusion device has a collapsed condition for delivery through the at least one catheter and an expanded condition for implantation in the native heart valve.

17. The apparatus of claim 16, further comprising:
a frame structure having a collapsed condition for delivery through the at least one catheter and an expanded condition for implantation at the native heart valve, and
an annulus connector coupled with the frame structure, the annulus connector configured to engage with heart tissue generally at the annulus of the native heart valve,
wherein the frame structure is configured to extend across the native heart valve and the selective occlusion device is secured in place generally between the clip structure and the annulus connector.

18. The apparatus of claim 17, further comprising:
a clip structure capturing device extendable from the at least one catheter and configured to capture the clip structure and connect the clip structure to the frame structure during implantation of the selective occlusion device.

19. Apparatus for treating blood flow regurgitation through a native heart valve including first and second native leaflets, the apparatus comprising:
a selective occlusion device including a first selective occlusion element and a second selective occlusion element sized and configured to be implanted in the native heart valve such that at least one of the first or second native leaflets engages the first and second selective occlusion elements when the heart cycle is in systole to reduce blood flow through the native heart valve, and the at least one of the first or second native leaflets disengages the first and second selective occlusion elements when the heart cycle is in diastole to allow blood flow through the native heart valve; and
a clip structure coupled with the selective occlusion device, the clip structure configured to be affixed to a margin of at least one of the first or second native leaflets to secure the selective occlusion device to the native heart valve.

20. The apparatus of claim 19, wherein the clip structure includes a clip having a pair of clip elements, with at least one of the clip elements movable between open and closed positions and configured to capture native leaflet tissue therebetween in the closed position.

21. The apparatus of claim 19, wherein each of the selective occlusion elements includes a flexible membrane configured to engage at least one of the first or second native leaflets of the native heart valve when the heart cycle is in systole and disengage the at least one of the first or second native leaflets when the heart cycle is in diastole.

22. The apparatus of claim 19, further comprising:
a frame structure coupled with the clip structure, and
a non-penetrating annulus connector coupled with the frame structure, the annulus connector configured to engage with heart tissue without penetrating through the tissue, wherein the frame structure is configured to extend across the native heart valve generally between the commissures and the selective occlusion device is secured in place generally between the clip structure and the annulus connector.

23. The apparatus of claim 22, wherein the annulus connector provides a first force on heart tissue generally at the annulus, and the clip structure provides a second, opposing force at a lower margin of at least one of the first or second native leaflets to hold the selective occlusion device therebetween.

24. The apparatus of claim 19, wherein the first selective occlusion element is located on a first side of the clip structure and the second selective occlusion element is located on a second, opposite side of the clip structure.

25. The apparatus of claim 5, wherein the flexible membrane includes first and second portions each configured to engage the first and second native leaflets of the native heart valve to reduce blood flow through the native heart valve when the heart cycle is in systole and disengage the first and second native leaflets to allow blood flow through the native heart valve when the heart cycle is in diastole, wherein the first portion is located on a first side of the clip structure and the second portion is located on a second, opposite side of the clip structure.

26. The apparatus of claim 11, wherein the flexible membrane includes first and second portions each configured to engage the first and second native leaflets of the native heart valve to reduce blood flow through the native heart valve when the heart cycle is in systole and disengage the first and second native leaflets to allow blood flow through the native heart valve when the heart cycle is in diastole, wherein the first portion is located on a first side of the clip structure and the second portion is located on a second, opposite side of the clip structure.

* * * * *